(12) United States Patent
Commons et al.

(10) Patent No.: US 6,589,970 B2
(45) Date of Patent: Jul. 8, 2003

(54) 6-(ARYL-AMIDO OR ARYL-AMIDOMETHYL)-NAPHTHALEN-2-YLOXY-ACIDIC DERIVATIVES AS INHIBITORS OF PLASMINOGEN ACTIVATOR INHIBITOR TYPE-1 (PAI-1)

(75) Inventors: Thomas Joseph Commons, Wayne, PA (US); Susan Christman Croce, Lambertville, NJ (US); Richard Page Woodworth, Eagleville, PA (US); Eugene John Trybulski, Princeton Junction, NJ (US); Hassan Mahmoud Elokdah, Yardley, PA (US); David LeRoy Crandall, Doylestown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/170,558

(22) Filed: Jun. 13, 2002

(65) Prior Publication Data

US 2003/0045560 A1 Mar. 6, 2003

Related U.S. Application Data

(60) Provisional application No. 60/308,656, filed on Jul. 30, 2001, and provisional application No. 60/299,652, filed on Jun. 20, 2001.

(51) Int. Cl.[7] .................. A61K 31/343; C07D 307/78; A61P 7/02

(52) U.S. Cl. .................. 514/382; 514/374; 514/378.1; 514/381; 514/406; 514/419; 514/470; 514/471; 514/569; 548/252; 548/374.1; 548/492; 548/236; 549/467; 549/488; 560/21; 560/22

(58) Field of Search .................. 549/467, 488; 548/252, 374.1, 492, 236, 248; 560/21, 22; 514/374, 378, 381, 382, 406, 419, 470; 541/471, 569

(56) References Cited

U.S. PATENT DOCUMENTS

5,530,019 A 6/1996 Okada et al.

FOREIGN PATENT DOCUMENTS

| GB | 2 286 395 A | | 8/1995 |
|---|---|---|---|
| WO | WO 96/04267 | * | 2/1996 |
| WO | WO 00/31045 A | | 6/2000 |

OTHER PUBLICATIONS

Derwent Database Search, XP002215106, 1999.
Nordt et al., The Journal of Clinical Endocrinology & Metabolism, 85(4), 1563–1568 (2000).
Aznar et al., Haemostasis, 24, 243–251 (1994).
Carmeliet et al., Journal of Clinical Invest., 92, 2756–2760 (1993).
Daci et al., Journal of Bone & Mineral Research, 15(8), 1510–1516 (2000).
Biemond et al., Circulation, 91(4), 1175–1181 (1995).
Levi, et al., Circulation, 85(1), 305–312 (1992).
Rocha, et al., Fibrinolysis, 8, 294–303 (1994).
Reilly et al., Arteriosclerosis & Thrombosis 11, 1276–1286 (1991).
Krishnamurti et al., Blood, 69(3), 798–803 (1987).

* cited by examiner

*Primary Examiner*—Joseph K. McKane
*Assistant Examiner*—Andrea D. Small
(74) *Attorney, Agent, or Firm*—Michael R. Nagy

(57) ABSTRACT

This invention provides novel compounds, pharmaceutical compositions and methods of treating thrombotic disorders in mammals, the compounds having the formula:

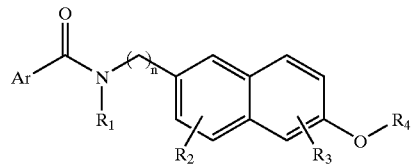

Wherein: Ar is phenyl, naphthyl, furanyl, benzofuranyl, indolyl, pyrazolyl, oxazolyl, fluorenyl, phenylcycloalkane where the cycloalkane can be cyclopropyl, cyclobutyl, cyclopentyl or cyclohexyl and Ar can be optionally substituted by 1 to 3 groups selected from $C_1$–$C_6$ alkyl, $C_1$–$C_6$ alkoxy, hydroxy, phenyl-$(CH_2)_{0-6}$—, phenyl-$(CH_2)_{0-6}O$—, $C_3$–$C_6$ cycloalkyl, —$(CH_2)$—$C_3$–$C_6$ cycloalkyl, halogen, $C_1$–$C_3$ perflouroalkyl and $C_1$–$C_3$ perfluoroalkoxy where phenyl can be substituted with from 1 to 3 groups selected from $C_1$–$C_6$ alkyl, $C_1$–$C_6$ alkoxy, phenyl, halogen, trifluoromethyl or trifluoromethoxy; $R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halo, trifluoromethyl or trifluoromethoxy; $R_2$ and $R_3$ are H, $C_1$–$C_6$ alkyl, phenyl-$(CH_2)_{0-3}$—, halo and $C_1$–$C_3$ perfluoroalkyl where phenyl can be substituted with $C_1$–$C_6$ alkyl, $C_1$–$C_6$ alkoxy, halo, trifluoromethyl or trifluoromethoxy; $R_4$ is —$CHR_5CO_2H$ or —$CH_2$-tetrazole where $R_5$ is H or benzyl; and n=0 or 1; or a pharmaceutically acceptable salt or ester form thereof.

38 Claims, No Drawings

6-(ARYL-AMIDO OR ARYL-AMIDOMETHYL)-NAPHTHALEN-2-YLOXY-ACIDIC DERIVATIVES AS INHIBITORS OF PLASMINOGEN ACTIVATOR INHIBITOR TYPE-1 (PAI-1)

This application claims benefit of 60/308,656 Jul. 30, 2001 and claims benefit of 60/299,652 Jun. 20, 2001.

This invention relates to the composition and utility of 6-(aryl-amido or aryl-amidomethyl)-naphthalen-2-yloxy-acidic derivatives as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF THE INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary embolism, polycystic ovary syndrome, etc.

U.S. Pat. No. 5,530,019 describes compounds of the general formula:

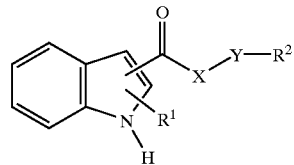

wherein $R^1$ is optionally protected carboxy(lower)alkyl, $R^2$ is H, optionally substituted aryl or carboxy; X is a bond, —O—, —NH— or a cycloalkylene, and Y is an alkylene which may be interrupted by an oxygen atom, an alkenylene or an alkadienylene, which are described as useful as testosterone 5α-reductase inhibitors useful in treating such diseases as prostatism, prostatic hypertrophy, prostatic cancer, alopecia, hirsutism, androgenic alopecia, acne, and other hyperandrogenisms.

DESCRIPTION OF THE INVENTION

This invention comprises compounds of the formula:

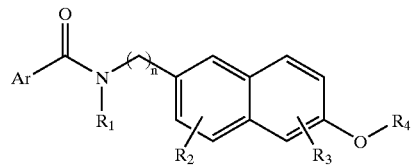

Wherein:

Ar is phenyl, naphthyl, furanyl, benzofuranyl, indolyl, pyrazolyl, oxazolyl, fluorenyl, phenylcycloalkane where the cycloalkane can be cyclopropyl, cyclobutyl, cyclopentyl or cyclohexyl and Ar can be optionally substituted by from 1 to 3 groups selected from $C_1$–$C_6$ alkyl, $C_1$–$C_6$ alkoxy, hydroxy, phenyl-$(CH_2)_{0-6}$—, phenyl-$(CH_2)_{0-6}O$—, $C_3$–$C_6$ cycloalkyl, —$(CH_2)$—$C_3$–$C_6$ cycloalkyl, halogen, $C_1$–$C_3$ perflouroalkyl and $C_1$–$C_3$ perfluoroalkoxy where phenyl can be substituted with from 1 to 3 groups selected from $C_1$–$C_6$ alkyl, $C_1$–$C_6$ alkoxy, phenyl, halogen, trifluoromethyl or trifluoromethoxy;

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy;

$R_4$ is —$CHR_5CO_2H$, —$CH_2$-tetrazole or an acid mimic or mimetic; where $R_5$ is hydrogen or optionally substituted benzyl; and n=0 or 1;

or a pharmaceutically acceptable salt or ester form thereof.

One group of compounds of this invention includes those of the formulae 1 or

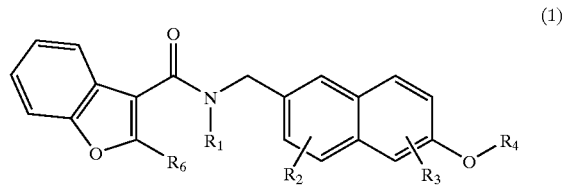

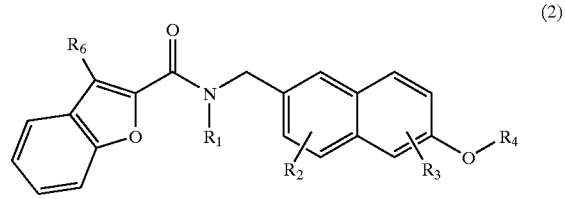

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy.

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or an acid mimic such as tetrazole, —$CH_2$-tetrazole, $SO_3H$, $PO_3H_2$, tetronic acid, etc.;

$R_5$ is hydrogen or benzyl;

$R_6$ is selected from $C_1$–$C_6$ alkyl, $C_1$–$C_6$ alkoxy, hydroxy, phenyl-$(CH_2)_{0-6}$—, phenyl-$(CH_2)_{0-6}O$—, $C_3$–$C_6$, cycloalkyl, halogen, $C_1$–$C_3$ perflouroalkyl and $C_1$–$C_3$ perfluoroalkoxy; where the phenyl ring in these $R_6$ groups can be substituted with $C_1$–$C_6$ alkyl, $C_1$–$C_6$ alkoxy, phenyl-$(CH_2)_{0-3}$—, halogen, trifluoromethyl or trifluoromethoxy;

or a pharmaceutically acceptable salt or ester form thereof.

A second group of compounds of this invention includes those of the formula:

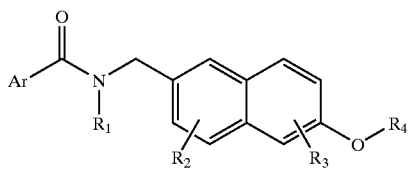

wherein:

Ar is a moiety selected from the group of:

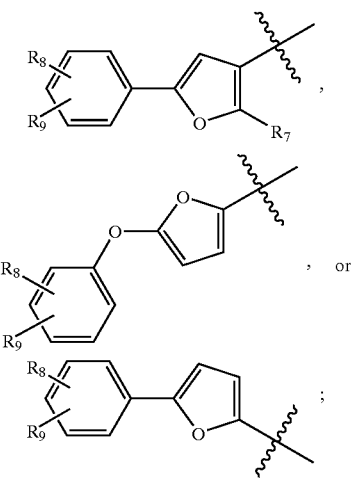

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy.

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or an acid mimic such as tetrazole, —$CH_2$-tetrazole, $SO_3H$, $PO_3H_2$, tetronic acid, etc.;

$R_5$ is hydrogen or benzyl;

$R_7$ is selected from $C_1$–$C_6$ alkyl, $C_1$–$C_6$ alkoxy, hydroxy, phenyl-$(CH_2)_{0-6}$—, phenyl-$(CH_2)_{0-6}O$—, $C_3$–$C_6$ cycloalkyl, halogen, $C_1$–$C_3$ perflouroalkyl and $C_1$–$C_3$ perfluoroalkoxy; where the phenyl ring in these $R_7$ groups can be substituted with $C_1$–$C_6$ alkyl, $C_1$–$C_6$alkoxy, phenyl, halogen, trifluoromethyl or trifluoromethoxy;

$R_8$ and $R_9$ are each independently selected from H, $C_1$–$C_6$ alkyl, $C_1$–$C_6$ alkoxy, phenyl-$(CH_2)_{0-3}$—, halogen, trifluoromethyl or trifluoromethoxy;

or a pharmaceutically acceptable salt or ester form thereof.

A third subgroup of compounds of this invention comprises those of the formula:

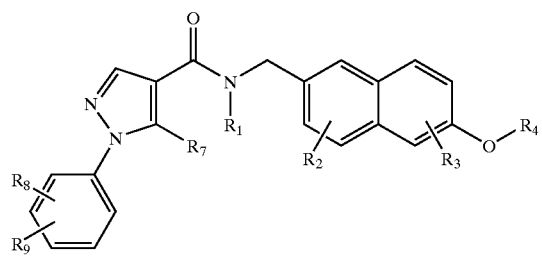

wherein:

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy.

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or an acid mimic such as tetrazole, —$CH_2$-tetrazole, $SO_3H$, $PO_3H_2$, tetronic acid, etc.;

$R_5$ is hydrogen or benzyl;

$R_7$ is selected from $C_1$–$C_6$ alkyl, $C_1$–$C_6$ alkoxy, hydroxy, phenyl-$(CH_2)_{0-6}$—, phenyl-$(CH_2)_{0-6}O$—, $C_3$–$C_6$, cycloalkyl, halogen, $C_1$–$C_3$ perflouroalkyl and $C_1$–$C_3$ perfluoroalkoxy; where the phenyl ring in these $R_7$ groups can be substituted with $C_1$–$C_6$ alkyl, $C_1$–$C_6$ alkoxy, phenyl-$(CH_2)_{0-3}$—, halogen, trifluoromethyl or trifluoromethoxy;

$R_8$ and $R_9$ are each independently selected from H, $C_1$–$C_6$ alkyl, $C_1$–$C_6$ alkoxy, phenyl, halogen, trifluoromethyl or trifluoromethoxy;

or a pharmaceutically acceptable salt or ester form thereof.

A fourth subgroup of compounds of this invention comprises those of the formula:

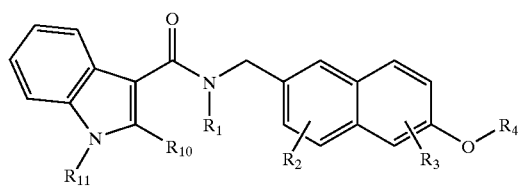

wherein:

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy.

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or an acid mimic such as tetrazole, —$CH_2$-tetrazole, $SO_3H$, $PO_3H_2$, tetronic acid, etc.;

$R_5$ is hydrogen or benzyl;

$R_{10}$ is selected from $C_1$–$C_6$ alkyl, $C_1$–$C_6$ alkoxy, hydroxy, $C_3$–$C_6$, cycloalkyl, halogen, $C_1$–$C_3$ perflouroalkyl and $C_1$–$C_3$ perfluoroalkoxy;

$R_{11}$ is selected from $C_1$–$C_6$ alkyl, phenyl-$(CH_2)_{0-6}$—, $C_3$–$C_6$ cycloalkyl, or —$(CH_2)$— $C_3$–$C_6$ cycloalkyl; where the phenyl ring in these $R_7$ groups can be substituted with $C_1$–$C_6$ alkyl, $C_1$–$C_6$ alkoxy, phenyl, halogen, trifluoromethyl or trifluoromethoxy;

Or a pharmaceutically acceptable salt or ester form thereof.

A fifth subgroup of compounds of this invention are those of the formula:

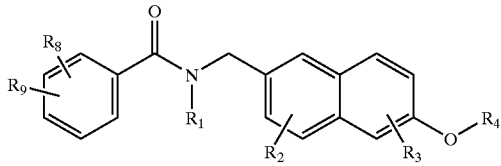

wherein:
$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy.

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or an acid mimic such as tetrazole, —$CH_2$-tetrazole, $SO_3H$, $PO_3H_2$, tetronic acid, etc.;

$R_5$ is hydrogen or benzyl;

$R_8$ and $R_9$ are each independently selected from H, $C_1$–$C_6$ alkyl, $C_1$–$C_6$ alkoxy, phenyl, halogen, trifluoromethyl or trifluoromethoxy;

or a pharmaceutically acceptable salt or ester form thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-mehtyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —$COOR_5$ wherein $R_5$ is selected from the formulae:

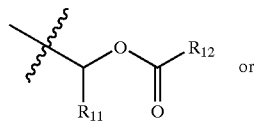

(1)

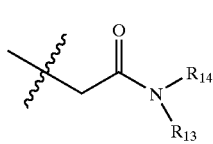

(2)

wherein $R_{11}$, $R_{12}$, $R_{13}$, $R_{14}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

Acid mimic or mimetics which are included in the acidic groups of this invention, as noted in the definition of A, above, particularly include the pharmaceutically useful carboxylic acid mimics or mimetics known in the art, such as those described in R. Silverman, The Organic Chemistry of Drug Design and Drug Action, Academic Press (1992), the contents of which are incorporated herein by reference. Non-limiting examples of these acid mimics include such as tetrazole, $SO_3H$, $PO_3H_2$, tetronic acid, etc., or groups having the formulae:

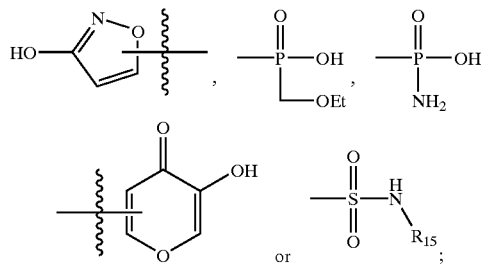

wherein $R_{15}$ is $C_1$–$C_6$ alkyl, $C_2$–$C_6$ alkenyl, $C_3$–$C_6$ cycloalkyl, —$CH_2$—$(C_3$–$C_6$ cycloalkyl), $C_3$–$C_6$ cycloalkenyl, —$CH_2$—$(C_3$–$C_6$ cycloalkenyl), optionally substituted aryl or heteroaryl groups or optionally substituted —$C_1$–$C_6$ alkyl-aryl or —$C_1$–$C_6$ alkyl-heteroaryl, with the aryl and heteroaryl groups and their optional substitution as defined herein.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases which orginate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type I and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

DETAILED DESCRIPTION OF THE INVENTION

The compounds of this invention are conveniently prepared by the routes shown in Scheme 1, 2 and 3. Specific examples are given in the Experimental Section. These examples are for illustrative purposes only and are not to be construed as limiting to this disclosure in any way. Those skilled in the art will be aware of other methods of preparing the compounds of this invention. The starting materials are available commercially or can be prepared by standard literature procedures.

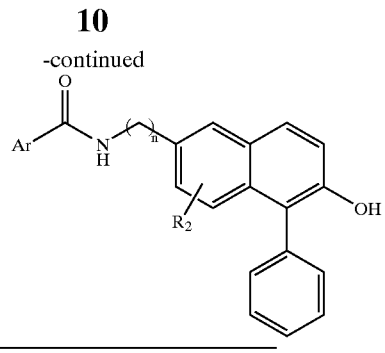

For $R_3$ = H; Br or phenyl

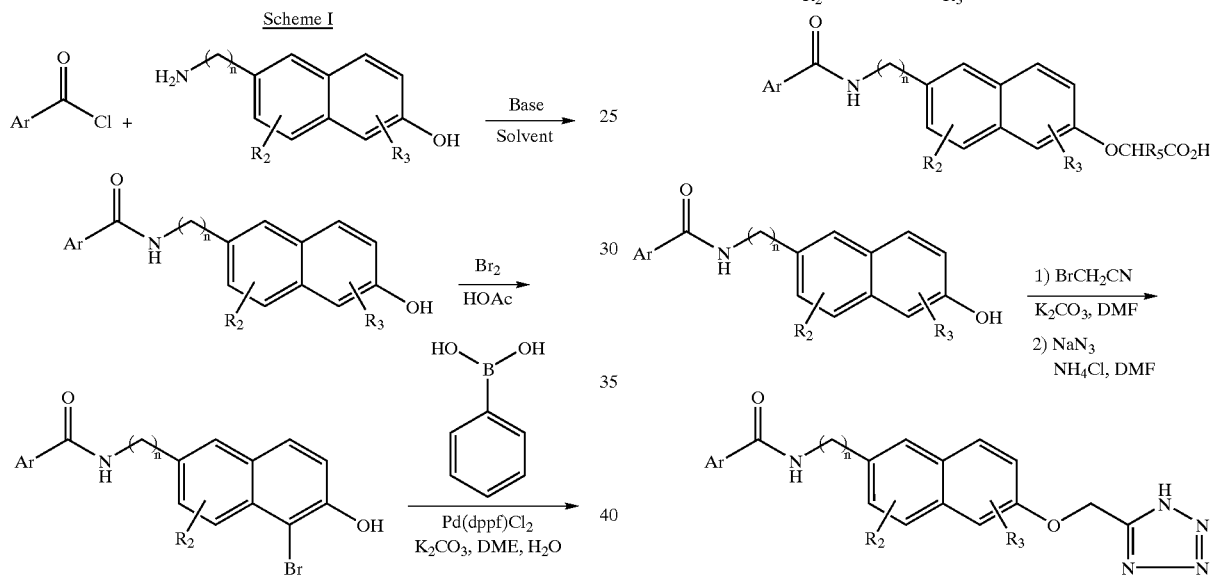

-continued

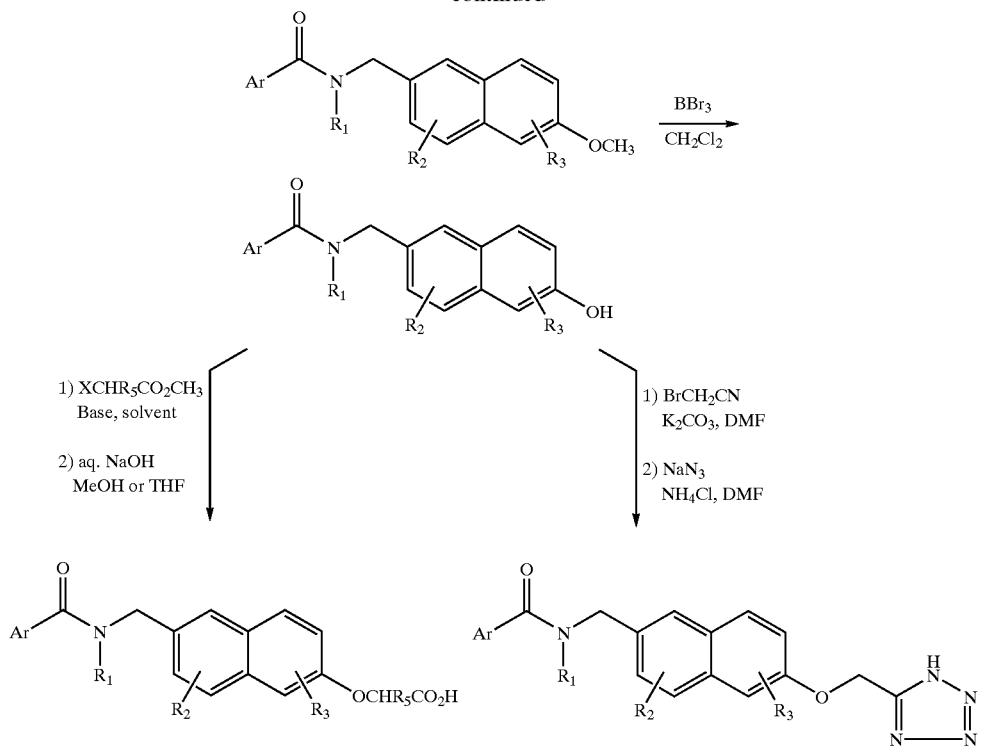

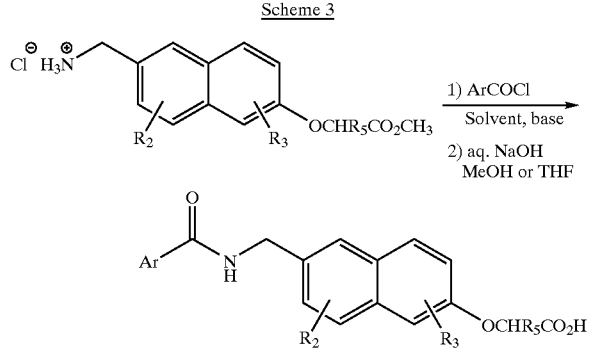

Scheme 3

This invention also provides pharmaceutical compositions comprised of 6-(aryl-amido or aryl-amidomethyl)-naphthalen-2-yloxy-acidic derivatives either alone or in combination with excipients (i.e. pharmaceutically acceptable materials with no pharmacological effects). Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit Plasminogen Activator Inhobitor (type I) was established by the following experimental procedures:

Primary Screen for the PAI-1 Inhibition

Test compounds are dissolved in DMSO at a final concentration of 10 mM, then diluted 100× in physiologic buffer. The inhibitory assay is initiated by the addition of the test compound (1–100 μM final concentration, maximum DMSO concentration of 0.2%) in a pH 6.6 buffer containing 140 nM recombinant human plasminogen activator inhibitor-1 (PAI-1; *Molecular Innovations*, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the test compound on tPA alone.

Assay for Determining $IC_{50}$ of Inhibition of PAI-1

This assay is based upon the non-SDS dissociable interaction between tPA and active PAI-1. Assay plates are initially coated with human tPA (10 μg/ml). The test compounds are dissolved in DMSO at 10 mM, then diluted with physiologic buffer (pH 7.5) to a final concentration of 1–50 μM. The test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations*, Royal Oak, Mich. The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table I:

TABLE I

| Example | $IC_{50}$ (μM)[a] | $IC_{50}$ (μM)[b] | % Inhib. 100 μM | % Inhib. 25 μM |
|---|---|---|---|---|
| 1 |  |  | 23 |  |
| 2 |  |  | 52 | 21 |
| 3 |  | 3.2 | 75 | 38 |
| 4 |  |  | 66 | 3 |
| 5 |  |  | 47 |  |
| 6 |  | 18.3 | 67 | 43 |
| 7 | 16.62 | 7.8 | 83 | 64 |
| 8 |  | 22.9 | 71 | 13 |
| 9 |  |  | 89 | 28 |
| 10 |  | 25.2 | 53 | 7 |
| 11 |  |  | 32 |  |
| 12 |  |  | 66 | 5 |
| 13 |  |  | 52 | 5 |
| 14 | 51 |  | 70 | 1 |
| 15 |  |  | 92 | 5 |
| 16 |  |  | 85 | 12 |
| 17 | 16.11 | 1.4 | 80 |  |
| 18 | 15.72 |  | 92 | 53 |
| 19 |  |  | 32 |  |
| 20 | 15.8 |  | 58 | 26 |
| 21 | 5.08 |  | 54 | 36 |
| 22 |  |  | 70 | 12 |
| 23 |  |  | 48 |  |
| 24 | 16.82 | 9.94 | 72 | 25 |
| 25 |  | 4.6 | 94 | 3 |
| 26 |  | 4.3 | 98 | 20 |
| 27 |  |  | 39 |  |
| 28 |  | 20.2 | 100 | 22 |
| 29 |  | 8.5 | 100 | 23 |
| 30 | 44.94 |  | 91 | 38 |
| 31 | 8.47 | 15.6 | 95 | 62 |
| 32 | 25.88 |  | 70 | 1 |
| 33 | 31.13 |  | 94 | 59 |
| 34 | 19.3 |  | 81 | 34 |
| 35 |  |  | 72 | 26 |
| 36 |  |  | 46 | 4 |
| 37 | 20.64 |  | 96 | 52 |
| 38 |  |  | 81 | 47 |
| 39 |  |  | 69 | 24 |
| 40 |  |  | 96 | 60 |
| 41 |  |  | 91 | 49 |
| 42 |  |  | 79 | 63 |
| 43 |  |  | 71 | 47 |
| 44 |  |  |  |  |
| 45 |  |  | 17 |  |
| 46 |  |  | 88 | 58 |
| 47 |  |  | 90 | 59 |
| 48 | 17.51 | 20.9 | 85 | 48 |

TABLE I-continued

| Example | IC$_{50}$ (μM)[a] | IC$_{50}$ (μM)[b] | % Inhib. 100 μM | 25 μM |
|---|---|---|---|---|
| 49 | 6.92 | | 72 | 54 |
| 50 | 35.66 | | 61 | 56 |
| 51 | 18.67 | 6.9 | 91 | 69 |
| 52 | 20.78 | | 81 | 44 |
| 53 | 8.12 | 8.7 | 86 | 35 |
| 54 | | 11.8 | 80 | 18 |
| 55 | 16.8 | 11.8 | 60 | 35 |
| 56 | | 1.9 | 100 | 84 |
| 57 | | 5.5 | 98 | 24 |
| 58 | | | 29 | |
| 59 | | | 44 | |
| 60 | | | 30 | |
| 61 | | | 75 | 24 |
| 62 | | | 84 | 1 |
| 63 | | | 69 | 14 |
| 64 | 13.61 | | 60 | 40 |
| 65 | 14.64 | | 88 | 46 |
| 66 | | | 95 | 46 |
| 67 | 13.47 | | 66 | 59 |
| 68 | 19.96 | | 84 | 54 |
| 69 | 16.78 | | 92 | 55 |
| 70 | | | 81 | 17 |
| 71 | | | 78 | 47 |
| 72 | | | 68 | 56 |
| 73 | | | 65 | 23 |
| 74 | | | 59 | 20 |
| 75 | | | 55 | 1 |
| 76 | | | 54 | 0 |
| 77 | | | 51 | 27 |
| 78 | | | 51 | 24 |
| 79 | | | 50 | 19 |
| 80 | | | 48 | |
| 81 | | 36.5 | 78 | 12 |
| 82 | | | 68 | 9 |
| 83 | | | 45 | |
| 84 | | | 34 | |
| 85 | | | 34 | |
| 86 | | | 33 | |
| 87 | | | 32 | |

[a]The IC$_{50}$ was determined by the Antibody Assay described above.
[b]The IC$_{50}$ was deteremined by a modification of the Primary Screen for the PAI-1 Inhibition.

This invention is further illustrated by the following non-limiting examples.

EXAMPLE 1

(6-{[Benzofuran-2-carbonyl)-amino]-methyl}-naphthalen-2-yloxy)-acetic acid

Step 1: C-(6-Methoxy-naphthalen-2-yl)-methylamine. BH$_3$-THF (245 mL of a 1 M solution, 245 mmol) was added under nitrogen dropwise over 30 minutes to a solution of 6-methoxy-naphthalene-2-carbonitrile (15.0 g, 82 mmol) in 300 mL of anhydrous THF at room temperature. After the addition the reaction was refluxed for 22 h. By TLC starting material remained. An additional 82 mL (82 mmol) of BH$_3$-THF was added and the reaction refluxed for 3 h. 1 N HCL was added slowly until the reaction was acidic. The reaction was concentrated under reduced pressure to remove the THF. The solid present was removed by filtration and the filtrate made basic by the addition of 5% NaHCO$_3$. The solid which precipitated was collected by filtration and dried under reduced pressure to give C(6-Methoxy-naphthalen-2-yl)-methylamine (11.35 g, 74%) as a white solid, mp 115–122° C., MS m/z 187 [M]$^+$.

Elemental Analysis for C$_{12}$H$_{13}$NO+0.66 H$_2$O Calc'd: C, 72.38; H, 7.25; N, 7.03 Found: C, 65.88; H, 6.57; N, 5.86

Step 2: 6-Hydroxy-naphthalen-2-ylmethyl-ammonium; bromide. A mixture of C-(6-methoxy-naphthalen-2-yl)-methylamine (13.0 g, 69 mmol), prepared in the previous step, and 350 mL of 48% HBr was refluxed for 24 h. The solvent was removed under reduced pressure to give 6-hydroxy-naphthalen-2-ylmethyl-ammonium; bromide (18.5 g, 95%) as a brown solid, MS m/z 173 [M]$^+$.

Elemental Analysis for C$_{11}$H$_{12}$BrNO+1.55 H$_2$O Calc'd: C, 46.48; H, 5.40; N, 4.97 Found: C, 42.96; H, 4.31; N, 4.50

Step 3: Benzofuran-2-carbonyl chloride. DMF (75 μL) was added under nitrogen to a solution of benzofuran-2-carboxylic acid (5.0 g, 30.8 mmol) and oxalyl chloride (13.3 mL, 154 mmol) in 175 mL of methylene chloride at room temperature. After the addition the reaction was stirred at room temperature for 1 h. The solvent and excess oxalyl chloride were removed under reduced pressure to give 5.72 g of a white solid which was used in the next step without additional purification.

Step 4: Benzofuran-2-carboxylic acid (6-hydroxy-naphthalen-2-ylmethyl)-amide. Benzofuran-2-carbonyl chloride (5.02 g, 27.8 mmol), prepared in the previous step, in 100 mL of anhydrous THF was added under nitrogen dropwise over 30 minutes to a mixture of 6-hydroxy-naphthalen-2-ylmethyl-ammonium; bromide (7.06 g, 27.8 mmol), prepared in step 2, and triethylamine (8.5 mL, 61.1 mmol) in 400 mL of anhydrous THF at ice bath temperature. After the addition the reaction was stirred at ice bath temperature for approximately 2 h and then overnight at room temperature. The solid was removed by filtration and the filtrate concentrated under reduced pressure to give 9.14 g a brown foam. To remove residual amounts of triethylamine the foam was triturated with water. Methylene chloride (150 mL) was added to the residue. The material that did not dissolve was collected by filtration and dried under reduced pressure to give benzofuran-2-carboxylic acid (6-hydroxy-naphthalen-2-ylmethyl)-amide (1.44 g, 15%) as a brown solid. Upon cooling the filtrate a solid formed. The solid was collected by filtration and dried under reduced pressure to give an additional 2.46 g (26%) of the desired product, mp 200–202° C.

Elemental Analysis for C$_{20}$H$_{15}$NO$_3$+0.23 CH$_2$Cl$_2$ Calc'd: C, 72.13; H, 4.63; N, 4.16 Found: C, 69.30; H, 4.58; N, 3.93

Step 5: (6-{[Benzofuran-2-carbonyl)-amino]-methyl}-naphthalen-2-yloxy)-acetic acid methyl ester. A mixture of benzofuran-2-carboxylic acid (6-hydroxy-naphthalen-2-ylmethyl)-amide (1.5 g, 4.73 mmol), prepared in the previous step, methyl bromoacetate (473 μL, mmol) and potassium carbonate (3.27 g, 23.6 mmol) in 30 mL of DMF was stirred under nitrogen at room temperature overnight. The reaction was diluted with methylene chloride, extracted multiple times with water, dried (MgSO$_4$) and the solvent removed under reduced pressure to give 1.66 g of a tan solid. Recrystallization of the solid from isopropyl alcohol gave (6-{[benzofuran-2-carbonyl)-amino]-methyl}-naphthalen-2-yloxy)-acetic acid methyl ester (1.12 g, 60%) as a tan solid, mp 170–171° C.

Elemental Analysis for C$_{23}$H$_{19}$NO$_5$ Calc'd: C, 70.94; H, 4.92; N, 3.60 Found: C, 70.01; H, 5.23; N, 3.47

Step 6: (6-{[Benzofuran-2-carbonyl)-amino]-methyl}-naphthalen-2-yloxy)-acetic acid. A mixture of (6-{[benzofuran-2-carbonyl)-amino]-methyl}-naphthalen-2-yloxy)-acetic acid methyl ester (947 mg, 2.43 mmol), prepared in the previous step, and 1 N NaOH (2.7 mL, 2.67 mmol) in 50 mL of THF and 25 mL of water was stirred at room temperature for 2 h. The reaction was concentrated under reduced pressure to remove the THF. A white solid was present in the residual aqueous layer. This aqueous mixture was diluted with 250 mL of boiling water. The solid that did not dissolve was collected by filtration and dried under reduced pressure to give (6-{[benzofuran-2-carbonyl)-amino]-methyl}-naphthalen-2-yloxy)-acetic acid as its sodium salt (303 mg, 27%) as a light pink solid. When the filtrate cooled to room temperature additional solid formed. The solid was collected by filtration and dried under reduced pressure to give an additional 328 mg (29%) of the salt. The filtrate was then acidified with 1 N HCl. A solid immediately precipitated. The solid was collected by filtration and dried under reduced pressure to give the title compound (40 mg, 4%) as a brown solid, mp 143–147° C.; MS m/z 374 [M–H]⁻.

Elemental Analysis for $C_{22}H_{17}NO_5$ Calc'd: C, 70.39; H, 4.56; N, 3.73 Found: C, 66.37; H, 4.75; N, 3.52

EXAMPLE 2

Benzofuran-2-carboxylic acid [6-(2H-tetrazol-5-ylmethoxy-naphthalen-2-ylmethyl]-amide Step 1: Benzofuran-2-carboxylic acid (6-cyanomethoxy-naphthalen-2-ylmethyl)-amide. A mixture of benzofuran-2-carboxylic acid (6-hydroxy-naphthalen-2-ylmethyl)-amide (1.35 g, 4.27 mmol), prepared in step 4 of Example 1, bromoacetonitrile (326 μL, 4.69 mmol) and potassium carbonate (2.9 g, 21.3 mmol) in 25 mL of DMF was stirred under nitrogen at room temperature overnight. By TLC starting material remained. An additional 594 μL (8.53 mmol) of bromoacetonitrile was added and the reaction stirred at room temperature overnight. The reaction was diluted with methylene chloride, extracted multiple times with water, dried (MgSO₄) and the solvent removed under reduced pressure to give 1.27 g of a brown solid. Purification of the solid on a 90 g KP-SIL 60 A° Biotage column using 1% ethyl acetate in methylene chloride as the eluent gave benzofuran-2-carboxylic acid (6-cyanomethoxy-naphthalen-2-ylmethyl)-amide (420 mg, 28%) as a white solid, mp 138–139° C.

Elemental Analysis for $C_{22}H_{16}N_2O_3$ Calc'd: C, 74.15; H, 4.53; N, 7.86 Found: C, 72.71; H, 4.28; N, 7.62

Step 2: Benzofuran-2-carboxylic acid [6-(2H-tetrazol-5-ylmethoxy-naphthalen-2-ylmethyl]-amide. A mixture of benzofuran-2-carboxylic acid (6-cyanomethoxy-naphthalen-2-ylmethyl)-amide (200 mg, 0.561 mmol), prepared in the previous step, sodium azide (109 mg, 1.68 mmol) and ammoniun chloride (90 mg, 1.68 mmol) in 10 mL of DMF was stirred under nitrogen at 100° C. for 4 h. The reaction was diluted with water, made basic by the addition of 1 N NaOH and extracted three times with methylene chloride. The solid present in the aqueous layer was collected by filtration and dried to give 143 mg of material. The solid was taken up in 150 mL of boiling water and filtered. While warm the filtrate was acidified by the addition of 1 N HCl. The solid that formed was collected by filtration and dried under reduced pressure to give the title compound (110 mg, 49%) as a white solid, mp 212–213° C.

Elemental Analysis for $C_{22}H_{17}N_5O_3+0.40$ H2O Calc'd: C, 64.99; H, 4.41; N, 17.22 Found: C, 64.40; H, 4.21; N, 17.24

EXAMPLE 3

2-Butyl-benzofuran-3-carboxylic acid [6-(2H-tetrazol-5-ylmethoxy)-naphthalen-2-yl]-amide Step 1: 2-Butyl-benzofuran-3-carboxylic acid. Oxalyl chloride (9.9 mL, 113 mmol) in 50 mL of anhydrous carbon disulfide was added under nitrogen at room temperature to a suspension of aluminum chloride (18.2 g, 136 mmol) in 400 mL of anhydrous carbon disulfide. After the addition the reaction was stirred at room temperature for 15 minutes. 2-Butyl-benzofuran (20.0 mL, 113 mmol) in 50 mL of anhydrous carbon disulfide was then added dropwise over 30 minutes. After the addition the reaction was refluxed for 2 h. After cooling to room temperature 50 mL of 1 N HCl was added dropwise to the reaction (exotherm). The carbon disulfide was decanted from a purple sludge. The sludge was extracted with methylene chloride, combined with the carbon disulfide solution and the solvent removed under reduced pressure. The residue was partitioned between methylene chloride and water. The organic layer was separated and the aqueous layer extracted two times with methylene chloride. The combined extracts were dried (MgSO₄) and the solvent removed under reduced pressure. The residue was dissolved in 300 mL of THF plus 300 mL of 1 N NaOH and the mixture stirred at room temperature for 16 h (overnight). The THF was removed under reduced pressure and the residue partitioned between methylene chloride and water. The emulsion that formed was separated by the addition of saturated NaCl. After separating the organic layer the aqueous layer was extracted two times with methylene chloride. The aqueous layer was filtered to remove some suspended solid and then partitioned with 10% MeOH—CH₂Cl₂ and acidified with 1 N HCl. The organic layer was separated and the aqueous layer extracted two times with 10% MeOH—CH₂Cl₂. The combined extracts were dried (MgSO₄) and the solvent removed under reduced pressure to give 2-butyl-benzofuran-3-carboxylic acid (11.50 g, 47%) as a dark yellow solid, mp 106–110° C.

Elemental Analysis for $C_{13}H_{14}O_3$ Calc'd: C, 71.54; H, 6.47; N, 0.00 Found: C, 70.79; H, 6.45; N, 0.01

Step 2: 2-Butyl-benzofuran-3-carbonyl chloride. Oxalyl Chloride (10.0 mL, 114.6 mmol) was added under nitrogen at room temperature to a solution of 2-butyl-benzofuran-3-carboxylic acid (5.00 g, 22.9 mmol), prepared in the previous step, in 200 mL of methylene chloride. After the addition a catalytic amount of DMF (100 μL) was added and the reaction stirred at room temperature for 1.5 h. The solvent was removed under reduced pressure to give a brown oil. The oil was dissolved in benzene and the solvent removed under reduced pressure to give 2-butyl-benzofuran-3-carbonyl chloride (5.46 g, 100%) as a brown oil. The material was immediately used in subsequent reactions without additional purification.

Step 3: (6-Methoxy-naphthalen-2-yl)-carbamic acid tert-butyl ester. A mixture of 6-methoxy-naphthalene-2-carboxylic acid (10.00 g, 49.5 mmol), triethylamine (6.9 mL, 49.5 mmol) and diphenylphosphoryl azide (10.7 mL, 49.6 mmol) in 200 mL of anhydrous tert-butyl alcohol was refluxed under nitrogen for 5.5 h. The tert-butyl alcohol was removed under reduced pressure. The residue was dissolved in methylene chloride and extracted with 1 N HCl, 1 N NaOH, dried (MgSO₄) and the solvent removed under reduced pressure to give (6-Methoxy-naphthalen-2-yl)-carbamic acid tert-butyl ester (11.14 g, 82%) as an off-white solid, mp 124–127° C.

Elemental Analysis for $C_{16}H_{19}NO_3$ Calc'd: C, 70.31; H, 7.01; N, 5.12 Found: C, 69.83; H, 7.01; N, 5.24

Step 4: 6-Amino-naphthalen-2-ol. (6-Methoxy-naphthalen-2-yl)-carbamic acid tert-butyl ester (10.05 g, 36.8 mmol), prepared in the previous step, was suspended in 300 mL of glacial acetic acid plus 200 mL of 48% HBr and under nitrogen the mixture was refluxed for 6 h. The glacial acetic acid and the 48% HBr were removed under reduced pressure and the residue partitioned between methylene chloride and water. The aqueous layer was made basic by the addition of NaHCO₃. A solid precipitated. The solid was collected by filtration and dried under reduced pressure to give 6-amino-naphthalen-2-ol (5.72 g, 98%) as a gray solid, MS m/z: 160 [M+H]⁺.

Elemental Analysis for $C_{10}H_9NO$ Calc'd: C, 75.45; H, 5.70; N, 8.80 Found: C, 65.71; H, 4.70; N, 7.40

Step 5: 2-Butyl-benzofuran-3-carboxylic acid (6-hydroxy-naphthalen-2-yl)-amide. 2-Butyl-benzofuran-3-carbonyl chloride, prepared in step 2, in 100 mL of anhydrous THF was added under nitrogen dropwise over 2 h to a suspension of 6-amino-naphthalen-2-ol (3.02 g, 19.0 mmol), prepared in the previous step, and triethylamine (2.20 mL, 15.8 mmol) in 300 mL of anhydrous THF at ice bath temperature. After the addition the reaction was stirred at ice bath temperature for 1 h. The ice bath was removed and the stirring continued for 17 h (overnight). The solid present was removed by filtration and the filtrate concentrated to dryness under reduced pressure to give 6.70 g of a brown foam. Purification of the foam on 600 g of silica (230–400 mesh) using 1% to 3% EtOAc in CH₂Cl₂ as the eluent gave 2-butyl-benzofuran-3-carboxylic acid (6-hydroxy-naphthalen-2-yl)-amide (4.15 g, 73%) as a yellow solid, mp 162–164° C.

Elemental Analysis for $C_{23}H_{21}NO_3$ Calc'd: C, 76.86; H, 5.89; N, 3.90 Found: C, 75.90; H, 5.84; N, 3.73

Step 6: 2-Butyl-benzofuran-3-carboxylic acid (6-cyanomethoxy-naphthalen-2-yl)-amide. A mixture of 2-butyl-benzofuran-3-carboxylic acid (6-hydroxy-naphthalen-2-yl)-amide (1.00 g, 2.79 mmol), prepared in the previous step, bromoacetonitrile (583 μL, 8.37 mmol) and potassium carbonate (1.93 g, 13.97 mmol) in 25 mL of DMF was stirred under nitrogen at room temperature for 23 h (overnight). The reaction was partitioned between methylene chloride and water. The organic layer was separated, washed four times with water, one time with saturated NaCl, dried (MgSO₄) and the solvent removed under reduced pressure to give 1.27 g of a brown solid. Purification of this solid on a 90 g KP-SIL 60 Å Biotage column using methylene chloride as the eluent gave 2-butyl-benzofuran-3-carboxylic acid (6-cyanomethoxy-naphthalen-2-yl)-amide (778 mg, 70%) as a light yellow solid, mp 122–124° C.

Elemental Analysis for $C_{25}H_{22}N_2O_3$ Calc'd: C, 75.36; H, 5.57; N, 7.03 Found: C, 75.23; H, 5.61; N, 6.95

Step 7: 2-Butyl-benzofuran-3-carboxylic acid [6-(2H-tetrazol-5-ylmethoxy)-naphthalen-2-yl]-amide A mixture of 2-butyl-benzofuran-3-carboxylic acid (6-cyanomethoxy-naphthalen-2-yl)-amide (301 mg, 0.756 mmol), prepared in the previous step, sodium azide (147 mg, 2.25 mmol) and ammonium chloride (121 mg, 2.27 mmol) in 15 mL of DMF was heated under nitrogen at 100° C. for 4 h. The reaction was diluted with water, made basic by the addition of 1N NaOH and extracted five times with ethyl acetate. The aqueous layer was then acidified with 1 N HCl. The solid formed was collected by filtration, rinsed with water and dried under reduced pressure to give the title compound (116 mg, 34%) as an off-white solid, mp 194–198° C.

Elemental Analysis for $C_{25}H_{23}N_5O_3+0.17\ C_3H_7NO$ Calc'd: C, 67.50; H, 5.37; N, 15.95 Found: C, 66.57; H, 5.27; N, 15.88

EXAMPLE 4

{6-[(2-Butyl-benzofuran-3-carbonyl)-amino]-naphthalen-2-yloxy}-acetic acid sodium salt Step 1: {6-[(2-Butyl-benzofuran-3-carbonyl)-amino]-naphthalen-2-yloxy}-acetic acid methyl ester. A mixture of 2-butyl-benzofuran-3-carboxylic acid (6-hydroxy-naphthalen-2-yl)amide (353 mg, 0.983 mmol), prepared in step 5 of Example 3, methyl bromoacetate (93 μL, 0.982 mmol) and potassium carbonate (676 mg, 4.89 mmol) in 15 mL of DMF was stirred under nitrogen at room temperature for 19 h (overnight). The reaction was diluted with ethyl acetate, extracted five times with water, dried (MgSO4) and the solvent removed under reduced pressure to give 416 mg of a yellow solid. Purification of the solid on a 90 g KP-SIL 60 Å Biotage column using methylene chloride as the eluent gave {6-[(2-butyl-benzofuran-3-carbonyl)-amino]-naphthalen-2-yloxy}-acetic acid methyl ester as a white solid, mp 131–133° C.

Elemental Analysis for $C_{26}H_{25}NO_5$ Calc'd: C, 72.37; H, 5.84; N, 3.25 Found: C, 72.32, H, 5.83; N, 3.21

Step 2: {6-[(2-Butyl-benzofuran-3-carbonyl)-amino]-naphthalen-2-yloxy}-acetic acid sodium salt. A mixture of {6-[(2-butyl-benzofuran-3-carbonyl)-amino]-naphthalen-2-yloxy}-acetic acid methyl ester (103 mg, 0.239 mmol), prepared in the previous step, and 1 N NaOH (239 μL, 0.239 mmol) in 10 mL of THF plus 5 mL of water was stirred at room temperature for 21 h (overnight). The solvent was removed under reduced pressure to give the title compound (95 mg, 87%) as a yellow solid, MS m/z: 416 [M−H]⁻.

Elemental Analysis for $C_{25}H_{22}NO_5Na+0.98\ H_2O$ Calc'd: C, 65.69; H, 5.28; N, 3.06 Found: C, 65.17; H, 5.30; N, 2.91

EXAMPLE 5

2-Butyl-benzofuran-3-carboxylic acid [5-bromo-6-(2H-tetrazol-5-ylmethoxy)-naphthalen-2-yl]-amide Step 1: 2-Butyl-benzofuran-3-carboxylic acid (5-bromo-6-hydroxy-naphthalen-2-yl)-amide. Bromine (287 μL, 5.57 mmol) in 50 mL of glacial HOAc was added under nitrogen dropwise over 3 h to a solution of 2-butyl-benzofuran-3-carboxylic acid (6-hydroxy-naphthalen-2-yl)-amide (2.00 g, 5.57 mmol), prepared in step 5 of Example 3, in 100 mL of glacial HOAc at room temperature. After the addition the reaction was stirred at room temperature for 2 h. The solid formed was collected by filtration and dried under reduced pressure to give 1.70 g of an off-white solid. The solid was dissolved in 100 mL of 20% MeOH—CH₂Cl₂ and chromatographed on 750 g of silica gel (230–400 mesh) using methylene chloride as the eluent. 2-Butyl-benzofuran-3-carboxylic acid (5-bromo-6-hydroxy-naphthalen-2-yl)-amide 91.28 g, 52%) was isolated as a light yellow solid, mp 195–197° C.

Elemental Analysis for $C_{23}H_{20}BrNO_3$ Calc'd: C, 63.03; H, 4.60; N, 3.20 Found: C, 62.66; H, 4.39; N, 3.10

Step 2: 2-Butyl-benzofuran-3-carboxylic acid (5-bromo-6-cyanomethoxy-naphthalen-2-yl)-amide. A mixture of 2-butyl-benzofuran-3-carboxylic acid (5-bromo-6-hydroxy-naphthalen-2-yl)-amide (351 mg, 0.801 mmol), prepared in the previous step, bromoacetonitrile (67 μL, 0.962 mmol) and potassium carbonate (559 mg, 4.05 mmol) in 15 mL of DMF was stirred under nitrogen at room temperature for 19 h (overnight). The reaction was partitioned between ethyl acetate and water. The organic layer was separated, washed five times with water, dried (MgSO₄) and the solvent removed under reduced pressure to give 2-butyl-benzofuran-3-carboxylic acid (5-bromo-6-cyanomethoxy-naphthalen-2-yl)-amide (364 mg, 95%) as a yellow solid, mp 155–159° C.

Elemental Analysis for $C_{25}H_{21}BrN_2O_3$ Calc'd: C, 62.90; H, 4.43; N, 5.87 Found: C, 62.72; H, 4.40; N, 5.82

Step 3: 2-Butyl-benzofuran-3-carboxylic acid [5-bromo-6-(2H-tetrazol-5-ylmethoxy)-naphthalen-2-yl]-amide. A mixture of 2-butyl-benzofuran-3-carboxylic acid (5-bromo-6-cyanomethoxy-naphthalen-2-yl)-amide (266 mg, 0.557 mmol), prepared in the previous step, sodium azide (110 mg, 1.69 mmol) and ammonium chloride (90.2 mg, 1.69 mmol) in 15 ml of DMF was stirred under nitrogen at 100° C. for 5 h. The reaction was diluted with water, made basic with 1 N NaOH and extracted five times with ethyl acetate. The ethyl acetate extract was acidified with 1 N HCl, filtered and the solvent concentrated under reduced pressure and then diluted with water. The solid present was collected by filtration, rinsed with water and dried under reduced pressure to give the title compound (210 mg, 72%) as an off-white solid, mp 242–245° C.

Elemental Analysis for $C_{25}H_{22}BrN_5O_3+0.27 H_2O$ Calc'd: C, 57.17; H, 4.33; N, 13.33 Found: C, 56.58; H, 4.26; N, 12.69

EXAMPLE 6

{1-Bromo-6-[(2-butyl-benzofuran-3-carbonyl)-amino]-naphthalen-2-yloxy}-acetic acid sodium salt Step 1: {1-Bromo-6-[(2-butyl-benzofuran-3-carbonyl)-amino]-naphthalen-2-yloxy}-acetic acid methyl ester. In the same manner as described in step 5 of Example 1, and replacing benzofuran-2-carboxylic acid (6-hydroxy-naphthalen-2-ylmethyl)-amide with 2-butyl-benzofuran-3-carboxylic acid (5-bromo-6-hydroxy-naphthalen-2-yl)-amide, prepared in step 1 of Example 5, gave {1-bromo-6-[(2-butyl-benzofuran-3-carbonyl)-amino]-naphthalen-2-yloxy}-acetic acid methyl ester (444 mg, 76%) was isolated as a white solid, mp 179–181° C.

Elemental Analysis for $C_{26}H_{24}BrNO_5$ Calc'd: C, 61.19; H, 4.74; N, 2.74 Found: C, 60.81; H, 4.63; N, 2.79

Step 2: {1-Bromo-6-[(2-butyl-benzofuran-3-carbonyl)-amino]-naphthalen-2-yloxy}-acetic acid sodium salt. In the same manner as described in step 2 of Example 4 and replacing {6-[(2-butyl-benzofuran-3-carbonyl)-amino]-naphthalen-2-yloxy}-acetic acid methyl ester with {1-bromo-6-[(2-butyl-benzofuran-3-carbonyl)-amino]-naphthalen-2-yloxy}-acetic acid methyl ester, prepared in the previous step, gave the title compound (289 mg, 94%) as a tan solid, mp 284–287° C.

Elemental Analysis for $C_{25}H_{21}BrNO_5Na+0.79 H_2O$ Calc'd: C, 56.38; H, 4.27; N, 2.63 Found: C, 56.15; H, 4.16; N, 2.54

EXAMPLE 7

2-{1-Bromo-6-[(2-butyl-benzofuran-3-carbonyl)-amino]-naphthalen-2-yloxy}-3-phenyl-propionic acid Step 1: 2-Hydroxy-3-phenyl-propionic acid methyl ester. Hydrogen chloride was bubbled for 15 minutes into a solution of 2-hydroxy-3-phenyl-propionic acid (10.0 g, 60 mmol) in 100 mL of methanol at room temperature. The vessel was sealed and then stirred overnight at room temperature. The reaction was made basic by the addition of 5% NaHCO$_3$ and then concentrated under reduced pressure to remove the methanol. The residue was diluted with water and extracted with ethyl acetate. The organic layer was extracted with saturated NaCl, dried (MgSO$_4$) and the solvent removed under reduced pressure to give 2-hydroxy-3-phenyl-propionic acid methyl ester (9.7 g, 90%) as a yellow oil, MS m/z 180 [M]$^+$.

Elemental Analysis for $C_{10}H_{12}O_3$ Calc'd: C, 66.65; H, 6.71; N, 0.00 Found: C, 66.52; H, 6.86; N, 0.29

Step 2: 3-Phenyl-2-trifluoromethanesulfonyloxy-propionic acid methyl ester. Triethylamine (931 μL, 6.68 mmol) was added under nitrogen to a solution of 2-hydroxy-3-phenyl-propionic acid methyl ester (1.00 g, 5.57 mmol), prepared in the previous step, in 20 mL of chloroform (99.9%; free of ethanol) at dry ice-acetone temperature. Trifluoromethanesulfonic anhydride (1.03 mL, 6.13 mmol) was then added dropwise over 15 minutes. The cooling bath was removed and the reaction was stirred overnight at room temperature. The reaction was extracted with 1 N HCl, 5% NaHCO$_3$, dried (MgSO$_4$) and the solvent removed under reduced pressure to give 1.53 g a brown oil. Purification of the oil on 100 g of silica gel (230–400 mesh) using 3:1 methylene chloride-hexane as the eluent gave 3-phenyl-2-trifluoromethanesulfonyloxy-propionic acid methyl ester (1.106 g, 64%) as clear oil.

Elemental Analysis for $C_{11}H_{11}F_3O_5S$ Calc'd: C, 42.31; H, 3.55; N, 0.00 Found: C, 42.15; H, 3.35; N, 0.14

Step 3: 2-{1-Bromo-6-[(2-butyl-benzofuran-3-carbonyl)-amino]-naphthalen-2-yloxy}-3-phenyl-propionic acid methyl ester. A mixture of 2-butyl-benzofuran-3-carboxylic acid (5-bromo-6-hydroxy-naphthalen-2-yl) amide (203 mg, 0.463 mmol), prepared in step 1 of Example 5, 3-phenyl-2-trifluoromethanesulfonyloxypropionic acid methyl ester (218 mg, 0.700 mmol), prepared in the previous step, and cesium carbonate (303 mg, 0.929 mmol) in 25 mL of acetone was stirred under nitrogen at room temperature for 21 h (overnight). The acetone was removed under reduced pressure and the residue partitioned between ethyl acetate and water. The organic layer was separated and the aqueous layer extracted two times with ethyl acetate. The combined extracts were dried (MgSO$_4$) and the solvent removed under reduced pressure to give 337 mg of a yellow oil. Purification of the oil on 300 g of silica gel (230–400 mesh) using methylene chloride as the eluent gave 2-{1-bromo-6-[(2-butyl-benzofuran-3-carbonyl)-amino]-naphthalen-2-yloxy}-3-phenyl-propionic acid methyl ester (233 mg, 84%) [P6154-76-1] as an off-white solid, mp 136–139° C.

Elemental Analysis for $C_{33}H_{30}BrNO_5$ Calc'd: C, 66.00; H, 5.04; N, 2.33 Found: C, 66.02; H, 4.92; N, 2.27

Step 4: 2-{1-Bromo-6-[(2-butyl-benzofuran-3-carbonyl)-amino]-naphthalen-2-yloxy}-3-phenyl-propionic acid. A mixture of 2-{1-bromo-6-[(2-butyl-benzofuran-3-carbonyl)-amino]-naphthalen-2-yloxy}-3-phenyl-propionic acid methyl ester (139 mg, 0.231 mmol), prepared in the previous step, and 1 N NaOH (231 μL, 0.231 mmol) in 75 mL of methanol was refluxed for 4 h. By TLC starting material remained. Water (10 mL) and 1 N NaOH (231 μL, 0.231 mmol) were added and the mixture refluxed for 18 h (overnight). The reaction was filtered and 2 mL of 1 N HCL was added to the filtrate. The filtrate was concentrated under reduced pressure to remove the methanol. The solid formed was collected by filtration, rinsed with water and dried under reduced pressure to give the title compound (111 mg, 81%) as a white solid, mp 191–195° C.

Elemental Analysis for $C_{32}H_{28}BrNO_5+0.19 H_2O$ Calc'd: C, 65.16; H, 4.85; N, 2.37 Found: C, 65.36; H, 4.59; N, 2.36

EXAMPLE 8

2-Butyl-benzofuran-3-carboxylic acid [6-(1H-tetrazol-5-ylmethoxy)-naphthalen-2-ylmethyl]-amide sodium salt Step 1: 6-Aminomethyl-naphthalen-2-ol. A mixture of C-(6-methoxy-naphthalen-2-yl)-methylamine (10.78 g, 57.6 mmol), prepared in step 1 of Example 1, and 350 mL of 48%

HBr was refluxed for 3 h. The solvent was removed under reduced pressure give 13.48 g of a dark brown solid. The solid was dissolved in approximately 500 mL of water, made basic by the addition of 5% NaHCO$_3$ and filtered. The filtrate was extracted multiple times with ethyl acetate. The combined organic extracts were dried (MgSO$_4$) and the solvent removed under reduced pressure to give 6-aminomethyl-naphthalen-2-ol (3.4 g, 30%) as an off-white solid, mp 188–192° C.

Elemental Analysis for C$_{11}$H$_{11}$NO0.1 H2O+0.05 EtOAc Calc'd: C, 74.98; H, 6.52; N, 7.81 Found: C, 73.74; H, 6.44; N, 7.50

Step 2: 2-Butyl-benzofuran-3-carboxylic acid (6-hydroxy-naphthalen-2-ylmethyl)-amide. 2-Butyl-benzofuran-3-carbonyl chloride (1.54 g, 6.5 mmol), prepared in step 2 of Example 3, in 45 mL of anhydrous THF was added under nitrogen dropwise over 2 h to a solution of 6-aminomethyl-naphthalen-2-ol (1.13 g, 6.5 mmol), prepared in the previous step, and triethylamine (906 μL, 6.5 mmol) in 150 mL of anhydrous THF at room temperature. After the addition the reaction was stirred at room temperature for 20 h (overnight). The solid was removed by filtration and the filtrate concentrated under reduced pressure to give 2.50 g of a brown oil. Purification of the oil on a 90 g KP-SIL 60 Δ Biotage column using 3:1 hexane:ethyl acetate as the eluent gave 2-butyl-benzofuran-3-carboxylic acid (6-hydroxy-naphthalen-2-ylmethyl)-amide (1.88 g, 78%) as a white solid, mp 155–156° C.

Elemental Analysis for C$_{24}$H$_{23}$NO$_3$ Calc'd: C, 77.19; H, 6.21; N, 3.75 Found: C, 76.99; H, 6.07; N, 3.76

Step 3: 2-Butyl-benzofuran-3-carboxylic acid (6-cyanomethoxy-naphthalen-2-ylmethyl)-amide. A mixture of 2-butyl-benzofuran-3-carboxylic acid (6-hydroxy-naphthalen-2-ylmethyl)-amide (402 mg, 0.974 mmol), prepared in the previous step, bromoacetonitrile (204 μL, 2.9 mmol) and potassium carbonate (673 mg, 4.87 mmol) in 10 mL of DMF was stirred under nitrogen at room temperature for 20 h (overnight). The reaction was diluted with methylene chloride, extracted multiple times with water, dried (MgSO$_4$) and the solvent removed under reduced pressure to give 413 mg of an off-white solid. Recrystallization of the solid from isopropyl alcohol gave 2-butyl-benzofuran-3-carboxylic acid (6-cyanomethoxy-naphthalen-2-ylmethyl)-amide (349 mg, 87%) as a white solid, mp 142–143° C.

Elemental Analysis for C$_{26}$H$_{24}$N$_2$O$_3$ Calc'd: C, 75.71; H, 5.86; N, 6.79 Found: C, 75.66; H, 5.87; N, 6.84

Step 4: 2-Butyl-benzofuran-3-carboxylic acid [6-(1 tetrazol-5-ylmethoxy)-naphthalen-2-ylmethyl]-amide sodium salt. A mixture of 2-butyl-benzofuran-3-carboxylic acid (6-cyanomethoxy-naphthalen-2-ylmethyl)-amide (200 mg, 0.485 mmol), prepared in the previous step, sodium azide (94 mg, 1.45 mmol) and ammonium chloride (77 mg, 1.45 mmol) in 10 mL of DMF was stirred under nitrogen at 100° C. for 5 h. The reaction was diluted with water, made basic by the addition of 1 N NaOH and extracted two times with ethyl acetate. At this point a solid was present in the aqueous layer. The solid was collected by filtration and dried under reduced pressure to give the title compound (134 mg, 54%) as a white solid, mp 207–210° C.

Elemental Analysis for C$_{26}$H$_{24}$N$_5$O$_3$Na+1.87 H2O Calc'd: C, 61.09; H, 5.47; N, 13.70 Found: C, 59.38; H, 5.28; N, 13.38

EXAMPLE 9

Sodium; (6-{[(2-butyl-benzofuran-3-carbonyl)-amino]-methyl}-naphthalen-2-yloxy)-acetate Step 1: (6-{[(2-Butyl-benzofuran-3-carbonyl)-amino]-methyl}-naphthalen-2-yloxy)-acetic acid methyl ester. A mixture of 2-butyl-benzofuran-3-carboxylic acid (6-hydroxy-naphthalen-2-ylmethyl)-amide (500 mg, 1.34 mmol), prepared in step 2 of Example 8, methyl bromoacetate (127 μL, 1.34 mmol) and potassium carbonate (926 mg, 6.7 mmol) in 25 mL of DMF was stirred under nitrogen at room temperature overnight. The reaction was diluted with ethyl acetate, extracted multiple times with water, dried (MgSO$_4$) and the solvent removed under reduced pressure to give 573 mg of a tan solid. Recrystallization of the solid from isopropyl alcohol gave (6-{[(2-butyl-benzofuran-3-carbonyl)-amino]-methyl}-naphthalen-2-yloxy)-acetic acid methyl ester (411 mg, 69%) as a white solid, mp 142–143° C.

Elemental Analysis for C$_{27}$H$_{27}$NO$_5$ Calc'd: C, 72.79; H, 6.11; N, 3.14 Found: C, 72.61; H, 6.13; N, 3.13

Step 2: Sodium; (6-{[(2-butyl-benzofuran-3-carbonyl)-amino]-methyl}-naphthalen-2-yloxy)-acetate. 1 N NaOH (449 μL, 0.449 mmol) was added to a solution of (6-{[(2-butyl-benzofuran-3-carbonyl)-amino]-methyl}-naphthalen-2-yloxy)-acetic acid methyl ester (200 mg, 0.449 mmol), prepared in the previous step, in 30 mL of THF plus 15 mL of water at room temperature. After the addition the reaction was stirred at room temperature overnight. The solvent was removed under reduced pressure to give the title compound (209 mg, 99%) as a white solid, mp >275° C., MS m/z 430 [M–H]$^-$.

Elemental Analysis for C$_{26}$H$_{25}$NO$_5$Na+1.2 H$_2$O Calc'd: C, 65.59; H, 5.80; N, 2.94 Found: C, 65.24; H, 5.58; N, 2.91

EXAMPLE 10

[6-({[5-(4-Chloro-phenyl)-2-methyl-furan-3-carbonyl]-amino}-methyl)-naphthalen-2-yloxy]-acetic acid Step 1: 5-(4-Chloro-phenyl)-2-methyl-furan-3-carboxylic acid (6-hydroxy-naphthalen-2-ylmethyl)-amide. 5-(4-Chloro-phenyl)-2-methyl-furan-3-carbonyl chloride (737 mg, 2.89 mmol) in 25 mL of methylene chloride was added under nitrogen dropwise over 30 minutes to a suspension of 6-aminomethyl-naphthalen-2-ol (500 mg, 2.89 mmol), prepared in step 1 of Example 8, in 25 mL of anhydrous pyridine at ice bath temperature. After the addition the ice bath was removed and the reaction stirred at room temperature overnight. The reaction was partitioned between methylene chloride and 1 N HCl. The organic layer was separated and the aqueous layer was extracted with methylene chloride. The combined extracts were dried (MgSO$_4$) and the solvent removed under reduced pressure to give 1.04 g of a brown solid. Purification of the solid on 500 g of silica gel (230–400 mesh) using 10% ethyl acetate-methylene chloride as the eluent gave 5-(4-chloro-phenyl)-2-methyl-furan-3-carboxylic acid (6-hydroxy-naphthalen-2-ylmethyl)-amide (507 mg, 45%) as a tan solid, mp 202–204° C.

Elemental Analysis for C$_{23}$H$_{18}$ClNO$_3$ Calc'd: C, 70.50; H, 4.63; N, 3.57 Found: C, 69.25; H, 4.67; N, 3.49

Step 2: [6-({[5-(4-Chloro-phenyl)-2-methyl-furan-3-carbonyl]-amino}-methyl)-naphthalen-2-yloxy]-acetic acid methyl ester. A mixture of 5-(4-chloro-phenyl)-2-methyl-furan-3-carboxylic acid (6-hydroxy-naphthalen-2-ylmethyl)-amide (405 mg, 1.03 mmol), prepared in the previous step, methyl bromoacetate (98 μL, 1.03 mmol) and potassium carbonate (710 mg, 5.15 mmol) in 10 mL of DMF was stirred under nitrogen at room temperature overnight. The reaction was diluted with ethyl acetate, extracted multiple times with water, one time with saturated NaCl, dried (MgSO$_4$) and the solvent removed under reduced pressure to give 450 mg of a yellow solid. Recrystallization of the solid from isopropyl alcohol gave [6-({[5-(4-chloro-phenyl)-2-methyl-furan-3-carbonyl]-amino}-methyl)-naphthalen-2-yloxy]-acetic acid methyl ester (280 mg, 58%) as an off-white solid, mp 168–169° C.

Elemental Analysis for $C_{26}H_{22}ClNO_5$ Calc'd: C, 67.32; H, 4.78; N, 3.02 Found: C, 66.86; H, 4.69; N, 2.98

Step 3: [6-({[5-(4-Chloro-phenyl)-2-methyl-furan-3-carbonyl]-amino}-methyl)-naphthalen-2-yloxy]-acetic acid. 1 N NaOH (514 μL, 0.514 mmol) was added under nitrogen to a solution of [6-({[5-(4-chloro-phenyl)-2-methyl-furan-3-carbonyl]-amino}-methyl)-naphthalen-2-yloxy]-acetic acid methyl ester (239 mg, 0.514 mmol), prepared in the previous step, in 30 mL of THF plus 15 mL of water. After the addition the reaction was stirred at room temperature for 20 h (overnight). 1 N HCl (1 mL) was added and the reaction then concentrated under reduced pressure to remove the THF. The solid present was removed by filtration and dried under reduced pressure to give the title compound (190 mg, 83%) as a tan solid, mp 177–181° C.

Elemental Analysis for $C_{25}H_{20}ClNO_5+0.34$ $H_2O$ Calc'd: C, 65.85; H, 4.57; N, 3.07 Found: C, 65.74; H, 4.82; N, 2.84

EXAMPLE 11

[6-({[5-(4-Chloro-phenyl)-2-trifluoromethyl-furan-3-carbonyl]-amino}-methyl)-naphthalen-2-yloxy]-acetic acid Step 1: 5-(4-Chloro-phenyl)-2-trifluoromethyl-furan-3-carboxylic acid (6-hydroxy-naphthalen-2-ylmethyl)-amide. In the same manner as described in step 1 of Example 10, and replacing 5-(4-chloro-phenyl)-2-methyl-furan-3-carbonyl chloride with 5-(4-chloro-phenyl)-2-trifluoromethyl-furan-3-carbonyl chloride, gave 5-(4-chloro-phenyl)-2-trifluoromethyl-furan-3-carboxylic acid (6-hydroxy-naphthalen-2-ylmethyl)-amide (691 mg, 32%) as a tan powder, mp 189–191° C.

Elemental Analysis for $C_{23}H_{15}ClF_3NO_3+0.39$ $CH_2Cl_2$ Calc'd: C, 58.66; H, 3.32; N, 2.92 Found: C, 57,76; H, 3.09; N. 2.79

Step 2: [6-({[5-(4-Chloro-phenyl)-2-trifluoromethyl-furan-3-carbonyl]-amino}-methyl)-naphthalen-2-yloxy]-acetic acid methyl ester. A mixture of 5-(4-chloro-phenyl)-2-trifluoromethyl-furan-3-carboxylic acid (6-hydroxy-naphthalen-2-ylmethyl)-amide (300 mg, 0.67 mmol), prepared in the previous step, methyl bromoacetate (64 μL, 0.67 mmol) and potassium carbonate (465 mg, 3.37 mmol) in 10 mL of DMF was stirred under nitrogen at room temperature overnight. The reaction was diluted with ethyl acetate, extracted multiple times with water, dried (MgSO₄) and the solvent removed under reduced pressure to give 284 mg of a yellow solid. Recrystallization of this solid from isopropyl alcohol gave [6-({[5-(4-chloro-phenyl)-2-trifluoromethyl-furan-3-carbonyl]-amino}-methyl)-naphthalen-2-yloxy]-acetic acid methyl ester (204 mg, 59%) as a white solid, mp 182–183° C.

Elemental Analysis for $C_{26}H_{19}ClF_3NO_5$ Calc'd: C, 60.30; H, 3.70; N, 2.70 Found: C, 60.09; H, 3.52; N, 2.69

Step 3: [6-({[5-(4-Chloro-phenyl)-2-trifluoromethyl-furan-3-carbonyl]-amino}-methyl)-naphthalen-2-yloxy]-acetic acid. 1 N NaOH (324 μL, 0.32 mmol) was added under nitrogen to a solution at room temperature of [6-({[5-(4-chloro-phenyl)-2-trifluoromethyl-furan-3-carbonyl]-amino}-methyl)-naphthalen-2-yloxy]-acetic acid methyl ester (140 mg, 0.27 mmol), prepared in the previous step, in 15 mL of THF plus 8 mL of water. After the addition the reaction was stirred at room temperature for 7 h. The reaction was acidified with 1 N HCl and then concentrated under reduced pressure to remove the THF. The solid present was collected by filtration and dried under reduced pressure to give the title compound (125 mg, 91%) as an off-white solid, mp 194–196° C.

Elemental Analysis for $C_{25}H_{17}ClF_3NO_5+0.4$ $H_2O$ Calc'd: C, 58.75; H, 3.51; N, 2.74 Found: C, 58.83; H, 3.59; N, 2.56

EXAMPLE 12

(6-{[(1-phenyl-5-propyl-1H-pyrazole-4-carbonyl)-amino]-methyl}-naphthalen-2-yloxy)-acetic acid Step 1: 1-Phenyl-5-propyl-1H-pyrazole-4-carboxylic acid (6-hydroxy-naphthalen-2-ylmethyl)-amide. 1-Phenyl-5-propyl-1H-pyrazole-4-carbonyl chloride (2.0 g, 8.0 mmol) in 20 mL of methylene chloride was added under nitrogen at room temperature to a suspension of 6-aminomethyl-naphthalen-2-ol (1.63 g, 9.42 mmol), prepared in step 1 of Example 8, in 75 mL of anhydrous pyridine. After the addition the reaction was stirred at room temperature for 17 h (overnight). The reaction was partitioned between methylene chloride and 1 N HCl. The organic layer was separated and the aqueous layer extracted multiple times with methylene chloride. The combined extracts were dried (MgSO₄) and the solvent removed under reduced pressure to give 1.9 g of a brown solid. Recrystallization of the solid one time from ethyl acetate and one time from isopropyl alcohol gave 1-phenyl-5-propyl-1H-pyrazole-4-carboxylic acid (6-hydroxy-naphthalen-2-ylmethyl)-amide (767 mg, 25%) as a tan solid, mp 189–190° C.

Elemental Analysis for $C_{24}H_{23}N_3O_2$ Calc'd: C, 74.78; H, 6.01; N, 10.90 Found: C, 73.64; H, 5.78; N, 10.77

Step 2: (6-{[(1-Phenyl-5-propyl-1H-pyrazole-4-carbonyl)-amino]-methyl}-naphthalen-2-yloxy)-acetic acid methyl ester. A mixture of 1-phenyl-5-propyl-1H-pyrazole-4-carboxylic acid (6-hydroxy-naphthalen-2-ylmethyl)-amide (300 mg, 0.778 mmol), prepared in the previous step, methyl bromoacetate (74 μL, 0.778 mmol) and potassium carbonate (540 mg, 3.89 mmol) in 10 mL of DMF was stirred under nitrogen at room temperature for 18 h (overnight). The reaction was diluted with ethyl acetate, extracted multiple times with water, one time with saturated NaCl, dried (MgSO₄) and the solvent removed under reduced pressure to give 299 mg of an off-white solid. Recrystallization of the solid from isopropyl alcohol gave (6-{[(1-phenyl-5-propyl-1H-pyrazole-4-carbonyl)-amino]-methyl}-naphthalen-2-yloxy)-acetic acid methyl ester (208 mg, 57%) as a white solid, mp 145–146° C.

Elemental Analysis for $C_{27}H_{27}N_3O_4$ Calc'd: C, 70.88; H, 5.95; N, 9.18 Found: C, 70.73; H, 5.76; N, 9.15

Step 3: (6-{[(1-phenyl-5-propyl-1H-pyrazole-4-carbonyl)-amino]-methyl}-naphthalen-2-yloxy)-acetic acid. 1 N NaOH (431 μL, 0.431 mmol) was added under nitrogen to a solution at room temperature of (6-{[(1-phenyl-5-propyl-1H-pyrazole-4-carbonyl)-amino]-methyl}-naphthalen-2-yloxy)-acetic acid methyl ester (170 mg, 0.359 mmol), prepared in the previous step, in 25 mL of MeOH plus 10 mL of water. After the addition the reaction was stirred at room temperature for 18 h (overnight). The reaction was acidified with 1 N HCl and then concentrated under reduced pressure to remove the MeOH. The solid present was collected by filtration and dried under reduced pressure to give the title compound (146 mg, 92%) as an off-white solid, mp 175–177° C.

Elemental Analysis for $C_{26}H_{25}N_3O_4+0.25$ $H_2O$ Calc'd: C, 69.71; H, 5.74; N, 9.38 Found: C, 68.99; H, 5.73; N, 9.20

EXAMPLE 13

[6-({[1-(4-Chloro-phenyl)-5-propyl-1H-pyrazole-4-carbonyl]-amino}-methyl)-naphthalen-2-yloxy]-acetic acid Step 1: (6-Hydroxy-naphthalen-2-ylmethyl)-carbamic acid tert-butyl ester. A solution of di-tert-butyl dicarbonate (3.13 g, 14.36 mmol) in 25 mL of anhydrous DMF was added dropwise under nitrogen over 30 minutes to a mixture of 6-hydroxy-naphthalen-2-ylmethyl-ammonium; bromide (3.65 g, 14.36 mmol), prepared in step 2 of Example 1, and triethylamine (2.0 mL, 14.36 mmol) in 75 mL of anhydrous DMF. The reaction was stirred at room temperature for 18 h (overnight). The reaction was diluted with ethyl acetate and extracted two times with 1N HCl and four times with water. The organic layer was dried ($MgSO_4$) and the solvent removed under reduced pressure to give an oily brown solid. Purification of the material on a 90 g KP-SIL 60Å Biotage column using 3% ethyl acetate in methylene chloride as the eluent gave (6-hydroxy-naphthalen-2-ylmethyl)-carbamic acid tert-butyl ester (917 mg, 23%) as a yellow solid, mp 173–174° C.

Elemental Analysis for $C_{16}H_{19}NO_3$ Calc'd: C, 70.31; H, 7.01; N, 5.12 Found: C, 69.36; H, 7.08; N, 5.08

Step 2: [6-tert-Butoxycarbonylamino-methyl)-naphthalen-2-yloxy]-acetic acid methyl ester. A mixture of (6-hydroxy-naphthalen-2-ylmethyl)-carbamic acid tert-butyl ester (5.127 g, 18.77 mmol), methyl bromoacetate (1.78 mL, 18.77 mmol) and potassium carbonate (13.0 g, 93.85 mmol) in 100 mL of DMF was stirred under nitrogen at room temperature for 17 h (overnight). The reaction was diluted with ethyl acetate, extracted four times with water, dried ($MgSO_4$) and the solvent removed under reduced pressure to give a yellow solid. Recrystallization of the solid from isopropyl alcohol gave [6-tert-butoxycarbonylamino-methyl)-naphthalen-2-yloxy]-acetic acid methyl ester (1.8 g, 28%) as a white solid, mp 182–183° C.

Elemental Analysis for $C_{26}H_{19}ClF_3NO_5$ Calc'd: C, 60.30; H, 3.70; N, 2.70 Found: C, 60.09; H, 3.52; N, 2.69

Step 3: 6-Methoxycarbonyl-methoxy-naphthalen-2-ylmethyl-ammonium; chloride. A solution of 75 mL of ethyl acetate saturated with hydrogen chloride gas was added under nitrogen to [6-tert-butoxycarbonylamino-methyl)-naphthalen-2-yloxy]-acetic acid methyl ester (1.01 g, 2.924 mmol), prepared in the previous step. Within one minute a solid precipitated from solution. The reaction stirred for 18 h (overnight). The solid was collected by filtration, rinsed with ethyl acetate and dried under reduced pressure to give 6-methoxycarbonyl-methoxy-naphthalen-2-ylmethyl-ammonium; chloride (0.79 g, 95.8%) as an off white solid, mp 240–241° C.

Elemental Analysis for $C_{14}H_{16}ClNO_3$+0.02 mol $H_2O$ Calc'd: C, 59.61; H, 5.73; N, 4.79 Found: C, 59.04; H, 5.72; N, 4.82

Step 4: [6-({[1-(4-Chloro-phenyl)-5-propyl-1H-pyrazole-4-carbonyl]-amino}-methyl)-naphthalen-2-yloxy]-acetic acid methyl ester. Triethylamine (300 µL, 2.13 mmol) was added under nitrogen to a suspension of 6-methoxycarbonylmethoxy-naphthalen-2-ylmethyl-ammonium; chloride (300 mg, 1.06 mmol), prepared in the previous step, and 1-(4-chloro-phenyl)-5-propyl-1H-pyrazole-4-carbonyl chloride (301 mg, 1.06 mmol) in 20 mL of methylene chloride at room temperature. After the addition the reaction was stirred at room temperature overnight. The reaction was diluted with methylene chloride and then extracted with water, 5% $NaHCO_3$, dried ($MgSO_4$) and the solvent removed under reduced pressure to give 480 mg of an off-white solid. Recrystallization of the solid from ethyl acetate gave [6-({[1-(4-chloro-phenyl)-5-propyl-1H-pyrazole-4-carbonyl]-amino}-methyl)-naphthalen-2-yloxy]-acetic acid methyl ester (397 mg, 76%) as a white solid, mp 139–140° C.

Elemental Analysis for $C_{27}H_{26}ClN_3O_4$ Calc'd: C, 65.92; H, 5.33; N, 8.54 Found: C, 65.74; H, 5.14; N, 8.51

Step 5: [6-({[1-(4-Chloro-phenyl)-5-propyl-1H-pyrazole-4-carbonyl]-amino}-methyl)-naphthalen-2-yloxy]-acetic acid. 1 N NaOH (335 µL, 0.335 mmol) was added under nitrogen to a solution of [6-({[1-(4-chloro-phenyl)-5-propyl-1H-pyrazole-4-carbonyl]-amino}-methyl)-naphthalen-2-yloxy]-acetic acid methyl ester (150 mg, 0.305 mmol), prepared in the previous step, in 25 mL of MeOH plus 10 mL of water at room temperature. After the addition the reaction was stirred at room temperature for 20 h (overnight). The reaction was acidified by the addition of 1 N HCl and then concentrated under reduced pressure to remove the MeOH. The solid present was collected by filtration and dried under reduced pressure to give the title compound (138 mg, 94%) as a pink solid, mp 203–204° C.

Elemental Analysis for $C_{26}H_{24}N_3O_4Cl$+0.22 $H_2O$+0.26 $CH_3OH$ Calc'd: C, 64.34; H, 5.24; N, 8.57 Found: C, 64.03; H, 4.94; N, 8.51

EXAMPLE 14

[6-({[1-(4-Chloro-phenyl)-5-trifluoromethyl-1H-pyrazole-4-carbonyl]-amino}-methyl)-naphthalen-2-yloxy]-acetic acid Step 1: [6-({[1-(4-Chloro-phenyl)-5-trifluoromethyl-1H-pyrazole-4-carbonyl]-amino}-methyl)-naphthalen-2-yloxy]-acetic acid methyl ester. Triethylamine (300 µL, 2.13 mmol) was added under nitrogen to a suspension of 6-methoxycarbonylmethoxy-naphthalen-2-ylmethyl-ammonium; chloride (300 mg, 1.06 mmol), prepared in step 3 of Example 13, and 1-(4-chloro-phenyl)-5-trifluoromethyl-1H-pyrazole-4-carbonyl chloride (330 mg, 1.06 mmol) in 20 mL of methylene chloride at room temperature. After the addition the reaction was stirred at room temperature overnight. The reaction was diluted with methylene chloride and then extracted with water, 5% $NaHCO_3$, dried ($MgSO_4$) and the solvent removed under reduced pressure to give 518 mg of a brown solid. Recrystallization of the solid from isopropyl alcohol gave [6-({[1-(4-chloro-phenyl)-5-trifluoromethyl-1H-pyrazole-4-carbonyl]-amino}-methyl)-naphthalen-2-yloxy]-acetic acid methyl ester (479 mg, 87%) as a tan solid, mp 174–176° C.

Elemental Analysis for $C_{25}H_{19}ClF_3N_3O_4$ Calc'd: C, 57.98; H, 3.70; N, 8.11 Found: C, 57.95; H, 3.66; N, 8.15

Step 2: [6-({[1-(4-Chloro-phenyl)-5-trifluoromethyl-1H-pyrazole-4-carbonyl]-amino}-methyl)-naphthalen-2-yloxy]-acetic acid. 1 N NaOH (563 µL, 0.563 mmol) was added under nitrogen to [6-({[1-(4-chloro-phenyl)-5-trifluoromethyl-1H-pyrazole-4-carbonyl]-amino}-methyl)-naphthalen-2-yloxy]-acetic acid methyl ester (243 mg, 0.469 mmol), prepared in the previous step, in 100 mL of MeOH plus 25 mL of water at room temperature. After the addition the reaction was stirred at room temperature overnight. The reaction was acidified by the addition of 1 N HCl and then concentrated under reduced pressure to remove the MeOH. The solid present was collected by filtration and dried under reduced pressure to give the title compound (210 mg, 89%) as a pink solid, mp 189–191° C.

Elemental Analysis for $C_{24}H_{17}ClF_3N_3O_4$+0.68 $H_2O$ Calc'd: C, 55.85; H, 3.59; N, 8.14 Found: C, 55.52; H, 3.23; N, 8.05

EXAMPLE 15

(1-Bromo-6-{[(1-phenyl-5-propyl-1H-pyrazole-4-carbonyl)-amino]-methyl}-naphthalen-2-yloxy)-acetic acid Step 1: (5-Bromo-6-hydroxy-naphthalen-2-ylmethyl)-carbamic acid tert-butyl ester. A solution of benzyltrimethylammoniumbromide (1.755 g, 4.5 mmol) in 50 mL of methylene chloride was added dropwise under nitrogen over 2 h to a mixture of (6-hydroxy-naphthalen-2-ylmethyl)-carbamic acid tert-butyl ester (1.24 g, 4.5 mmol), prepared in step 1 of Example 13, and calcium carbonate (1.35 g, 13.5 mmol) in 150 mL of methylene chloride plus 60 mL of methanol at room temperature. The reaction was stirred for 20 h (overnight). The reaction was diluted with water and extracted three times with methylene chloride. The organic extracts were combined, dried ($MgSO_4$) and the solvent removed under reduced pressure to give 1.4 g of a yellow solid. The solid was recrystallized from 15 mL of isopropyl alcohol. The crystals were collected by filtration and dried under reduced pressure to give (5-bromo-6-hydroxy-naphthalen-2-ylmethyl)-carbamic acid tert-butyl ester (0.95 g, 60%) as an off white solid, mp 150–152° C.

Elemental Analysis for $C_{16}H_{18}BrNO_3$ Calc'd: C, 54,56; H, 5.15; N, 3.98 Found: C, 54.22; H, 4.84; N, 3.82

Step 2: [1-Bromo-6-(tert-butoxycarbonylamino-methyl)-naphthalen-2-yloxy]-acetic acid methyl ester. A mixture of (5-bromo-6-hydroxy-naphthalen-2-ylmethyl)-carbamic acid tert-butyl ester (0.89 g, 2.5 mmol), prepared in the previous step, potassium carbonate (1.7 g, 12.5 mmol), and methyl bromoacetate (1.26 mL, 2.75 mmol) in 10 mL of DMF was stirred under nitrogen for 18 h (overnight). The reaction was diluted with ethyl acetate and extracted three times with water. The organic layer was dried ($MgSO_4$) and the solvent removed under reduced pressure to give [1-bromo-6-(tert-butoxycarbonylamino-methyl)-naphthalen-2-yloxy]-acetic acid methyl ester (1.016 g, 96%) as an off white solid, mp 96–100° C.

Elemental Analysis for $C_{19}H_{22}BrNO_5$ Calc'd: C, 53.79; H, 5.23; N, 3.30 Found: C, 53.86; H, 5.24; N, 3.27

Step 3: 5-Bromo-6-methoxycarbonylmethoxy-naphthalen-2-ylmethyl-ammonium; chloride. A solution of 75 mL of ethyl acetate saturated with hydrogen chloride gas was added under nitrogen at room temperature to [1-bromo-6-(tert-butoxycarbonylamino-methyl)-naphthalen-2-yloxy]-acetic acid methyl ester (0.934 g, 2.2 mmol), prepared in the previous step. A precipitate formed within one minute. The reaction stirred for 17 h (overnight). The solid was collected by filtration, rinsed with ethyl acetate, and dried under reduced pressure to give 5-bromo-6-methoxycarbonylmethoxy-naphthalen-2-ylmethyl-ammonium; chloride (0.696 g, 88%) as an off white solid, mp 261–263° C.

Elemental Analysis for $C_{14}H_{14}BrNO_3$+HCl Calc'd: C, 46.63; H, 4.19; N, 3.88 Found: C, 46.41; H, 4.01; N, 3.82

Step 4: (1-Bromo-6-{[(1-phenyl-5-propyl-1H-pyrazole-4-carbonyl)-amino]-methyl}-naphthalen-2-yloxy)-acetic acid methyl ester. Triethylamine (0.192 mL, 1.38 mmol) was added under nitrogen to a mixture of 5-bromo-6-methoxycarbonylmethoxy-naphthalen-2-ylmethyl-ammonium; chloride (0.25 g, 0.69 mmol), prepared in the previous step, and 1-phenyl-5-propyl-1H-pyrazole-4-carbonyl chloride (0.17 g, 0.69 mmol) in 20 mL of methylene chloride at room temperature. The reaction stirred under nitrogen for 17 h. The reaction was diluted with methylene chloride, extracted two times with water, two times with 5% sodium bicarbonate, dried ($MgSO_4$) and the solvent removed under reduced pressure to give (1-Bromo-6-{[(1-phenyl-5-propyl-1H-pyrazole-4-carbonyl)-amino]-methyl}-naphthalen-2-yloxy)-acetic acid methyl ester (0.347 g, 95%) as a white solid, mp 144–146° C.

Elemental Analysis for $C_{27}H_{26}BrN_3O_4$ Calc'd: C, 60.46; H, 4.89; N, 7.83 Found: C, 60.74; H, 4.60; N, 7.80

Step 5: (1-Bromo-6-{[(1-phenyl-5-propyl-1H-pyrazole-4-carbonyl)-amino]-methyl}-naphthalen-2-yloxy)-acetic acid. A mixture of (1-bromo-6-{[(1-phenyl-5-propyl-1H-pyrazole-4-carbonyl)-amino]-methyl}-naphthalen-2-yloxy)-acetic acid methyl ester (0.20 g, 0.373 mmol), prepared in the previous step, 1N NaOH (373 μL, 0.373 mmol), 5 mL of water and 60 mL of methanol was stirred at room temperature for 20 h. Starting material was present by TLC. An additional 186 μL (0.186 mmol) of 1N NaOH was added and the reaction stirred at room temperature for 18 h. The reaction was filtered to remove trace solids and acidified with 1N HCl until pH 1 by litmus paper. The methanol was removed under reduced pressure. The solid formed was collected by filtration and dried under reduced pressure to give the title compound (0.13 g, 67%) as an off-white solid, mp 140–145° C.

Elemental Analysis for $C_{26}H_{24}BrN_3O_4$+0.71 $H_2O$ Calc'd: C, 58.35; H, 4.79; N, 7.85 Found: C, 58.05; H, 4.58; N, 7.63

EXAMPLE 16

[1-Bromo-6-({[1-(4-chloro-phenyl)-5-trifluoromethyl-1H-pyrazole-4-carbonyl]-amino}-methyl)-naphthalen-2-yloxy]-acetic acid Step 1: [1-Bromo-6-({[1-(4-chloro-phenyl)-5-trifluoromethyl-1H-pyrazole-4-carbonyl]-amino}-methyl)-naphthalen-2-yloxy]-acetic acid methyl ester. In the same manner as described in step 4 of Example 15 [1-bromo-6-({[1-(4-chloro-phenyl)-5-trifluoromethyl-1H-pyrazole-4-carbonyl]-amino}-methyl)-naphthalen-2-yloxy]-acetic acid methyl ester (0.25 g, 61%) was isolated as an off-white solid, mp 206–207° C.

Elemental Analysis for $C_{25}H_{18}BrClF_3N_3O_4$ Calc'd: C, 50.32; H, 3.04; N, 7.04 Found: C, 50.30; H, 2.76; N, 6.74

Step 2: [1-Bromo-6-({[1-(4-chloro-phenyl)-5-trifluoromethyl-1H-pyrazole-4-carbonyl]-amino}-methyl)-naphthalen-2-yloxy]-acetic acid. A mixture of [1-bromo-6-({[1-(4-chloro-phenyl)-5-trifluoromethyl-1H-pyrazole-4-carbonyl]-amino}-methyl)-naphthalen-2-yloxy]-acetic acid methyl ester (0.175 g, 0.29 mmol), prepared in the previous step, 1N NaOH (323 μL, 0.323 mmol), 2 mL of $H_2O$ and 100 mL of methanol was warmed until all solids had gone into solution. When the reaction cooled a solid precipitated. After the reaction had stirred for 17 h (overnight) a solid was still present. Another 162 μL (0.162 mmol) of 1N NaOH was added. The reaction stirred for 18 h. The reaction was filtered to remove any trace particles and acidified with 1N HCl until pH 1 by litmus paper. The methanol was removed under reduced pressure. The solid formed was collected by filtration and dried under reduced pressure to give the title compound (0.14 g, 8.3%) as a white solid, mp 245° C.

Elemental Analysis for $C_{24}H_{16}ClBrF_3N_3O_4$+0.29 mol $H_2O$ Calc'd: C, 49.03; H, 2.84; N, 7.15 Found: C, 48.85; H, 2.48; N, 7.23

EXAMPLE 17

2-Butyl-benzofuran-3-carboxylic acid [5-bromo-6-(1H-tetrazol-5-ylmethoxy)-naphthalen-2-ylmethyl]-amide sodium salt Step 1: 2-Butyl-benzofuran-3-carboxylic acid (5-bromo-6-hydroxy-naphthalen-2-ylmethyl)-amide. Bromine (210

μL, 4.02 mmol) in 50 mL of glacial HOAc was added under nitrogen dropwise over 2 h to a solution of 2-butyl-benzofuran-3-carboxylic acid (6-hydroxy-naphthalen-2-ylmethyl)-amide (1.5 g, 4.02 mmol), prepared in step 2 of Example 8, in 300 mL of glacial HOAc at room temperature. After the addition the reaction was stirred at room temperature for 20 h (overnight). The solid formed was collected by filtration and dried under reduced pressure to give 2-butyl-benzofuran-3-carboxylic acid (5-bromo-6-hydroxy-naphthalen-2-ylmethyl)-amide (1.41 g, 81%) as a light gray solid, mp 192–193° C.

Elemental Analysis for $C_{24}H_{22}BrNO_3$ Calc'd: C, 63.73; H, 4.90; N, 3.10 Found: C, 62.59; H, 4.74; N, 3.00

Step 2: 2-Butyl-benzofuran-3-carboxylic acid (5-bromo-6-cyanomethoxy-naphthalen-2-ylmethyl)-amide. A mixture of 2-butyl-benzofuran-3-carboxylic acid (5-bromo-6-hydroxy-naphthalen-2-ylmethyl)-amide (300 mg, 0.66 mmol), prepared in the previous step, bromoacetonitrile (56 μL, 0.80 mmol) and potassium carbonate (460 mg, 3.32 mmol) in 15 mL of DMF was stirred under nitrogen at room temperature for 18 h (overnight). The reaction was diluted with ethyl acetate, extracted multiple times with water, dried ($MgSO_4$) and the solvent removed under reduced pressure to give 2-butyl-benzofuran-3-carboxylic acid (5-bromo-6-cyanomethoxy-naphthalen-2-ylmethyl)-amide (324 mg, 99%) as an off-white solid, mp154–157° C.

Elemental Analysis for $C_{26}H_{23}BrN_2O_3$ Calc'd: C, 63.55; H, 4.72; N, 5.70 Found: C, 62.95; H, 4.57; N, 5.86

Step 3: 2-Butyl-benzofuran-3-carboxylic acid [5-bromo-6-(1H-tetrazol-5-ylmethoxy)-naphthalen-2-ylmethyl]-amide sodium salt. A mixture of 2-butyl-benzofuran-3-carboxylic acid (5-bromo-6-cyanomethoxy-naphthalen-2-ylmethyl)-amide (200 mg, 0.41 mmol), sodium azide (80 mg, 1.22 mmol) and ammonium chloride (65 mg, 1.22 mmol) in 10 mL of DMF was stirred under nitrogen at 100° C. for 4 h. By TLC starting material remained. An additional 80 mg of sodium azide and 65 mg of ammonium chloride were added and the reaction stirred at 100° C. for 4 h. The reaction was diluted with ethyl acetate, made basic by the addition of 1 N NaOH and partitioned with water. The organic layer was separated and the aqueous layer extracted three times with ethyl acetate. By TLC most of the material was in the ethyl acetate extracts. The extracts were washed multiple times with water, dried ($MgSO_4$) and the solvent removed under reduced pressure to give the title compound (143 mg, 61%) as an off-white solid, mp 214–215° C.

Elemental Analysis for $C_{26}H_{24}BrN_5O_3Na+0.52\ H_2O$ Calc'd: C, 55.20; H, 4.28; N, 12.38 Found: C, 56.62; H, 4.65; N, 12.71

EXAMPLE 18

2-(1-Bromo-6-{[(2-butyl-benzofuran-3-carbonyl)-amino]-methyl}-naphthalen-2-yloxy)-3-phenyl-propionic acid Step 1: 2-(1-Bromo-6-{[(2-butyl-benzofuran-3-carbonyl)-amino]-methyl}-naphthalen-2-yloxy)-3-phenyl-propionic acid methyl ester. 2-Hydroxy-3-phenyl-propionic acid methyl ester (200 mg, 1.1 mmol), prepared in step 1 of Example 7, in 5 mL of anhydrous THF was added under nitrogen to a solution of 2-butyl-benzofuran-3-carboxylic acid (5-bromo-6-hydroxy-naphthalen-2-ylmethyl)-amide (500 mg, 1.1 mmol), prepared in step 1 of Example 17, in 5 mL of anhydrous THF at room temperature. Triphenylphosphine (433 mg, 1.65 mmol) was then added. Diethyl azodicarboxylate (260 μL, 1.65 mmol) in 5 mL of anhydrous THF was added to the mixture at ice-bath temperature dropwise over 5 minutes. After the addition the reaction was stirred at ice-bath temperature for 15 minutes and then at room temperature for 17 h. The solvent was removed under reduced pressure and the residue partitioned between ethyl acetate and water. The organic layer was separated and the aqueous layer extracted three times with ethyl acetate. The combined extracts were dried ($MgSO_4$) and the solvent removed under reduced pressure to give 1.36 g of an off-white solid. Purification of the solid by chromatography on silica gel using methylene chloride as the eluent gave 2-(1-bromo-6-{[(2-butyl-benzofuran-3-carbonyl)-amino]-methyl}-naphthalen-2-yloxy)-3-phenyl-propionic acid methyl ester as a white solid, mp 110–112° C.

Elemental Analysis for $C_{34}H_{32}BrNO_5$ Calc'd: C, 66.45; H, 5.25; N, 2.28 Found: C, 66.19; H, 5.01; N, 2.19

Step 2: 2-(1-Bromo-6-{[(2-butyl-benzofuran-3-carbonyl)-amino]-methyl}-naphthalen-2-yloxy)-3-phenyl-propionic acid. 1 N Sodium hydroxide (220 μL, 0.22 mmol) was added under nitrogen to a solution of 2-(1-bromo-6-{[(2-butyl-benzofuran-3-carbonyl)-amino]-methyl}-naphthalen-2-yloxy)-3-phenyl-propionic acid methyl ester (107 mg, 0.17 mmol), prepared in the previous step, in 40 mL of methanol plus 10 mL of water at room temperature. After the addition the reaction was stirred at room temperature overnight. By TLC starting material remained. Additional quantities of 1 N NaOH were added until the reaction was complete by TLC. The reaction was acidified by the addition of 1 N HCl and then concentrated under reduced pressure to remove the methanol. The solid formed was collected by filtration and dried under reduced pressure to give the title compound (61 mg, 58%) as a white solid, mp 125–130° C.

Elemental Analysis for $C_{33}H_{30}BrNO_5+0.25\ H_2O$ Calc'd: C, 65.51; H, 5.08; N, 2.32 Found: C, 65.51; H, 4.97; N, 2.22

EXAMPLE 19

Sodium; (1-bromo-6-{[(2-butyl-benzofuran-3-carbonyl)-amino]-methyl}-naphthalen-2-yloxy)-acetate Step 1: (1-Bromo-6-{[(2-butyl-benzofuran-3-carbonyl)-amino]-methyl}-naphthalen-2-yloxy)-acetic acid methyl ester. A mixture of 2-butyl-benzofuran-3-carboxylic acid (5-bromo-6-hydroxy-naphthalen-2-ylmethyl)-amide (450 mg, 0.99 mmol), prepared in step 2 of Example 17, methyl bromoacetate (90 μL, 0.99 mmol) and potassium carbonate (690 mg, 5 mmol) in 10 mL of DMF was stirred under nitrogen at room temperature overnight. The reaction was diluted with ethyl acetate, extracted multiple times with water, dried ($MgSO_4$) and the solvent removed under reduced pressure to give 472 mg of a yellow solid. Recrystallization of the solid from isopropyl alcohol gave (1-bromo-6-{[(2-butyl-benzofuran-3-carbonyl)-amino]-methyl}-naphthalen-2-yloxy)-acetic acid methyl ester (352 mg, 68%) as an off-white solid, mp 140–141° C.

Elemental Analysis for $C_{27}H_{26}BrNO_5$ Calc'd: C, 61.84; H, 5.00; N, 2.67 Found: C, 61.34; H, 4.79; N, 2.63

Step 2: Sodium; (1-bromo-6-{[(2-butyl-benzofuran-3-carbonyl)-amino]-methyl}-naphthalen-2-yloxy)-acetate. 1 N NaOH (477 μL, 0.477 mmol) was added to a solution of (1-bromo-6-{[(2-butyl-benzofuran-3-carbonyl)-amino]-methyl}-naphthalen-2-yloxy)-acetic acid methyl ester (250 mg, 0.477 mmol), prepared in the previous step, in 30 mL of THF plus 15 mL of water at room temperature. After the addition the reaction was stirred at room temperature overnight. The solvent was removed under reduced pressure to give the title compound (200 mg, 75%) as a white solid, mp 260° C.

Elemental Analysis for $C_{26}H_{23}BrN_5O_5Na+1.4H_2O$ Calc'd: C, 56.01; H, 4.66; N, 2.51 Found: C, 55.63; N, 4.66; N, 2.47

EXAMPLE 20

2-Methyl-benzofuran-3-carboxylic acid [5-bromo-6-(1H-tetrazol-5-ylmethoxy)-naphthalen-2-ylmethyl]-amide Step 1: 2-Methyl-benzofuran-3-carboxylic acid. In the same manner as described in step 1 of Example 3, 2-methyl-benzofuran-3-carboxylic acid (4.24 g, 34%) was isolated as a yellow solid, mp 171–176° C.

Elemental Analysis for $C_{10}H_{83}$ Calc'd: C, 68.18; H, 4.58; N, 0.00 Found: C, 67.50; H, 4.43; N, 0.22

Step 2: 2-Methyl-benzofuran-3-carbonyl chloride. In the same manner as described in step 2 of Example 3, 2-methyl-benzofuran-3-carbonyl chloride was isolated as a dark brown solid. Without additional purification it was immediately used in step 3.

Step 3: 2-Methyl-benzofuran-3-carboxylic acid (6-hydroxy-naphthalen-2-ylmethyl)-amide. 2-Methyl-benzofuran-3-carbonyl chloride, prepared in the previous step, in 50 mL of anhydrous THF was added under nitrogen dropwise over 1.5 h to a solution of 6-aminomethyl-naphthalen-2-ol (1.00 g, 5.79 mmol), prepared in step 1 of Example 8, and triethylamine (811 µL, 5.82 mmol) in 300 mL of anhydrous THF at room temperature. After the addition the reaction was stirred at room temperature for 19 h (overnight). The solvent was removed under reduced pressure. The dark brown residue was partitioned between 400 mL of 20% MeOH in methylene chloride and 1 N HCl. After separating the organic layer, the aqueous layer was extracted three times with 20% MeOH in methylene chloride. The combined extracts were dried (MgSO$_4$) and the solvent removed under reduced pressure to give 1.59 g of a brown solid. The solid was taken up in 50 mL of boiling ethyl acetate, filtered, concentrated to a volume of 25 mL and diluted with 75 mL of hexane. The solid formed was collected by filtration and dried under reduced pressure to give 2-methyl-benzofuran-3-carboxylic acid (6-hydroxy-naphthalen-2-ylmethyl)-amide (606 mg, 32%) as a brown solid, mp 195–198° C.

Elemental Analysis for $C_{21}H_{17}NO_3$ Calc'd: C, 76.12; H, 5.17; N, 4.23 Found: C, 74.62; H, 4.95; N, 3.84

Step 4: 2-Methyl-benzofuran-3-carboxylic acid (5-bromo-6-hydroxy-naphthalen-2-ylmethyl)-amide. Bromine (83 µL, 1.61 mmol) in 15 mL of glacial HOAc was added under nitrogen dropwise over 3 h to a solution of 2-methyl-benzofuran-3-carboxylic acid (6-hydroxy-naphthalen-2-ylmethyl)-amide (537 mg, 1.62 mmol), prepared in the previous step, in 60 mL of glacial HOAc at room temperature. After the addition the reaction was stirred at room temperature for 1 h. The solvent was removed under reduced pressure and the residue partitioned between 20% MeOH in methylene chloride and 5% NaHCO$_3$. After separating the organic layer the aqueous layer was extracted three times with 20% MeOH in methylene chloride. The combined extracts were dried (MgSO$_4$) and the solvent removed under reduced pressure to give 2-methyl-benzofuran-3-carboxylic acid (5-bromo-6-hydroxy-naphthalen-2-ylmethyl)-amide (690 mg, 100%) as a brown solid, mp 179–181° C.

Elemental Analysis for $C_{21}H_{16}BrNO_3$ Calc'd: C, 61.48; H, 3.93; N, 3.41 Found: C, 57.06; H, 3.78; N, 3.07

Step 5: 2-Methyl-benzofuran-3-carboxylic acid (5-bromo-6-cyanomethoxy-naphthalen-2-ylmethyl)-amide. A mixture of 2-methyl-benzofuran-3-carboxylic acid (5-bromo-6-hydroxy-naphthalen-2-ylmethyl)-amide (401 mg, 0.98 mmol), prepared in the previous step, bromoacetonitrile (82 µL, 1.18 mmol) and potassium carbonate (674 mg, 4.88 mmol) in 20 mL of DMF was stirred under nitrogen at room temperature for 12 h (overnight). The reaction was partitioned between ethyl acetate and water. The organic layer was separated, extracted multiple times with water, dried (MgSO$_4$) and the solvent removed under reduced pressure to give 386 mg of a brown solid. Purification of the solid on 100 g of silica gel (230–400 mesh) using 1% to 4% ethyl acetate in methylene chloride as the eluent gave 2-methyl-benzofuran-3-carboxylic acid (5-bromo-6-cyanomethoxy-naphthalen-2-ylmethyl)-amide (330 mg, 75%) as a light yellow solid, mp 180–182° C.

Elemental Analysis for $C_{23}H_{17}BrN_2O_3$ Calc'd: C, 61.48; H, 3.81; N, 6.23 Found: C, 60.09; H, 3.63; N, 6.09

Step 6: 2-Methyl-benzofuran-3-carboxylic acid [5-bromo-6-(1H-tetrazol-5-ylmethoxy)-naphthalen-2-ylmethyl]-amide. A mixture of 2-methyl-benzofuran-3-carboxylic acid (5-bromo-6-cyanomethoxy-naphthalen-2-ylmethyl)-amide (233 mg, 0.52 mmol), prepared in the previous step, sodium azide (101 mg, 1.56 mmol) and ammonium chloride (83 mg, 1.55 mmol) in 15 mL of DMF was stirred under nitrogen at 100° C. for 8 h. The reaction was diluted with 35 mL of water, made basic by the addition of 3 mL of 1 N NaOH and extracted five times with ethyl acetate. The aqueous layer was acidified by the addition of 5 mL of 1 N HCl. The solid that precipitated was collected by filtration and dried under reduced pressure to give the title compound (216 mg, 85%) as a white solid, mp 242–244° C.

Elemental Analysis for $C_{23}H_{18}BrN_5O_3+0.09 H_2O$ Calc'd: C, 55.93; H, 3.71; N, 14.18 Found: C, 55.66; H, 3.54; N, 13.99

EXAMPLE 21

2-Ethyl-benzofuran-3-carboxylic acid [5-bromo-6-(1H-tetrazol-5-yl methoxy)-naphthalen-2-yl methyl]-amide Step 1: 2-Ethyl-benzofuran-3-carboxylic acid. In the same manner as described in step 1 of Example 3, 2-ethyl-benzofuran-3-carboxylic acid (11.69 g, 54%) was isolated as a brown solid, mp 102–106° C.

Elemental Analysis for $C_{11}H_{10}O_3$ Calc'd: C, 69.46; H, 5.30; N, 0.00 Found: C, 69.20; H, 5.13; N, -0.16

Step 2: 2-Ethyl-benzofuran-3-carbonyl chloride. In the same manner as described in step 2 of Example 3, 2-ethyl-benzofuran-3-carbonyl chloride was isolated as a brown oil. Without additional purification it was immediately used in step 3.

Step 3: 2-Ethyl-benzofuran-3-carboxylic acid (6-hydroxy-naphthalen-2-ylmethyl)-amide. In the same manner as described in step 3 of Example 20, 2-ethyl-benzofuran-3-carboxylic acid (6-hydroxy-naphthalen-2-ylmethyl)-amide (899 mg, 45%) was isolated as a light brown solid, mp 203–205° C.

Elemental Analysis for $C_{22}H_{19}NO_3$ Calc'd: C, 76.50; H, 5.54; N, 4.06 Found: C, 75.83; H, 5.61; N, 4.04

Step 4: 2-Ethyl-benzofuran-3-carboxylic acid (5-bromo-6-hydroxy-naphthalen-2-ylmethyl)-amide. In the same manner as described in step 4 of Example 20, 2-ethyl-benzofuran-3-carboxylic acid (5-bromo-6-hydroxynaphthalen-2-ylmethyl)-amide (365 mg, 31%) was isolated, after recrystallization from ethyl acetate, as a light brown solid, mp 188–190° C.

Elemental Analysis for $C_{22}H_{18}BrNO_3$ Calc'd: C, 62.28; H, 4.28; H, 3.30 Found: C, 61.75; H, 3.91; N, 3.25

Step 5: 2-Ethyl-benzofuran-3-carboxylic acid (5-bromo-6-cyanomethoxy-naphthalen-2-ylmethyl)-amide. In the same manner as described in step 5 of Example 20, 2-ethyl-benzofuran-3-carboxylic acid (5-bromo-6-cyanomethoxy-naphthalen-2-ylmethyl)-amide (328 mg, 100%) was isolated as a tan solid, mp 181–183° C.

Elemental Analysis for $C_{24}H_{19}BrN_2O_3$ Calc'd: C, 62.22; H, 4.13; N, 6.05 Found: C, 61.30; H, 3.97; N, 5.92

Step 6: 2-Ethyl-benzofuran-3-carboxylic acid [5-bromo-6-(1H-tetrazol-5-ylmethoxy)-naphthalen-2-ylmethyl]-amide. In the same manner as described in step 6 of Example 20, the title compound was isolated as an off-white solid, mp 235–238° C.

Elemental Analysis for $C_{24}H_{20}BrN_5O_3$ Calc'd: C, 56.85; H, 3.99; N, 13.81 Found: C, 56.45; H, 3.74; N, 13.73

EXAMPLE 22

1-Phenyl-5-propyl-1H-pyrazole-4-carboxylic acid [5-bromo-6-(1H-tetrazol-5-ylmethoxy)-naphthalen-2-ylmethyl]-amide Step 1: 1-Phenyl-5-propyl-1H-pyrazole-4-carboxylic acid (6-hydroxy-naphthalen-2-ylmethyl)-amide. A solution of 1-phenyl-5-propyl-1H-pyrazole-4-carbonyl chloride (2.0 g, 8 mmol) in 20 mL of methylene chloride was added dropwise under nitrogen to a mixture of 6-aminomethyl-naphthalen-2-ol (1.63 g, 9.42 mmol), prepared in step 1 of Example 8, and 75 mL of anhydrous pyridine. The reaction stirred at room temperature for 17 h (overnight). The reaction was diluted with methylene chloride and extracted with 1N HCl. The aqueous layer was separated and extracted with methylene chloride. The organic extracts were combined, dried (MgSO$_4$) and the solvent removed under reduced pressure to give a brown solid. The solid was recrystallized from ethyl acetate and then again from isopropanol. The crystals were collected by filtration and dried under reduced pressure to give 1-phenyl-5-propyl-1H-pyrazole-4-carboxylic acid (6-hydroxy-naphthalen-2-ylmethyl)-amide (0.767 g, 25%) as a tan solid, mp 189–190° C.

Elemental Analysis for $C_{24}H_{23}N_3O_2$ Calc'd: C, 74.78; H, 6.01; N, 10.90 Found: C, 73.64; H, 5.78; N, 10.77

Step 2: 4-[(5-Bromo-6-hydroxy-naphthalen-2-ylmethyl)-carbamoyl]-2-phenyl-3-propyl-2H-pyrazol-1-ium; bromide. A solution of bromine (0.05 mL, 0.978 mmol) in 25 mL of glacial acetic acid was added dropwise under nitrogen over 2 h to a solution of 1-phenyl-5-propyl-1H-pyrazole-4-carboxylic acid (6-hydroxy-naphthalen-2-ylmethyl)-amide (0.377 g, 0.978 mmol), prepared in the previous step, in 100 mL of glacial acetic acid. The reaction stirred for 17 h (overnight). An orange solid, which precipitated from solution, was collected by filtration and rinsed with glacial acetic acid. The solid was dried under reduced pressure to give 4-[(5-bromo-6-hydroxy-naphthalen-2-ylmethyl)-carbamoyl]-2-phenyl-3-propyl-2H-pyrazol-1-ium; bromide (0.4431 g, 82%) as a light brown solid, mp 198–200° C.

Elemental Analysis for $C_{24}H_{22}BrN_3O_2$+HBr+0.25 $H_2O$ Calc'd: C, 52.43; H, 4.31; N, 7.64 Found: C, 51.61; H, 4.04; N, 7.42

Step 3: 1-Phenyl-5-propyl-1H-pyrazole-4-carboxylic acid (5-bromo-6-cyanomethoxy-naphthalen-2-ylmethyl)-amide. A mixture of 4-[(5-bromo-6-hydroxy-naphthalen-2-ylmethyl)-carbamoyl]-2-phenyl-3-propyl-2H-pyrazol-1-ium; bromide (0.30 g, 0.646 mmol), prepared in the previous step, bromoacetonitrile (0.054 mL, 0.775 mmol), potassium carbonate (0.446 g, 3.23 mmol) and 10 mL of DMF was stirred under nitrogen at room temperature overnight. The reaction was diluted with ethyl acetate and extracted multiple times with water and with a saturated sodium chloride solution. The organic layer was separated, dried (MgSO$_4$), and the solvent removed under reduced pressure to give a brown oil. The oil was chromatographed on a 90 g KP-SIL 60 Å Biotage column using 15% ethyl acetate in methylene chloride as the eluent. All fractions containing product were combined and the solvent removed under reduced pressure to give 1-phenyl-5-propyl-1H-pyrazole-4-carboxylic acid (5-bromo-6-cyanomethoxy-naphthalen-2-ylmethyl)-amide (0.196 g, 60%) as a light yellow solid, mp 175–176° C.

Elemental Analysis for $C_{26}H_{23}BrN_4O_2$ Calc'd: C, 62.04; H, 4.61; N, 11.13 Found: C, 62.03; H, 4.47; N, 11.00

Step 4: 1-Phenyl-5-propyl-1H-pyrazole-4-carboxylic acid [5-bromo-6-(1H-tetrazol-5-ylmethoxy)-naphthalen-2-ylmethyl]-amide. A mixture of 1-phenyl-5-propyl-1H-pyrazole-4-carboxylic acid (5-bromo-6-cyanomethoxy-naphthalen-2-ylmethyl)-amide (0.15 g, 0.3 mmol), prepared in the previous step, sodium azide (0.059 g, 0.9 mmol), ammonium chloride (0.048 g, 0.9 mmol) and 10 mL of DMF was stirred at 100° C. for 1.5 h. By TLC starting material remained. Additional sodium azide (0.059 g, 0.9 mmol) and ammonium chloride (0.048 g, 0.9 mmol) were added and the reaction stirred at 100° C. for 2 h. Again by TLC starting material remained. Additional sodium azide (0.059 g, 0.9 mmol) and ammonium chloride (0.048 g, 0.9 mmol) were added and the reaction stirred at 100° C. for 5 h. The reaction was diluted with water and extracted four times with ethyl acetate. The organic layers were combined and acidified with ~3 mL 1N HCl. The mixture was swirled for one minute and then the solution was dried (MgSO$_4$) and filtered. The solvent was removed under reduced pressure and the resulting residue was taken up in 20 mL of water. The solid that formed was collected by filtration and dried under reduced pressure to give the title compound (0.107 g, 65%) as a tan solid, mp 219–220° C.

Elemental Analysis for $C_{26}H_{24}BrN_7O_2$+0.01 $H_2O$ Calc'd: C, 56.96; H, 4.45; N, 17.88 Found: C, 57.12; H, 4.45; N, 17.61

EXAMPLE 23

2-Butyl-benzofuran-3-carboxylic acid [6-(1H-tetrazol-5-ylmethoxy)-5-p-tolyl-naphthalen-2-ylmethyl]-amide Step 1: 2-Butyl-benzofuran-3-carboxylic acid (6-Hydroxy-5-p-tolyl-naphthalen-2-ylmethyl)-amide. A mixture of 2-butyl-benzofuran-3-carboxylic acid (5-bromo-6-hydroxy-naphthalen-2-ylmethyl)-amide (759 mg, 1.68 mmol), prepared in step 1 of Example 17, 4-methylphenylboronic acid (342 mg, 2.52 mmol) and potassium carbonate (471 mg, 3.40 mmol) in 90 mL of dimethoxyethane plus 10 mL of water was heated to 50° C. while being purged with nitrogen. After 30 minutes dichloro[1,1' bis(diphenylphosphino)ferrocene]palladium (II) dichloromethane (147 mg, 0.18 mmol) was added and the reaction heated to 70° C. After 3 h starting material remained. An additional 349 mg (2.57 mmol) of 4-methylphenylboronic acid and 150 mg (0.18 mmol) of dichloro[1,1'-bis(diphenylphosphino)ferrocene]palladium (II) dichloromethane were added and the mixture stirred at 70° C. for 2 h. This process was repeated until no more starting material remained. The reaction was concentrated under reduced pressure to remove the dimethoxyethane and the residue partitioned between methylene chloride and water. The organic layer was separated, extracted multiple times with water, dried ($MgSO_4$) and the solvent removed under reduced pressure to give 1.297 g of material. Purification of the material on a 90 g KP-SIL 60 Å Biotage column using methylene chloride as the eluent gave 2-butyl-benzofuran-3-carboxylic acid (6-hydroxy-5-p-tolyl-naphthalen-2-ylmethyl)-amide (521 mg, 67%) as a white solid, mp 103–105° C.

Elemental Analysis for $C_{31}H_{29}NO_3$ Calc'd: C, 80.32; H, 6.31; N, 3.02 Found: C, 79.81; H, 6.09; N, 2.88

Step 2: 2-Butyl-benzofuran-3-carboxylic acid (6-cyanomethoxy-5-p-tolyl-naphthalen-2-ylmethyl)-amide. A mixture of 2-butyl-benzofuran-3-carboxylic acid (6-hydroxy-5-p-tolyl-naphthalen-2-ylmethyl)-amide (252 mg, 0.54 mmol), prepared in the previous step, bromoacetonitrile (55 µL, 0.81 mmol) and potassium carbonate (378 mg, 2.73 mmol) in 15 mL of DMF was stirred under nitrogen at room temperature for 19 h (overnight). The reaction was diluted with ethyl acetate, extracted multiple times with water, dried ($MgSO_4$) and the solvent removed under reduced presure to give 2-butyl-benzofuran-3-carboxylic acid (6-cyanomethoxy-5-p-tolyl-naphthalen-2-ylmethyl)-amide (269 mg, 99%) as a light brown solid, mp 114–117° C.

Elemental Analysis for $C_{33}H_{30}N_2O_3$ Calc'd: C, 78.86; H, 6.02; N, 5.57 Found: C, 77.91; H, 6.08; N, 5.45

Step 3: 2-Butyl-benzofuran-3-carboxylic acid [6-(1H-tetrazol-5-ylmethoxy)-5-p-tolyl-naphthalen-2-ylmethyl]-amide. A mixture of 2-butyl-benzofuran-3-carboxylic acid (6-cyanomethoxy-5-p-tolyl-naphthalen-2-ylmethyl)-amide (182 mg, 0.36 mmol), prepared in the previous step, sodium azide (77.6 mg, 1.19 mmol) and ammonium chloride (102 mg, 1.90 mmol) in 10 mL of DMF was stirred under nitrogen at 100° C. for 21 h (overnight). If starting material remains additional sodium azide and ammonium chloride are added and the stirring continued at 100° C. until the reaction is complete. The reaction was diluted with water, made basic by the addition of 1 N NaOH and extracted multiple times with ethyl acetate. The ethyl acetate extracts were combined, acidified with 1 N HCl and then concentrated under reduced pressure. The solid present was collected by filtration and dried under reduced pressure to give the title compound (130 mg, 66%) as a white solid, mp 162–166° C.

Elemental Analysis for $C_{33}H_{31}N_5O_3+0.03\ H_2O$ Calc'd: C, 72.57; H, 5.73; N, 12.82 Found: C, 72.19; H, 5.66; N, 12.54

EXAMPLE 24

2-Butyl-benzofuran-3-carboxylic acid [5-phenyl-6-(1H-tetrazol-5-ylmethoxy)-naphthalen-2-ylmethyl]-amide Step 1: 2-Butyl-benzofuran-3-carboxylic acid (6-hydroxy-5-phenyl-naphthalen-2-ylmethyl)-amide. In the same manner as described in step 1 of Example 23, 2-butyl-benzofuran-3-carboxylic acid (6-hydroxy-5-phenyl-naphthalen-2-ylmethyl)-amide (532 mg, 54%) was obtained as a white solid, mp 72–72° C.

Elemental Analysis for $C_{30}H_{27}NO_3$ Calc'd: C, 80.15; H, 6.05; N, 3.12 Found: C, 79.00; H, 6.40; N, 2.92

Step 2: 2-Butyl-benzofuran-3-carboxylic acid (6-cyanomethoxy-5-phenyl-naphthalen-2-ylmethyl)-amide. A mixture of 2-butyl-benzofuran-3-carboxylic acid (6-hydroxy-5-phenyl-naphthalen-2-ylmethyl)-amide (366 mg, 0.813 mmol), prepared in the previous step, bromoacetonitrile (68 µL, 0.976 mmol) and potassium carbonate (562 mg, 4.07 mmol) in 20 mL of DMF was stirred under nitrogen at room temperature for 23 h (overnight). The reaction was diluted with ethyl acetate, extracted multiple times with water, dried ($MgSO_4$) and the solvent removed under reduced pressure to give a brown solid. Purification of the solid on 20 g of silica gel (230–400 mesh) using hexane-ethyl acetate as the eluent gave 2-butyl-benzofuran-3-carboxylic acid (6-cyanomethoxy-5-phenyl-naphthalen-2-ylmethyl)-amide (342 mg, 86%) as a light brown solid, mp 135–138° C.

Elemental analysis for $C_{32}H_{28}N_2O_3$ Calc'd: C, 78.67; H, 5.78; N, 5.73 Found: C, 77.54; H, 5.98; N, 5.63

Step 3: 2-Butyl-benzofuran-3-carboxylic acid [5-phenyl-6-(1H-tetrazol-5-ylmethoxy)-naphthalen-2-ylmethyl]-amide. In the same manner as described in step 3 of Example 23, the title compound (124 mg, 46%) was isolated as a white solid, mp 192–196° C.

Elemental Analysis for $C_{32}H_{29}N_5O_3.0,1H_2O$ Calc'd: C, 72.05; H, 5.52; N, 13.13 Found: C, 71.63; H, 5.54; N, 12.76

EXAMPLE 25

2-Butyl-benzofuran-3-carboxylic [5-(4-methoxy phenyl)-6-(1H-tetrazol-5-ylmethoxy)-naphthalen-2-ylmethyl]-amide, sodium salt Step 1: 2-Butyl-benzofuran-3-carboxylic acid [6-hydroxy-5-(4-methoxy-phenyl)-naphthalen-2-ylmethyl]-amide. In the same manner as described in step 1 of Example 23, 2-butyl-benzofuran-3-carboxylic acid [6-hydroxy-5-(4-methoxy-phenyl)-naphthalen-2-ylmethyl]-amide (529 mg, 50%) was obtained as a white solid, mp 118–122° C.

Elemental Analysis for $C_{31}H_{29}NO_4$ Calc'd: C, 77.64; H, 6.10; N, 2.92 Found: C, 77.18; H, 6.11; N, 2.76

Step 2: 2-Butyl-benzofuran-3-carboxylic acid [6-cyanomethoxy-5-(4-methoxy-phenyl)-naphthalen-2-ylmethyl]-amide. A mixture of 2-butyl-benzofuran-3-carboxylic acid [6-hydroxy-5-(4-methoxy-phenyl)-naphthalen-2-ylmethyl]-amide (301 mg, 0.63 mmol), prepared in the previous step, bromoacetonitrile (52 µL, 0.75 mmol) and potassium carbonate (434 mg, 3.14 mmol) in 20 mL of DMF was stirred under nitrogen at room temperature for 21 h (overnight). The reaction was diluted with ethyl acetate, extracted multiple times with water, dried ($MgSO_4$) and the solvent removed under reduced pressure to give 2-butyl-benzofuran-3-carboxylic acid [6-cyanomethoxy-5-(4-methoxy-phenyl)-naphthalen-2-ylmethyl]-amide (325 mg, 99%) as a brown solid, mp 139–142° C.

Elemental Analysis for $C_{33}H_{30}N_2O_4$ Calc'd: C, 76.43; H, 5.83; N, 5.40 Found: C, 75.34; H, 5.76; N, 5.86

Step 3: 2-Butyl-benzofuran-3-carboxylic [5-(4-methoxy phenyl)-6-(1H-tetrazol-5-ylmethoxy)-naphthalen-2-ylmethyl]-amide, sodium salt. A mixture of 2-butyl-benzofuran-3-carboxylic acid [6-cyanomethoxy-5-(4-methoxy-phenyl)-naphthalen-2-ylmethyl]-amide (207 mg, 0.40 mmol), prepared in the previous step, sodium azide (81 mg, 1.25 mmol) and ammonium chloride (63.5 mg, 1.19 mmol) in 10 mL of DMF was stirred under nitrogen at 100° C. for 6.5 h. If starting material remains additional sodium azide and ammonium chloride are added and the stirring continued at 100° C. until the reaction is complete. The reaction was diluted with 75 mL of water. The solid that formed was collected by filtration and dried under reduced pressure to give the title compound (116 mg, 51%) as an off-white solid, mp 147–152° C.

Elemental Analysis for $C_{33}H_{31}N_5O_4Na+0.71\ H_2O$ Calc'd: C, 66.46; H, 5.31; N, 11.74 Found: C, 67.86; H, 5.50; N, 12.08

EXAMPLE 26

2-Butyl-benzofuran-3-carboxylic acid [5-(4-chloro-phenyl)-6-(1-tetrazol-5-ylmethoxy)-naphthalen-2-ylmethyl]-amide Step 1: 2-Butyl-benzofuran-3-carboxylic acid [5-(4-chloro-phenyl)-6-hydroxy-naphthalen-2-ylmethyl]-amide. In the same manner as described in step 1 of Example 23, 2-butyl-benzofuran-3-carboxylic acid [5-(4-chloro-phenyl)-6-hydroxy-naphthalen-2-ylmethyl]-amide (556 mg, 52%) was obtained as a white solid, mp 122–124° C.

Elemental Analysis for $C_{30}H_{26}ClNO_3$ Calc'd: C, 74.45; H, 5.41; N, 2.89 Found: C, 74.25; H, 5.32; N, 2.89

Step 2: 2-Butyl-benzofuran-3-carboxylic acid [5-(4-chloro-phenyl)-6-cyanomethoxy-naphthalen-2-ylmethyl]-amide. A mixture of 2-butyl-benzofuran-3-carboxylic acid [5-(4-chloro-phenyl)-6-hydroxy-naphthalen-2-ylmethyl]-amide (258 mg, 0.53 mmol), prepared in the previous step, bromoacetonitrile (44 µL, 0.63 mmol) and potassium carbonate (362 mg, 2.62 mmol) in 20 mL of DMF was stirred under nitrogen at room temperature for for 48 h. By TLC starting material remained. Additional 20 µL aliquots of bromoacetonitrile were added until the reaction was complete. The reaction was diluted with ethyl acetate, extracted multiple times with water, dried (MgSO₄) and the solvent removed under reduced pressure to give 257 mg of a brown solid. Purification of the solid on a 90 g KP-SIL 60 Å Biotage column using methylene chloride as the eluent produce a solid material which was recrystallized from isopropyl alcohol to give 2-butyl-benzofuran-3-carboxylic acid [5-(4-chloro-phenyl)-6-cyanomethoxy-naphthalen-2-ylmethyl]-amide (101 mg, 36%) as a white solid, mp 154–158° C.

Elemental Analysis for $C_{32}H_{27}ClN_2O_3$ Calc'd: C, 73.49; H, 5.20; N, 5.36 Found: C, 73.42; H, 5.09; N, 5.31

Step 3: 2-Butyl-benzofuran-3-carboxylic acid [5-(4-chloro-phenyl)-6-(1H-tetrazol-5-ylmethoxy)-naphthalen-2-ylmethyl]-amide. A mixture of 2-butyl-benzofuran-3-carboxylic acid [5-(4-chloro-phenyl)-6-cyanomethoxy-naphthalen-2-ylmethyl]-amide (152 mg, 0.29 mmol), prepared in the previous step, sodium azide (59 mg, 0.90 mmol) and ammonium chloride (85 mg, 1.58 mmol) in 10 mL of DMF was stirred under nitrogen at 100° C. for 24 h (overnight). If starting material remains additional sodium azide and ammonium chloride are added and the stirring continued at 100° C. until the reaction is complete. The reaction was diluted with 50 mL of water, made basic by the addition of 1 N NaOH and extracted multiple times with ethyl acetate. The aqueous layer was acidified. The solid that formed was collected by filtration and dried under reduced pressure to give the title compound (149 mg, 91%) as a white solid, mp 208–211° C.

Elemental Analysis for $C_{32}H_{28}ClN_5O_3+0.19\ H_2O$ Calc'd: C, 67.49; H, 5.02; N, 12.30 Found: C, 67.90; H, 4.99; N, 12.37

EXAMPLE 27

2-Butyl-benzofuran-3-carboxylic acid [5-(4-tert-butyl-phenyl)-6-(1H-tetrazol-5-ylmethoxy)-naphthalen-2-ylmethyl]-amide Step 1: 2-Butyl-benzofuran-3-carboxylic acid [5-(4-tert-butyl-phenyl)-6-hydroxy-naphthalen-2-ylmethyl]-amide. In the same manner as described in step 1 of Example 23, 2-butyl-benzofuran-3-carboxylic acid [5-(4-tert-butyl-phenyl)-6-hydroxy-naphthalen-2-ylmethyl]-amide (525 mg, 47%) was obtained as a white solid, mp 195–197° C.

Elemental Analysis for $C_{34}H_{35}NO_3$ Calc'd: C, 80.76; H, 6.98; N, 2.77 Found: C, 80.26; H, 7.15; N, 2.78

Step 2: 2-Butyl-benzofuran-3-carboxylic acid [5-(4-tert-butyl-phenyl)-6-cyanomethoxy-naphthalen-2-ylmethyl]-amide. A mixture of 2-butyl-benzofuran-3-carboxylic acid [5-(4-tert-butyl-phenyl)-6-hydroxy-naphthalen-2-ylmethyl]-amide (400 mg, 0.79 mmol), prepared in the previous step, bromoacetonitrile (66 µL, 0.95 mmol) and potassium carbonate (547 mg, 3.96 mmol) in 20 mL of DMF was stirred under nitrogen at room temperature for 19 h (overnight). The reaction was diluted with ethyl acetate, extracted multiple times with water, dried (MgSO₄) and the solvent removed under reduced pressure to give a light brown solid. Purification of the solid on a 40 g KP-SIL 60 Å Biotage column gave 2-butyl-benzofuran-3-carboxylic acid [5-(4-tert-butyl-phenyl)-6-cyanomethoxy-naphthalen-2-ylmethyl]-amide (262 mg, 63%) as a white solid, mp 162–164° C.

Elemental Analysis for $C_{36}H_{36}N_2O_3$ Calc'd: C, 79.38; H, 6,66; N, 5.14 Found: C, 78.69; H, 6.72; N, 5.09

Step 3: 2-Butyl-benzofuran-3-carboxylic acid [5-(4-tert-butyl-phenyl)-6-(1H-tetrazol-5-ylmethoxy)-naphthalen-2-ylmethyl]-amide. A mixture of 2-butyl-benzofuran-3-carboxylic acid [5-(4-tert-butyl-phenyl)-6-cyanomethoxy-naphthalen-2-ylmethyl]-amide (207 mg, 0.38 mmol), prepared in the previous step, sodium azide (72.9 mg, 1.12 mmol) and ammonium chloride (58,7 mg, 1.10 mmol) in 10 mL of DMF was stirred under nitrogen at 100° C. for 6 h. If starting material remains additional quantities of sodium azide and ammonium chloride are added until the reaction is complete by TLC. The reaction was diluted with water, made basic by the addition of 1 N NaOH and extracted multiple times with ethyl acetate. The combined organic extracts were acidified by the addition of 1 N HCl and then concentrated under reduced pressure. The residue was diluted with water and the solid that formed was collected by filtration and dried under reduced pressure to give the title compound (186 mg, 84%) as a white solid, mp75–78° C.

Elemental Analysis for $C_{36}H_{37}N_5O_3+0.31\ H_2O$ Calc'd: C, 72.88; H, 6.39; N, 11.80 Found: C, 71.52; H, 6.58; N, 11.83

EXAMPLE 28

(6-{[(2-Butyl-benzofuran-3-carbonyl)-amino]-methyl}-1-phenyl-naphthanen-2-yloxy)-acetic acid Step 1: (6-{[(2-Butyl-benzofuran-3-carbonyl)-amino]-methyl}-1-phenyl-naphthanen-2-yloxy)-acetic acid. A mixture of 2-butyl-benzofuran-3-carboxylic acid (6-hydroxy-5-phenyl-naphthalen-2-ylmethyl)-amide (63 mg, 0.14 mmol), prepared in step 1 of Example 24, methyl bromoacetate (16 µL, 0.17 mmol) and potassium carbonate (100 mg, 0.70 mmol) in 3 mL of DMF was stirred under nitrogen at room temperature for 18 h (overnight). The reaction was diluted with ethyl acetate, extracted multiple times with water, one time with saturated NaCl, dried (MgSO₄) and the solvent removed under reduced pressure to give 81 mg of an off-white solid. Purification of the solid on 100 g of silica gel (230–400 mesh) using 2:1 hexane:ethyl acetate as the eluent gave 52 mg of a white solid. The solid was dissolved in 40 mL of methanol plus 6 mL of water. 1 N NaOH (100 µL, 0.1 mmol) was added and the mixture stirred under nitrogen at room temperature for 18 h (overnight). The reaction was acidified by the addition of 1 N HCl and then concentrated under reduced pressure to remove the methanol. The solid present was collected by filtration and dried under reduced pressure to give the title compound (30 mg, 62%) as a white solid, mp 180–183° C.

Elemental Analysis for $C_{32}H_{29}NO_5$ Calc'd: C, 75.72; H, 5.76; N, 2.76 Found: C, 75.23; H, 5.61; N, 2.68

EXAMPLE 29

2-[6-{[(2-Butyl-benzofuran-3-carbonyl)-amino]-methyl}-1-(4-chloro-phenyl)-naphthalen-2-yloxy]-3-phenyl-propionic acid Step 1: 2-[6-{[(2-Butyl-benzofuran-3-carbonyl)-amino]-methyl}-1-(4-chloro-phenyl)-naphthalen-2-yloxy]-3-phenyl-propionic acid methyl ester. A mixture of 2-butyl-benzofuran-3-carboxylic acid [5-(4-chloro-phenyl)-6-hydroxy-naphthalen-2-ylmethyl]-amide (248 mg, (0.511 mmol), prepared in step 1 of Example 26, 3-phenyl-2-trifluoromethanesulfonyloxy-propionic acid methyl ester (299 mg, 0.96 mmol), prepared in step 2 of Example 7, and cesium carbonate (304 mg, 0.93 mmol) in 30 mL of acetone was stirred under nitrogen at room temperature for 20 h (overnight). The reaction was concentrated under reduced pressure to remove the acetone. The residue was partitioned between ethyl acetate and water. The organic layer was separated and the aqueous layer extracted multiple times with ethyl acetate. The combined organic extracts were dried (MgSO₄) and the solvent removed under reduced pressure to give 436 mg of material. Purification of the material on a 40 g KP-SIL 60 Δ Biotage column using 6:1 hexane:ethyl acetate as the eluent gave 2-[6-{[(2-butyl-benzofuran-3-carbonyl)-amino]-methyl}-1-(4-chloro-phenyl)-naphthalen-2-yloxy]-3-phenyl-propionic acid methyl ester (263 mg, 80%) as a white solid foam, mp 59–62° C.

Elemental Analysis for $C_{40}H_{36}ClNO_5$ Calc'd: C, 74.35; H, 5.62; N, 2.17 Found: C, 73.97; H, 5.62; N, 2.10

Step 2: 2-[6-{[(2-Butyl-benzofuran-3-carbonyl)-amino]-methyl}-1-(4-chloro-phenyl)-naphthalen-2-yloxy]-3-phenyl-propionic acid. 1 N NaOH (300 μL, 0.30 mmol) was added under nitrogen to a solution of 2-[6-{[(2-butyl-benzofuran-3-carbonyl)-amino]-methyl}-1-(4-chloro-phenyl)-naphthalen-2-yloxy]-3-phenyl-propionic acid methyl ester (182 mg, 0.28 mmol), prepared in the previous step, in 30 mL of methanol plus 2.5 mL of water at room temperature. After the addition the reaction was stirred at room temperature overnight. If starting material remains additional 1 N NaOH is added until the reaction is complete. A total of 900 μL of 1 N NaOH was added. The reaction was acidified by the addition of 1.6 mL of 1 N HCl and then concentrated under reduced pressure. The solid that formed was collected by filtration and dried under reduced pressure to give the title compound (166 mg, 94%) as a white solid, mp 169–172° C.

Elemental Analysis for $C_{39}H_{34}ClNO_5+0.28$ $H_2O$ Calc'd: C, 73.51; H, 5.47; N, 2.20 Found: C, 72.82; H, 5.37; N, 2.14

EXAMPLE 30

Sodium; 2-[6-{[(2-Butyl-benzofuran-3-carbonyl)-amino]-methyl}-1-(4-methoxy-phenyl)-naphthalen-2-yloxy]-3-phenyl-propionate Step 1: 2-[6-{[(2-Butyl-benzofuran-3-carbonyl)-amino]-methyl-1-(4-methoxy-phenyl)-naphthalen-2-yloxy]-3-phenyl-propionic acid methyl ester. In the same manner as described in step 1 of Example 29, 2-[6-{[(2-butyl-benzofuran-3-carbonyl)-amino]-methyl}-1-(4-methoxy-phenyl)-naphthalen-2-yloxy]-3-phenyl-propionic acid methyl ester (109 mg, 69%) was obtained as a white solid, mp 103–105° C.

Elemental Analysis for $C_{41}H_{39}NO_6$ Calc'd: C, 76.73; H, 6.13; N, 2.18 Found: C, 76.66; H, 6.24; N, 2.16

Step 2: Sodium; 2-[6-{[(2-Butyl-benzofuran-3-carbonyl)-amino]-methyl}-1-(4-methoxy-phenyl)-naphthalen-2-yloxy]-3-phenyl-propionate. 1 N NaOH (200 μL, 0.20 mmol) was added under nitrogen to 2-[6-{[(2-butyl-benzofuran-3-carbonyl)-amino]-methyl}-1-(4-methoxy-phenyl)-naphthalen-2-yloxy]-3-phenyl-propionic acid methyl ester (70.8 mg, 0.110 mmol), prepared in the previous step, in 10 mL of MeOH plus 1 mL of water at room temperature. After a few hours at room temperature a TLC showed that starting material remained. An additional 200 μL (0.20 mmol) of 1 N NaOH was added and the reaction stirred at room temperature overnight. An additional 200 μL (0.20 mmol) of 1 N NaOH was added and the reaction stirred at room temperature for 2 h. 1 N HCl (650 μL, 0.65 mmol) was added and the reaction concentrated under reduced pressure to remove the MeOH. The solid that formed was collected by filtration, rinsed with water and dried under reduced pressure to give the title compound (67 mg, 97%) was as an off-white solid, mp 138–142° C.

Elemental Analysis for $C_{40}H_{37}NO_6Na+1.05$ $H_2O$ Calc'd: C, 71.85; H, 5.74; N, 2.09 Found: C, 71.97; H, 5.64; N, 2.05

EXAMPLE 31

2-Butyl-benzofuran-3-carboxylic acid [5-bromo-6-(1H-tetrazol-5-ylmethoxy)-naphthalen-2-ylmethyl]-methyl-amide Step 1: (6-Methoxy-naphthalen-2-ylmethylene)-methyl-amine. A mixture of an 8.03M solution of methylamine in ethanol (67 mL, 537 mmol) and 50 mL of methylene chloride was added dropwise under nitrogen to a mixture of 6-methoxy-naphthalene-2-carbaldehyde (20 g, 107.4 mmol), magnesium sulfate (20 g) and 200 mL of methylene chloride. The mixture stirred at room temperature under nitrogen for 17 h. The MgSO₄ was removed by filtration and the solvent was removed under reduced pressure to give (6-methoxy-naphthalen-2-ylmethylene)-methyl-amine (20.59 g, 96%) as a yellow solid, mp 109–110° C.

Elemental Analysis for $C_{13}H_{13}NO$ Calc'd: C, 78.36; H, 6.58; N, 7.03 Found: C, 77.10; H, 6.43; N, 7.19

Step 2: (6-Methoxy-naphthalen-2-ylmethyl)-methyl-amine. (6-Methoxy-naphthalen-2-ylmethylene)-methyl-amine (20.0 g, 100 mmol), prepared in the previous step, was dissolved with heating in 300 mL of absolute ethanol. At room temperature, sodium borohydride (3.783 g, 100 mmol) was added portion wise. The reaction stirred under nitrogen for 18 h. 1N HCl was added to the reaction until pH 1 (litmus paper). The solvent was removed under reduced pressure and the resulting residue was partitioned between methylene chloride and water. The aqueous layer was made basic with 1N NaOH. The aqueous layer was separated and extracted with methylene chloride. The combined organic extracts were dried (MgSO₄) and solvent removed under reduced pressure to give (6-methoxy-naphthalen-2-ylmethyl)-methyl-amine (18.80 g, 93.5%) as an off-white solid, mp 96–104° C.

Elemental Analysis for $C_{13}H_{15}NO$ Calc'd: C, 77.58; H, 7.51; N, 6.96 Found: C, 77.21; H, 7.38; N, 6.84

Step 3: (6-Hydroxy-naphthalene-2-ylmethyl)-methyl-ammonium; bromide. (6-Methoxy-naphthalen-2-ylmethyl)- methyl-amine (18.48 g, 91.8 mmol), prepared in the previous step, was suspended in 300 mL of 48% HBr and under nitrogen the mixture was refluxed 18 h. The solvent was removed under reduced pressure to give 28.8 g of a reddish brown solid. The solid was taken up in isopropanol and stirred for 1 h. A solid was collected by filtration and dried under reduced pressure to give (6-hydroxy-naphthalene-2-ylmethyl)-methyl-ammonium; bromide (5.5 g, 22%) as a reddish brown solid, mp182–184° C.

Elemental Analysis for $C_{12}H_{14}BrNO$ Calc'd: C, 53.75; H, 5.26; N, 5.22 Found: C, 50.77; H, 5.61; N, 4.89

Step 4: 2-Butyl-benzofuran-3-carboxylic acid (6-hydroxy-naphthalen-2-ylmethyl)-methyl-amide. 2-Butyl-benzofuran-3-carbonyl chloride, prepared in step 2 of Example 3, in 40 mL of methylene chloride was added under nitrogen dropwise over 1 h to a solution of (6-hydroxy-naphthalen-2-ylmethyl)-methyl-ammonium; bromide (2.81 g, 10.5 mmol), prepared in the previous step, in 100 mL of anhydrous pyridine at ice bath temperature. After the addition the ice bath was removed and the reaction stirred at room temperature for 18 h (overnight). The reaction was acidified with 1N HCl and extracted three times with methylene chloride. The organic extracts were combined, dried ($MgSO_4$) and the solvent removed under reduced pressure to give 3.19 g of a brown oil. The oil was chromatographed on 600 g of silica gel (230–400 mesh) using 5% methanol saturated with ammonia in methylene chloride as the eluent in order to remove any acid impurities. The material isolated was chromatographed on 300 g silica gel (230–400 mesh) using 5%–15% ethyl acetate in methylene chloride as the eluent. Isolation of the desired component gave 2-butyl-benzofuran-3-carboxylic acid (6-hydroxy-naphthalen-2-ylmethyl)-methyl-amide (0.588 g, 14%) as a yellow solid, mp 110–113° C.

Elemental Analysis for $C_{25}H_{25}NO_3$ Calc'd: C, 77.49; H, 6.50; N, 3.61 Found: C, 76.58; H, 6.54; N, 3.43

Step 5: 2-Butyl-benzofuran-3-carboxylic acid (5-bromo-6-hydroxy-naphthalen-2-ylmethyl)-methyl-amide. A solution of bromine in 40 mL glacial acetic acid was added dropwise under nitrogen over 2.5 h to a solution of 2-butyl-benzofuran-3-carboxylic acid (6-hydroxy-naphthalen-2-ylmethyl)-methyl-amide (0.5364 g, 1.358 mmol), prepared in the previous step, in 60 mL of glacial acetic acid. The reaction stirred for 20 h (overnight). The solvent was removed under reduced pressure. The residue was diluted with methylene chloride, extracted with 5% $NaHCO_3$, dried ($MgSO_4$) and the solvent removed under reduced pressure to give 2-butyl-benzofuran-3-carboxylic acid (5-bromo-6-hydroxy-naphthalen-2-ylmethyl)-methyl-amide (0.6981 g, 100%.) as a light yellow foam, MS m/z: 466 [M+H]$^+$.

Elemental Analysis for $C_{25}H_{24}BrNO_3$ Calc'd: C, 64.38; H, 5.19; N, 3.00 Found: C, 63.54; H, 4.88; N, 2.93

Step 6: 2-Butyl-benzofuran-3-carboxylic acid (5-bromo-6-cyanomethoxy-naphthalen-2-ylmethyl)-methyl-amide. A mixture of 2-butyl-benzofuran-3-carboxylic acid (5-bromo-6-hydroxy-naphthalen-2-ylmethyl)-methyl-amide (0.5587 g, 1.2 mmol), prepared in the previous step, bromoacetonitrile (0.10 mL, 1.44 mmol) and potassium carbonate (0.83 g, 6 mmol) in 10 mL of DMF was stirred under nitrogen at room temperature for 18 h (overnight). The reaction was diluted with ethyl acetate and extracted multiple times with water. The organic layer was dried ($MgSO_4$) and the solvent removed under reduced pressure to give a brown oil. The oil was chromatographed on a 90 g KP-SIL 60 Å Biotage column using 5% ethyl acetate in methylene chloride as the eluent. Isolation of the desired product gave 2-butyl-benzofuran-3-carboxylic acid (5-bromo-6-cyanomethoxy-naphthalen-2-ylmethyl)-methyl-amide (0.48 g, 79%) as a clear oil, MS m/z: 505 [M+H]$^+$.

Elemental Analysis for $C_{27}H_{25}BrN_2O_3$ Calc'd: C, 64.16; H, 4.99; N, 5.54 Found: C, 64.08; H, 5.08; N, 5.34

Step 7: 2-Butyl-benzofuran-3-carboxylic acid [5-bromo-6-(1 H-tetrazol-5-ylmethoxy)-naphthalen-2-ylmethyl]-methyl-amide. A mixture of 2-butyl-benzofuran-3-carboxylic acid (5-bromo-6-cyanomethoxy-naphthalen-2-ylmethyl)-methyl-amide (0.3 g, 0.59 mmol), prepared in the previous step, sodium azide (0.116 g, 1.78 mmol) and ammonium chloride (0.095 g, 1.78 mmol) in 12 mL DMF was stirred under nitrogen at 100° C. for 6.5 h. The reaction was diluted with water, made basic with 1N NaOH, and extracted three times with ethyl acetate. The organic layers were combined, acidified with 1N HCl, dried ($MgSO_4$) and the solvent removed under reduced pressure to give an oily residue. The oil was diluted with water and the solid that formed was collected by filtration, rinsed with water and dried under reduced pressure to give the title compound (0.20 g, 63%) as an off white solid, mp 190–194° C.

Elemental Analysis for $C_{27}H_{28}BrN_5O_3+0.12 H_2O$ Calc'd: C, 58.90; H, 4.80; N, 12.72 Found: C, 57.80; H, 4.72; N, 12.34

EXAMPLE 32

2-Ethyl-benzofuran-3-carboxylic acid [5-bromo-6-(1H-tetrazol-5-ylmethoxy)-naphthalen-2-ylmethyl]-methyl-amide Step 1: 6-Methylaminomethyl-naphthalene-2-ol. (6-Hydroxy-naphthalene-2-ylmethyl)-methyl-ammonium; bromide (9 g, 33.56 mmol), prepared in step 3 of Example 31, was taken up in 300 mL of water and made basic by the addition of with 5% sodium bicarbonate. Some solid remained in the solution, which was removed by filtration. The filtrate was extracted with ethyl acetate multiple times. The organic extracts were combined, dried ($MgSO_4$) and the solvent removed under reduced pressure to give 6-methylaminomethyl-naphthalene-2-ol (5 g, 80%) as a tan solid, mp 168–169° C.

Elemental Analysis for $C_{12}H_{13}NO$ Calc'd: C, 76.98; H, 7.00; N, 7.48 Found: C, 75.70; H, 6.99; N, 7.16

Step 2: 2-Ethyl-benzofuran-3-carboxylic acid (6-hydroxy-naphthalen-2-ylmethyl)-methyl-amide. 2-Ethyl-benzofuran-3-carbonyl chloride, prepared in step 2 of Example 21, in 50 mL of anhydrous THF was added under nitrogen dropwise over 1 h to a suspension of 6-methylaminomethyl-naphthalen-2-ol (1.48 g, 7.9 mmol), prepared in the previous step, and triethylamine (1.1 mL, 7.9 mmol) in 150 mL anhydrous THF at room temperature. The reaction stirred at room temperature for 20 h (overnight). The solid present was removed by filtration and the filtrate concentrated under reduced pressure to give a brown foam. The foam was dissolved in ethyl acetate and extracted with 1N HCl. The organic layer was dried ($MgSO_4$) and the solvent removed under reduced pressure to give a brown oil which solidified when treated with hexane. The crystals were triturated with hexane and dried under reduced pressure to give 2-ethyl-benzofuran-3-carboxylic acid (6-hydroxy-naphthalen-2-ylmethyl)-methyl-amide (2.38 g, 84%) as tan solid, mp 80–90° C.

Elemental Analysis for $C_{23}H_{21}NO_3$ Calc'd: C, 76.86; H, 5.89; N, 3.90 Found: C, 74.31; H, 5.90; N, 3.48

Step 3: 2-Ethyl-benzofuran-3-carboxylic acid (5-bromo-6-hydroxy-naphthalen-2-ylmethyl)-methyl-amide. A solution of bromine in 50 mL glacial acetic acid was added dropwise under nitrogen over 3 h to a solution of 2-ethyl-benzofuran-3-carboxylic acid (6-hydroxy-naphthalen-2-ylmethyl)-methyl-amide (1.5 g, 4.17 mmol), prepared in the previous step, in 150 mL glacial acetic acid at room temperature. The reaction stirred for 17 h (overnight). The solvent was removed under reduced pressure. The residue was dissolved in methylene chloride, extracted with 5% sodium bicarbonate, dried (MgSO$_4$) and solvent removed under reduced pressure to give 2-ethyl-benzofuran-3-carboxylic acid (5-bromo-6-hydroxy-naphthalen-2-ylmethyl)-methyl-amide (1.74 g, 95%) as a brown solid, mp 176–178° C.

Elemental Analysis for $C_{23}H_{20}BrNO_3$ Calc'd: C, 63.03; H, 4.60; N, 3.20 Found: C, 62.70; H, 4.75; N, 2.87

Step 4: 2-Ethyl-benzofuran-3-carboxylic acid (5-bromo-6-cyanomethoxy-naphthalen-2-ylmethyl)-methyl-amide. A mixture of 2-ethyl-benzofuran-3-carboxylic acid (5-bromo-6-hydroxy-naphthalen-2-ylmethyl)-methyl-amide (0.5 g, 1.14 mmol), prepared in the previous step, bromoacetonitrile (95 μL, 1.36 mmol) and potassium carbonate (0.79 g, 5.7 mmol) in 20 mL of DMF was stirred under nitrogen at room temperature for 18 h (overnight). The reaction was diluted with ethyl acetate and extracted multiple times with water. The organic layer was dried (MgSO$_4$) and the solvent removed under reduced pressure to give a dark brown oil. The oil was chromatographed on 50 g of silica gel (230–400 mesh) using 5% ethyl acetate in methylene chloride as the eluent. Isolation of the desire component gave 2-ethyl-benzofuran-3-carboxylic acid (5-bromo-6-cyanomethoxy-naphthalen-2-ylmethyl)-methyl-amide (0.39 g, 72%) as a light yellow foam, MS m/z: 477 [M+H]$^+$.

Elemental Analysis for $C_{25}H_{21}BrN_2O_3$ Calc'd: C, 62.90; H, 4.43; N, 5.87 Found: C, 62.92; H, 4.44; N, 5.80

Step 5: 2-Ethyl-benzofuran-3-carboxylic acid [5-bromo-6-(1H-tetrazol-5-ylmethoxy)-naphthalen-2-ylmethyl]-methyl-amide. A mixture of 2-ethyl-benzofuran-3-carboxylic acid (5-bromo-6-cyanomethoxy-naphthalen-2-ylmethyl)-methyl-amide (0.25 g, 0.5237 mmol), prepared in the previous step, sodium azide (0.10 g, 1.57 mmol) and ammonium chloride (0.084 g, 1.57 mmol) in 12 mL DMF was stirred under nitrogen at 100° C. for 5 h. The reaction was diluted with water, made basic with 1N NaOH and extracted four times with ethyl acetate. The combined organic extracts were acidified with 1N HCl, the solvent removed under reduced pressure and the resulting residue diluted with water. The solid foam that formed was collected by filtration and dried under reduced pressure to give the title compound (0.15 g, 56%) as a tan foam, MS m/z: 520 [M+H]$^+$.

Elemental Analysis for $C_{25}H_{22}BrN_5O_3+1.5 H_2O$ Calc'd: C, 57.40; H, 4.30; N, 13.39 Found: C, 56.45; H, 4.51; N, 13.36

EXAMPLE 33

1-Phenyl-5-propyl-1H-pyrazole-4-carboxylic acid [5-bromo-6-(1H-tetrazol-5-ylmethoxy)-naphthalen-2-ylmethyl]-methyl-amide Step 1: 1-Phenyl-5-propyl-1H-pyrazole-4-carboxylic acid (6-hydroxy-naphthalen-2ylmethyl)-methyl-amide. 1-Phenyl-5-propyl-1 H-pyrazole-4-carbonyl chloride (14.82 g, 59.6 mmol) in 60 mL of methylene chloride was added under nitrogen dropwise over 10 minutes to a solution of (6-hydroxy-naphthalene-2-ylmethyl)-methyl-ammonium; bromide, prepared in step 3 of Example 31, in 150 mL of anhydrous pyridine. The reaction stirred at room temp for 17 h (overnight). The reaction was diluted with methylene chloride and extracted with 1 N HCl. The organic layer was separated and the aqueous layer extracted two times with methylene chloride. The organic extracts were combined, dried (MgSO$_4$) and solvent removed under reduced pressure to give a brown oil. This oil was dissolved in 350 mL of methanol, 100 mL water and 130 mL 1N NaOH and refluxed for 20 h (overnight). The solvent was removed under reduced pressure and the residue dissolved in methylene chloride. Ice was added to the mixture and then 130 mL of 1N HCl was added slowly. The organic layer was separated and the aqueous layer was extracted three more times with methylene chloride. The organic extracts were combined, dried (MgSO$_4$) and solvent removed under reduced pressure to give a brown oil (20.23 g). The oil was chromatographed on 1 Kg of silica gel (230–400 mesh) using methanol saturated with ammonia gas and methylene chloride as the eluent. Isolation of the desired component gave 1-Phenyl-5-propyl-1H-pyrazole-4-carboxylic acid (6-hydroxy-naphthalen-2ylmethyl)-methyl-amide (10.6 g, 89%) as a brown solid. Crystallization of the material from methanol and methylene chloride gave yellow crystals, mp 138–141° C.

Elemental Analysis for $C_{25}H_{25}N_3O_2$ Calc'd: C, 75.16; H, 6.31; N, 10.52 Found: C, 74.74; H, 6.18; N, 10.41

Step 2: 1-Phenyl-5-propyl-1H-pyrazole-4-carboxylic acid (5-bromo-6-hydroxy-naphthalen-2-ylmethyl)-methyl-amide. 1-Phenyl-5-propyl-1H-pyrazole-4-carboxylic acid (6-hydroxy-naphthalen-2ylmethyl)-methyl-amide (3.2 g, 8 mmol), prepared in the previous step, was dissolved in 300 mL glacial acetic acid (with warming). A solution of bromine (0.41 mL, 8 mmol) in 50 mL of glacial acetic acid was added under nitrogen dropwise over 2 h to the reaction at room temperature. After the addition the reaction stirred for 2 days. The solvent was removed under reduced pressure and the residue diluted with methylene chloride. The organic layer was extracted two times with 5% NaHCO$_3$, dried (MgSO$_4$) and the solvent removed under reduced pressure to give 1-phenyl-5-propyl-1H-pyrazole-4-carboxylic acid (5-bromo-6-hydroxy-naphthalen-2-ylmethyl)-methyl-amide (3.77 g, 98.5%) as a pink solid, mp 205–207° C.

Elemental Analysis for $C_{25}H_{24}BrN_3O_2$ Calc'd: C, 62.77; H, 5.06; N, 8.78 Found: C, 62.28; H, 4.88; N, 8.65

Step 3: 1-Phenyl-5-propyl-1H-pyrazole-4-carboxylic acid (5-bromo-6-cyanomethoxy-naphthalen-2-ylmethyl)-methyl-amide. A mixture of 1-phenyl-5-propyl-1H-pyrazole-4-carboxylic acid (5-bromo-6-hydroxy-naphthalen-2-ylmethyl)-methyl-amide (0.5 g, 1.045 mmol), prepared in the previous step, bromoacetonitrile (0.087 mL, 1.25 mmol) and potassium carbonate (0.72 g, 5.23 mmol) in 10 mL of DMF was stirred under nitrogen at room temperature for 2 days (over the weekend). The reaction was diluted with ethyl acetate and extracted multiple times with water. The organic layer was dried (MgSO$_4$) and the solvent removed under reduced pressure to give a brown oil (0.364 g). Purification of the oil on a 90 g KP-SIL 60 Å Biotage column using 15% ethyl acetate in methylene chloride as the eluent gave 1-phenyl-5-propyl-1H-pyrazole-4-carboxylic acid (5-bromo-6-cyanomethoxy-naphthalen-2-ylmethyl)-methyl-amide (0.32 g, 59%) as an off white solid, mp 76–80° C.

Elemental Analysis for $C_{27}H_{25}BrN_4O_2$ Calc'd: C, 62.68; H, 4.87; N, 10.83 Found: C, 62.44; H, 4.83; N, 10.69

Step 4: 1-Phenyl-5-propyl-1H-pyrazole-4-carboxylic acid [5-bromo-6-(1H-tetrazol-5-ylmethoxy)-naphthalen-2- ylmethyl]-methyl-amide. A mixture of 1-phenyl-5-propyl-1H-pyrazole-4-carboxylic acid (5-bromo-6-cyanomethoxy-naphthalen-2-ylmethyl)-methyl-amide (0.30 g, 0.58 mmol), prepared in the previous step, sodium azide (0.113 g, 1.74 mmol) and ammonium chloride (0.093 g, 1.74 mmol) in 10 mL of DMF was stirred under nitrogen at 100° C. for 6 h. By TLC the reaction was not complete. Sodium azide (0.113 g, 1.74 mmol) and ammonium chloride (0.093 g, 1.74 mmol) were added and the reaction was stirred under nitrogen at 100° C. for 6.5 h. The reaction was diluted with water, made basic by the addition of 1N NaOH and extracted five times with ethyl acetate. The combined organic extracts were acidified with 1N HCl and the solvent removed under reduced pressure. The residue was diluted with water and the solid that formed was collected by filtration and dried under reduced pressure to give the title compound (0.108 g, 33%) as a tan solid, mp 75–85° C.

Elemental Analysis for $C_{27}H_{26}BrN_7O_2+0.5$ EtOAc Calc'd: C, 57.62; H, 5.00; N, 16.22 Found: C, 57.21; H, 4.97; N, 16.22

EXAMPLE 34

1-Benzyl-1H-indole-3-carboxylic acid [5-bromo-6-(1H-tetrazol-5-ylmethoxy)-naphthalen-2-ylmethyl]-methyl-amide Step 1: 1-Benzyl-1H-indole-3-carbonyl chloride. A mixture of 1-benzyl-1H-indole-3-carboxylic acid (3.36 g, 13.37 mmol), oxalyl chloride (5.83 mL, 66.85 mmol), 100 mL methylene chloride and a catalytic amount of DMF was stirred at room temperature under nitrogen for 18 h (overnight). The solvent was removed under reduced pressure. To remove excess oxalyl chloride benzene was added and the solvent removed under reduced pressure to give 1-benzyl-1H-indole-3-carbonyl chloride as a brown oil (13.37 mmol) which was immediately used in step 2 without additional purification.

Step 2: 1-Benzyl-1H-indole-3-carboxylic acid (6-hydroxy-naphthalen-2-ylmethyl)-methyl-amide. 1-Benzyl-1H-indole-3-carbonyl chloride, prepared in the previous step, in 50 mL of anhydrous THF was added dropwise under nitrogen over 2 h to a mixture of 6-methylaminomethyl-naphthalen-2-ol (2.5 g, 13.37 mmol), prepared in step 1 of Example 32, and triethylamine (1.86 mL, 13.37 mmol) in 300 mL of anhydrous THF at room temperature. The reaction stirred for 17.5 h (overnight). A trace amount of solid was removed by filtration and the filtrate was concentrated under reduced pressure to give a brown oil. The oil was diluted with ethyl acetate, extracted two times with 1N HCl, dried (MgSO$_4$) and the solvent removed under reduced pressure to give 1-benzyl-1H-indole-3-carboxylic acid (6-hydroxy-naphthalen-2-ylmethyl)-methyl-amide (5.83 g, 100%) as a brown foam, MS m/z: 421 [M+H]$^+$.

Elemental Analysis for $C_{28}H_{24}N_2O_2$ Calc'd: C, 79.98; H, 5.75; N, 6.66 Found: C, 78.46; H, 5.95; H, 6.31

Step 3: 1-Benzyl-1H-indole-3-carboxylic acid (5-bromo-6-hydroxy-naphthalen-2-ylmethyl)-methyl-amide. A solution of bromine (0.37 mL, 0.7134 mmol) in 60 mL glacial acetic acid was added dropwise under nitrogen over 2 h to a solution of 1-benzyl-1H-indole-3-carboxylic acid (6-hydroxy-naphthalen-2-ylmethyl)-methyl-amide (3.0 g, 0.713 mmol), prepared in the previous step, in 300 mL glacial acetic acid at room temperature. The reaction stirred for 18 h (overnight). The solvent was removed under reduced pressure. The resulting residue was diluted with ethyl acetate and extracted with 5% sodium bicarbonate. A solid precipitated from the organic layer and was collected by filtration. The filtrate was dried (MgSO$_4$) and concentrated under reduced pressure to give a tan solid. The two solids were combined and taken up in a mixture of ethyl acetate and isopropanol. A certain amount of material (1.0 g) would not dissolve upon heating and was removed by filtration. The filtrate was allowed to cool and upon cooling crystals formed. The crystals were collected by filtration and dried under reduced pressure to give 1-benzyl-1H-indole-3-carboxylic acid (5-bromo-6-hydroxy-naphthalen-2-ylmethyl)-methyl-amide (0.766 g, 22%) as a tan solid, mp 181–182° C.

Elemental Analysis for $C_{28}H_{23}BrN_2O_2$ Calc'd: C, 67.34; H, 4.64; N, 5.61 Found: C, 66.59; H, 4.88; N, 5.34

Step 4: 1-Benzyl-1H-indole-3-carboxylic acid (5-bromo-6-cyanomethoxy-naphthalen-2-ylmethyl)-methyl-amide. A mixture of 1-benzyl-1H-indole-3-carboxylic acid (5-bromo-6-hydroxy-naphthalen-2-ylmethyl)-methyl-amide (1.589 g, 3.18 mmol), prepared in the previous step, bromoacetonitrile (0.265 mL, 3.8 mmol) and potassium carbonate (2.2 g, 15.9 mmol) in 15 mL DMF was stirred under nitrogen at room temperature for 20 h (overnight). The reaction was diluted with ethyl acetate and extracted five times with water. The organic layer was dried (MgSO$_4$) and the solvent removed under reduced pressure to give 1.78 g of a brown foam. The foam was chromatographed on 500 g silica gel (230–400 mesh) using ethyl acetate in methylene chloride as the eluent. Isolation of the desired product gave 1-benzyl-1H-indole-3-carboxylic acid (5-bromo-6-cyanomethoxy-naphthalen-2-ylmethyl)-methyl-amide (0.834 mg, 47%) as a white foam, MS m/z: 538 [M+H]$^+$.

Elemental Analysis for $C_{30}H_{24}BrN_3O_2$ Calc'd: C, 66.92; H, 4.49; N, 7.80 Found: C, 66.31; H, 4.27; N, 7.43

Step 5: 1-Benzyl-1H-indole-3-carboxylic acid [5-bromo-6-(1H-tetrazol-5-ylmethoxy)-naphthalen-2-ylmethyl]-methyl-amide. A mixture of 1-benzyl-1H-indole-3-carboxylic acid (5-bromo-6-cyanomethoxy-naphthalen-2-ylmethyl)-methyl-amide (0.7725 g, 1.44 mmol), prepared in the previous step, sodium azide (0.28 g, 4.3 mmol) and ammonium chloride (0.23 g, 4.3 mmol) in 15 mL DMF was stirred under nitrogen for 4 h at 100° C. The reaction was diluted with water, made basic with 1N NaOH, and extracted five times with ethyl acetate. The ethyl acetate layer was acidified with 1N HCl and the solvent was removed under reduced pressure to give 0.133 g of the desired compound as an off-white solid. The aqueous layer was acidified with 1N HCl. The solution sat at room temperature for 18 h (overnight). A solid had precipitated from solution and was collected by filtration, rinsed with water, and dried under reduced pressure to give the title compound (0.4962 g, 60%) as an off white solid, mp 197–198° C.

Elemental Analysis for $C_{30}H_{25}BrN_6O_2$ Calc'd: C, 61.97; H, 4.33; N, 14.45 Found: C, 61.26; H, 4.18; N, 13.96

EXAMPLE 35

2-Butyl-benzofuran-3-carboxylic acid methyl-[6-(1H-tetrazol-5-ylmethoxy)-naphthalen-2ylmethyl]-methyl-amide Step 1: 2-Butyl-benzofuran-3-carboxylic acid (6-cyanomethoxy-naphthalen-2ylmethyl)-methyl-amide. A mixture of 2-butyl-benzofuran-3-carboxylic acid (6-hydroxy-naphthalen-2-ylmethyl)-methyl-amide (0.90 g, 2.32 mmol), prepared in step-4 of Example 31, bromoacetonitrile (0.194 mL, 2.79 mmol) and potassium carbonate (1.6 g, 11.6 mmol) in 10 mL DMF was stirred under nitrogen at room temperature for 24 h (overnight). The reaction was diluted with ethyl acetate and extracted five times with water. The organic layer was dried ($MgSO_4$) and the solvent removed under reduced pressure to give 2-butyl-benzofuran-3-carboxylic acid (6-cyanomethoxy-naphthalen-2ylmethyl)-methyl-amide (0.94 g, 95%) as a brown oil, MS m/z: 427 [M+H]$^+$.

Elemental Analysis for $C_{27}H_{26}N_2O_3$ Calc'd: C, 76.03; H, 6.14; N, 6.57 Found: C, 75.71; H, 5.93; N, 6.50

Step 2: 2-Butyl-benzofuran-3-carboxylic acid methyl-[6-(1H-tetrazol-5-ylmethoxy)-naphthalen-2ylmethyl]-methyl-amide. A mixture of 2-butyl-benzofuran-3-carboxylic acid (6-cyanomethoxy-naphthalen-2ylmethyl)-methyl-amide (0.8 g, 1.875 mmol), prepared in the previous step, sodium azide (0.365 g, 5.6 mmol) and ammonium chloride (0.30 g, 5.6 mmol) in 15 mL of DMF was stirred under nitrogen at 100° C. for 4.5 h. The reaction was diluted with water, made basic by the addition of 1 N NaOH and extracted five times with ethyl acetate. The organic layer was acidified with 1N HCl and the solvent removed under reduced pressure to give a brown oil. The aqueous layer was acidified with 1N HCl and concentrated under reduced pressure until a brown oil precipitated. The two oils were combined to give 0.79 g of a brown oil. This oil was dissolved in 1N NaOH and acidified with 1N HCl until a solid precipitated. This solid was collected by filtration and dried under reduced pressure to give the title compound (0.7652 g, 87%) as an off white solid, mp 78–84° C., MS m/z: 470 [M+H]$^+$.

Elemental Analysis for $C_{27}H_{27}N_5O_3+0.1\ H_2O$ Calc'd: C, 68.80; H, 5.82; N, 14.86 Found: C, 67.90; H, 5.57; N, 14.50

EXAMPLE 36

2-Butyl-1-methyl-1H-indole-3-carboxylic acid [5-bromo-6-(1H-tetrazol-5-ylmethoxy)-naphthalen-2-ylmethyl]-methyl-amide Step 1: 2-Butyl-l-methyl-1H-indole. Sodium hydride (60% oil disperson; 1.52 g, 38.0 mmol) was added under nitrogen in portions over 5 minutes to a solution of 2-butyl-1H-indole (5.00 g, 28.9 mmol) in 150 mL of anhydrous DMF at room temperature. After the addition the reaction was stirred at room temperature for 1.25 h. Methyl iodide (3.60 mL, 57.8 mmol) was then added and the reaction stirred at room temperature for 3.5 h. 1 N HCl was added to the reaction until the evolution of gas ceased. The reaction was diluted with ethyl acetate, extracted multiple times with water, dried ($MgSO_4$) and the solvent removed under reduced pressure to give 2-butyl-1-methyl-1H-indole (5.70 g, 100%) as a yellow oil, MS m/z: 188 [M+H]$^+$.

Elemental Analysis for $C_{13}H_{17}N$ Cala'd: C, 83.37; H, 9.15; N, 7.48 Found: C, 83.41; H, 9.58; N, 6.82

Step 2: 1-(2-Butyl-1-methyl-1H-indol-3-yl)-2,2,2-trichloro-ethanone. Trichloroacetyl chloride (7.26 mL, 65.0 mmol) in 20 mL of methylene chloride was added under nitrogen dropwise over 30 minutes to a solution of 2-butyl-1-methyl-1 H-indole (4.87 g, 26.0 mmol), prepared in the previous step, and triethylamine (9.06 mL, 65.0 mmol) in 100 mL of methylene chloride at ice-bath temperature. After the addition the reaction was stirred at ice-bath temperature for 5 h. The ice-bath was removed and the stirring continued at room temperature for 16 h (overnight). By TLC starting material remained. Triethylamine (3.62 mL, 26.0 mmol) was added followed by the dropwise addition over 15 minutes of trichloroacetyl chloride (2.90 mL, 2.60 mmol) in 10 mL of methylene chloride. After the addition the reaction was stirred at room temperature 3 h. The reaction was extracted with 1 N HCl, 5% $NaHCO_3$, dried ($MgSO_4$) and the solvent removed under reduced pressure to give 16.46 g of a dark brown mushy solid. Purification of the solid on 1 Kg of silica gel (230–400 mesh) using 6:1 hexane: methylene chloride to 4:1 hexane:methylene chloride as the eluents gave 1-(2-butyl-1-methyl-1H-indol-3-yl)-2,2,2-trichloro-ethanone (5.54 g, 64%) as a brown solid, mp 112–115° C.

Elemental Analysis for $C_{15}H_{16}C_{13}NO$ Calc'd: C, 54.16; H, 4.85; N, 4.21 Found: C, 54.50; H, 4.88; N, 4.14

Step 3: 2-Butyl-1-methyl-1H-indole-3-carboxylic acid. A mixture of 1-(2-butyl-1-methyl-1H-indol-3-yl)-2,2,2-trichloro-ethanone (4.87 g, 14.7 mmol), prepared in the previous step, and 1 N NaOH (73.5 mL, 73.5 mmol) in 350 mL of THF was refluxed under nitrogen for 2.25 h. After cooling to room temperature 1 N HCl (80 mL, 80 mmol) was added and then the solvent was removed under reduced pressure. The residue was partitioned between 1 N HCl and methylene chloride. The organic layer was separated and the aqueous layer extracted three times with methylene chloride. The combined extracts were dried ($MgSO_4$) and the solvent removed under reduced pressure to give 2-butyl-1-methyl-1H-indole-3-carboxylic acid (3.44 g, 100%) as a brown solid, mp 163–165° C.

Elemental Analysis for $C_{14}H_{17}NO_2$ Calc'd: C, 72.70; H, 7.41; N, 6.06 Found: C, 72.20; H, 7.45; N, 5.93

Step 4: 2-Butyl-1-methyl-1H-indole-3-carbonyl chloride. Oxalyl chloride (5.89 mL, 66.1 mmol) was added under nitrogen to a solution of 2-butyl-1-methyl-1H-indole-3-carboxylic acid (3.06 g, 13.2 mmol), prepared in the previous step, in 100 mL of methylene chloride at room temperature. There was an immediate evolution of gas. After the addition the reaction was stirred at room temperature for 2 h. The solvent was removed under reduced pressure. To remove excess oxalyl chloride the residue was dissolved in benzene and the solvent removed under reduced pressure to give 2-butyl-1-methyl-1H-indole-3-carbonyl chloride as a brown oil. The material was immediately used without additional purification.

Step 5: 5-Bromo-6-methoxy-naphthalene-2-carbaldehyde. Bromine (556 µL, 10.8 mL) in 10 mL of glacial HOAc was added under nitrogen dropwise over 1 h to a solution of 6-methoxy-naphthalene-2-carbaldehyde (2.01 g, 10.8 mmol) in 25 mL of glacial HOAc at room temperature. After the addition the reaction was stirred at room temperature for 2 h. The solid was collected by filtration, rinsed with glacial HOAc and dried under reduced pressure to give 5-bromo-6-methoxy-naphthalene-2-carbaldehyde (2.27 g, 79%) as a tan solid, mp 148–150° C.

Elemental Analysis for $C_{12}H_9BrO_2$ Calc'd: C, 54.37; H, 3.42; N, 0.00 Found: C, 54.26; H, 3.28; N, 0.00

Step 6: (5-Bromo-6-methoxy-naphthalen-2-ylmethylene)-methyl-amine. Methylamine (2.35 mL of an 8.03 M solution in ethanol, 18.8 mmol) in 5 mL of methylene chloride was added under nitrogen dropwise over 5 minutes to a mixture of 5-bromo-6-methoxy-naphthalene-2-carbaldehyde (1.00 g, 3.77 mmol), prepared in the previous step, and 3 g of anhydrous $MgSO_4$ in 20 mL of methylene chloride at room temperature. After the addition the reaction was stirred at room temperature for 21 h (overnight). The reaction was filtered and the filtrate concentrated under reduced pressure to give (5-bromo-6-methoxy-naphthalen-2-ylmethylene)-methyl-amine (1.05 g, 100%) as a light tan solid, mp 105–107° C.

Elemental Analysis for $C_{13}H_{12}BrNO$ Calc'd: C, 56.14; H, 4.35; N, 5.04 Found: C, 56.12; H, 4.37; N, 4.97

Step 7: (5-Bromo-6-methoxy-naphthalen-2-ylmethyl)-methyl-amine. Sodium borohydride (131 mg, 3.47 mmol) was added under nitrogen to a warm solution of (5-bromo-6-methoxy-naphthalen-2-ylmethylene)-methyl-amine (950 mg, 4.41 mmol), prepared in the previous step, in 30 mL of absolute ethanol. After the addition the reaction was stirred at room temperature for 19 h (overnight). 1 N HCl was added dropwise until the reaction was pH~1 (litmus paper). The solvent was removed under reduced pressure and the residue partitioned between methylene chloride and water. The aqueous layer was made basic by the addition of 1 N NaOH. The organic layer was separated and the aqueous layer was extracted three times with methylene chloride. The combined extracts were dried ($MgSO_4$) and the solvent removed under reduced pressure to give (5-bromo-6-methoxy-naphthalen-2-ylmethyl)-methyl-amine (900 mg, 94%) as an off-white solid, mp 41–45° C.

Elemental Analysis for $C_{13}H_{14}BrNO$ Calc'd: C, 55.73; H, 5.04; N, 5.00 Found: C, 55.04; H, 4.80; N, 4.70

Step 8: 2-Butyl-1-methyl-1H-indole-3-carboxylic acid (5-bromo-6-methoxy-naphthalen-2-ylmethyl)-methyl-amide. A solution of 2-butyl-1-methyl-1H-indole-3-carbonyl chloride (13.2 mmol), prepared in step 4, in 50 mL of methylene chloride was added under nitrogen dropwise over 30 minutes to a solution of (5-bromo-6-methoxy-naphthalen-2-ylmethyl)-methyl-amine (3.70 g, 13.2 mmol), prepared in the previous step, and triethylamine (1.84 mL, 13.2 mmol) in 100 mL of methylene chloride at room temperature. After the addition the reaction was stirred at room temperature for 17 h (overnight). The reaction was extracted with 1 N HCl. A solid was suspended between the two layers. The solid was collected by filtration and dried under reduced pressure to give 219 mg of the HCl salt of (5-bromo-6-methoxy-naphthalen-2-ylmethyl)-methyl-amine. The organic layer of the filtrate was separated from the aqueous layer and the aqueous layer was extracted two times with methylene chloride. The combined extracts were dried ($MgSO_4$) and the solvent removed under reduced pressure to give 2-butyl-1-methyl-1H-indole-3-carboxylic acid (5-bromo-6-methoxy-naphthalen-2-ylmethyl)-methyl-amide (6.25 g, 96%) as a brown foam, MS m/z: 493 [M+H]$^+$.

Elemental Analysis for $C_{27}H_{29}BrN_2O_2$ Calc'd: C, 65.72; H, 5.92; N, 5.68 Found: C, 65.71; H, 6.13; N, 5.48

Step 9: 2-Butyl-1-methyl-1H-indole-3-carboxylic acid (5-bromo-6-hydroxy-naphthalen-2-ylmethyl)-methyl-amide. Boron tribromide (18.78 mL of a 1 M solutioin in methylene chloride; 18.78 mmol) in 20 mL of methylene chloride was added under nitrogen dropwise over fifteen minutes to a solution of 2-butyl-1-methyl-1H-indole-3-carboxylic acid (5-bromo-6-methoxy-naphthalen-2-ylmethyl)-methyl-amide (3.09 g, 6.26 mmol), prepared in the previous step, in 125 mL of methylene chloride at dry ice-acetone temperature. After the addition the dry ice-acetone bath was replaced with an ice bath and the stirring continued for 4 h. Water was added to the reaction at ice bath temperature. The organic layer was separated and the aqueous layer extracted three times with methylene chloride. The combined extracts were dried ($MgSO_4$) and the solvent removed under reduced pressure to give 2-butyl-1-methyl-1H-indole-3-carboxylic acid (5-bromo-6-hydroxy-naphthalen-2-ylmethyl)-methyl-amide (3.22 g, 100%) as a brown solid foam, MS m/z: 479 [M+H]$^+$.

Elemental Analysis for $C_{26}H_{27}BrN_2O_2$ Calc'd: C, 65.14; H, 5.68; N, 5.84 Found: C, 61.87; H, 5.47; N, 5.24

Step 10: 2-butyl-1-methyl-1H-indole-3-carboxylic acid (5-bromo-6-cyanomethoxy-naphthalen-2-ylmethyl)-methyl-amide. A mixture of 2-butyl-1-methyl-1H-indole-3-carboxylic acid (5-bromo-6-hydroxy-naphthalen-2-ylmethyl)-methyl-amide (2.09 g, 4.36 mmol), prepared in the previous step, bromoacetonitrile (364 μL, 5.23 mmol) and potassium carbonate (3.01 g, 21.8 mmol) in 50 mL of DMF was stirred under nitrogen at room temperature for 16 h (overnight). The reaction was partitioned between ethyl acetate and water. The organic layer was separated, extracted multiple times with water, dried ($MgSO_4$) and the solvent removed under reduced pressure to give 2-butyl-1-methyl-1H-indole-3-carboxylic acid (5-bromo-6-cyanomethoxy-naphthalen-2-ylmethyl)-methyl-amide (2.00 g, 88%) as a brown solid foam, MS m/z: 518 [M+H]$^+$.

Elemental Analysis for $C_{28}H_{28}BrN_3O_2$ Calc'd: C, 64.87; H, 5.44; N, 8.10 Found: C, 64.71; H, 5.54; N, 8.01

Step 11: 2-Butyl-1-methyl-1H-indole-3-carboxylic acid [5-bromo-6-(1H-tetrazol-5-ylmethoxy)-naphthalen-2-ylmethyl]-methyl-amide. A mixture of 2-butyl-1-methyl-1H-indole-3-carboxylic acid (5-bromo-6-cyanomethoxy-naphthalen-2-ylmethyl)-methyl-amide (1.79 g, 3.45 mmol), prepared in the previous step, sodium azide (673 mg, 10.35 mmol) and ammoniun chloride (554 mg, 10.36 mmol) in 100 mL of DMF was stirred under nitrogen at 100° C. for 4.25 h. The reaction was diluted with water, made basic by the addition of 20 mL of 1 N NaOH and extracted multiple times with ethyl acetate. The aqueous layer was acidified with 40 mL of 1 N HCl. A brown oil separated. The oil was partitioned between the aqueous layer and methylene chloride. The organic layer separated and the aqueous layer was extracted three times with methylene chloride. The combined extracts were dried ($MgSO_4$) and the solvent removed under reduced pressure. The residue was dissolved in 20 mL of 1 N NaOH and then acidified with 30 mL 1 N HCl. The solid that formed was collected by filtration, rinsed with water and dried under reduced pressure to give the title compound (1.75 g, 89%) as an off-white solid, mp 147–149° C.

Elemental Analysis for $C_{28}H_{29}BrN_6O_2$+0.28 $H_2O$ Calc'd: C, 59.36; H, 5.26; N, 14.83 Found: C, 55.18; H, 4.81; N, 14.19

EXAMPLE 37

1-Methyl-1H-indole-3-carboxylic acid [5-bromo-6-(1H-tetrazol-5-ylmethoxy)-naphthalen-2-ylmethyl]-methyl-amide Step 1: 1-Methyl-1H-indole-3-carbonyl chloride. Oxalyl chloride (11.86 mL, 136 mmol) was added dropwise to a solution of 1-methyl-1H-indole-3-carboxylic acid (4.76 g, 27 mmol) in 100 mL of methylene chloride. A rapid evolution of gas was observed. The reaction stirred at room temperature for 17 h (overnight). The solvent was removed under reduced pressure to give a pink solid To remove any excess oxalyl chloride the solid was dissolved in benzene and the solvent removed under reduced pressure to give 1-methyl-1H-indole-3-carbonyl chloride which was immediately used in step 2 without additional purification.

Step 2: 1-Methyl-1H-indole-3-carboxylic acid (5-bromo-6-methoxy-naphthalen-2-ylmethyl)-methyl-amide. A solution of 1-methyl-1H-indole-3-carbonyl chloride (27 mmol), prepared in the previous step, in 50 mL of methylene chloride was added dropwise under nitrogen over 1.5 h to a solution of (5-bromo-6-methoxy-naphthalen-2-ylmethyl)-methyl-amide (7.56 g, 27 mmol), prepared in step 7 of Example 36, and triethylamine (3.76 mL, 27 mmol) in 200 mL of methylene chloride at room temperature. The solution was stirred at room temperature for 22 h (overnight). The reaction was extracted with 1N HCl. The aqueous layer was separated and extracted two additional times with methylene chloride. The organic extracts were combined, dried (MgSO$_4$) and the solvent removed under reduced pressure to give 11.52 g of an off white solid. The solid was recrystallized from methylene chloride-isopropanol. Off-white crystals were collected by filtration and dried under reduced pressure to give 1-methyl-1H-indole-3-carboxylic acid (5-bromo-6-methoxy-naphthalen-2-ylmethyl)-methyl-amide (9.3389 g, 79%) as an off white solid, mp 168–169° C.

Elemental Analysis for C$_{23}$H$_{21}$BrN$_2$O$_2$ Calc'd: C, 63.17; H, 4.84; N, 6.41 Found: C, 62.81; H, 4.62; N, 6.27

Step 3: 1-Methyl-1H-indole-3-carboxylic acid (5-bromo-6-hydroxy-naphthalen-2-ylmethyl)-methyl-amide. A solution of 1.0 M boron tribromide in methylene chloride (55.0 mL, 54.9 mmol) in 50 mL of methylene chloride was added under nitrogen dropwise over 1.5 h to a solution of 1-methyl-1H-indole-3-carboxylic acid (5-bromo-6-methoxy-naphthalen-2-ylmethyl)-methyl-amide (8.0 g, 18.3 mmol), prepared in the previous step, in 300 mL of methylene chloride at dry ice-acetone temperature. The dry ice-acetone bath was replaced with an ice bath immediately after the addition. The reaction stirred at ice bath temperature for 2 h. At ice bath temperature, the reaction was quenched by the dropwise with water. The reaction was partitioned between methylene chloride and water. A solid formed in the organic layer and was collected by filtration. The solid was dried under reduced pressure to give 1-methyl-1H-indole-3-carboxylic acid (5-bromo-6-hydroxy-naphthalen-2-ylmethyl)-methyl-amide (6.5359 g, 84%) as a white solid, mp 189–190° C.

Elemental Analysis for C$_{22}$H$_{19}$BrN$_2$O$_2$ Calc'd: C, 62.42; H, 4.52; N, 6.62 Found: C, 59.60; H, 4.18; N, 6.19

Step 4: 1-Methyl-1H-indole-3-carboxylic acid (5-bromo-6-cyanomethoxy-naphthalen-2-ylmethyl)-methyl-amide. A mixture of 1-methyl-1H-indole-3-carboxylic acid (5-bromo-6-hydroxy-naphthalen-2-ylmethyl)-methyl-amide (2.0 g, 4.72 mmol), prepared in the previous step, potassium carbonate (3.26 g, 23.6 mmol) and bromoacetonitrile (0.39 mL, 5.67 mmol) in 60 mL of DMF was stirred under nitrogen at room temperature for 24 h (overnight). The reaction was partitioned between ethyl acetate and water. The organic layer was separated, extracted five times with water, dried (MgSO$_4$) and the solvent removed under reduced pressure to give 1-methyl-1H-indole-3-carboxylic acid (5-bromo-6-cyanomethoxy-naphthalen-2-ylmethyl)-methyl-amide (2.06 g, 94.5%) as a tan solid, mp 148–150° C.

Elemental Analysis for C$_{24}$H$_{20}$BrN$_3$O$_2$ Calc'd: C, 62.35; H, 4.36; N, 9.09 Found: C, 62.03; H, 4.28; N, 8.98

Step 5: 1-Methyl-1H-indole-3-carboxylic acid [5-bromo-6-(1H-tetrazol-5-ylmethoxy)-naphthalen-2-ylmethyl]-methyl-amide. A mixture of 1-methyl-1H-indole-3-carboxylic acid (5-bromo-6-cyanomethoxy-naphthalen-2-ylmethyl)-methyl-amide (1.0 g, 2.0 mmol), sodium azide (0.32 g, 6.0 mmol) and ammonium chloride (0.39 g, 6.0 mmol) in 15 mL of DMF was stirred under nitrogen at 100° C. for 6 h. The reaction was partitioned between ethyl acetate and water. The aqueous layer was made basic by the addition of 1 N NaOH. The organic layer was separated and the aqueous layer extracted five times with ethyl acetate. The aqueous layer was then acidified with 1N HCl. After 2 h a white solid had precipitated from solution. The solid was collected by filtration and dried under reduced pressure to give the title compound (0.8460 g, 84%) as an off-white solid, mp 227–228° C.

Elemental Analysis for C$_{24}$H$_{21}$BrN$_6$O$_2$+0.17 H$_2$O Calc'd: C, 56.70; H, 4.23; N, 16.53 Found: C, 56.64; H, 4.21; N, 16.47

EXAMPLE 38

5-(3,5-Dichloro-phenoxy)-furan-2-carboxylic acid [5-bromo-6-(1H-tetrazol-5-ylmethoxy)-naphthalen-2-ylmethyl]-methyl-amide Step 1: 5-(3,5-Dichloro-phenoxy)-furan-2-carboxylic acid (5-bromo-6-methoxy-naphthalen-2-ylmethyl)-methyl-amide. In the same manner as described in step 2 of Example 37, and after recrystallization of the crude product from isopropanol, 5-(3,5-dichloro-phenoxy)-furan-2-carboxylic acid (5-bromo-6-methoxy-naphthalen-2-ylmethyl)-methyl-amide (4.2757 g, 54%) was isolated as a tan solid, mp 115–117° C.

Elemental Analysis for C$_{24}$H$_{18}$BrCl$_2$NO$_4$ Calc'd: C, 53.84; H, 3.39; N, 2.62 Found: C, 53.70; H, 3.20; N, 2.50

Step 2: 5-(3,5-Dichloro-phenoxy)-furan-2-carboxylic acid (5-bromo-6-hydroxy-naphthalen-2-ylmethyl)-methyl-amide. In the same manner as described in step 3 of Example 37, with the exception that the reaction was partitioned between methylene chloride and water and no solid formed in either layer. The aqueous layer was separated and extracted two times with methylene chloride. The organic extracts were combined, dried (MgSO$_4$) and the solvent removed under reduced pressure to give 5-(3,5-dichloro-phenoxy)-furan-2-carboxylic acid (5-bromo-6-hydroxy-naphthalen-2-ylmethyl)-methyl-amide (3.45 g, 89%) as an off white foam, MS m/z: 520 [M+H]+.

Elemental Analysis for C$_{23}$H$_{16}$BrCl$_2$NO$_4$ Calc'd: C, 53.00; H, 3.09; N, 2.69 Found: C, 51.86; H, 2.77; N, 2.55

Step 3: 5-(3,5-Dichloro-phenoxy)-furan-2-carboxylic acid (5-bromo-6-cyanomethoxy-naphthalen-2-ylmethyl)-methyl-amide. Prepared in the same manner as described in step 4 of Example 37. The crude oil was chromatographed on 200 g of silica gel (230–400 mesh) using 0–5% ethyl acetate in methylene chloride as the eluent. Isolation of the desired material gave 5-(3,5-dichloro-phenoxy)-furan-2-carboxylic acid (5-bromo-6-cyanomethoxy-naphthalen-2-ylmethyl)-methyl-amide (1.2365 g, 58%) as a white foam, MS m/z: 559 [M+H]+.

Elemental Analysis for C$_{25}$H$_{17}$BrCl$_2$N$_2$O$_4$ Calc'd: C, 53.60; H, 3.06; N, 5.00 Found: C, 53.47; H, 3.07; N, 4.85

Step 4: 5-(3,5-Dichloro-phenoxy)-furan-2-carboxylic acid [5-bromo-6-(1H-tetrazol-5-ylmethoxy)-naphthalen-2-ylmethyl]-methyl-amide. In the same manner as described in step 5 of Example 37 the title compound (0.6573 g, 54%) was isolated as a tan foam, MS m/z: 602 [M+H]+.

Elemental Analysis for C$_{25}$H$_{18}$BrCl$_2$N$_5$O$_4$+0.14 H$_2$O Calc'd: C, 49.57; H, 3.04; N, 11.56 Found: C, 49.31; H, 3.18; N, 11.48

EXAMPLE 39

3-Butyl-benzofuran-2-carboxylic acid [5-bromo-6-(1H-tetrazol-5-ylmethoxy)-naphthalen-2-ylmethyl]-methyl-amide Step 1: 3-Butyl-benzofuran-2-carbonyl chloride. Oxalyl Chloride (3.86 mL, 44.2 mmol) was added under nitrogen at room temperature to a solution of 3-butyl-benzofuran-2-carboxylic acid (1.93 g, 8.84 mmol) in 60 mL of methylene chloride. After the addition a catalytic amount of DMF (10 µL) was added and the reaction was stirred at room temperature for 2 h. The solvent was removed under reduced pressure. To remove the excess oxalyl chloride the residue was dissolved in benzene and the solvent removed under reduced pressure to give 3-butyl-benzofuran-2-carbonyl chloride, which was immediately used in step 2 without additional purification.

Step 2: 3-Butyl-benzofuran-2-carboxylic acid (5-bromo-6-methoxy-naphthalen-2-ylmethyl)-methyl-amide. A solution of 3-butyl-benzofuran-2-carbonyl chloride (9.0 mmol), prepared in the previous step, in 50 mL of methylene chloride was added under nitrogen dropwise over 2 h to a solution of (5-bromo-6-methoxy-naphthalen-2-ylmethyl)-methyl-amine (2.52 g, 9.0 mmol), prepared in step 7 of Example 36, and triethylamine (1.26 mmol, 9.0 mmol) in 250 mL of methylene chloride at room temperature. After the addition the reaction was stirred at room temperature overnight. The reaction was extracted with 1 N HCl, 5% NaHCO$_3$, dried (MgSO$_4$) and the solvent removed under reduced pressure to 4.13 g of a residue. Purification of the residue on 500 g of silica gel (230–400 mesh) using 90% hexane-methylene chloride to 5% EtOAc-methylene chloride as the eluents gave 3-butyl-benzofuran-2-carboxylic acid (5-bromo-6-methoxy-naphthalen-2-ylmethyl)-methyl-amide as a clear oil, MS m/z: 480 [M+H]$^+$.

Elemental Analysis for $C_{26}H_{26}BrNO_3$ Calc'd: C, 65.01; H, 5.46; N, 2.92 Found: C, 64.23; H, 5.30; N, 2.90

Step 3: 3-Butyl-benzofuran-2-carboxylic acid (5-bromo-6-hydroxy-naphthalen-2-ylmethyl)-methyl-amide. In the same manner as described in step 9 of Example 36, 3-butyl-benzofuran-2-carboxylic acid (5-bromo-6-hydroxy-naphthalen-2-ylmethyl)-methyl-amide (1.89 g, 97%) was isolated as a brown solid, mp 53–56° C.

Elemental Analysis for $C_{25}H_{24}BrNO_3$ Calc'd: C, 64.38; H, 5.19; N, 3.00 Found: C, 63.69; H, 5.08; N, 2.87

Step 4: 3-Butyl-benzofuran-2-carboxylic acid (5-bromo-6-cyanomethoxy-naphthalen-2-ylmethyl)-methyl-amide. In the same manner as described in step 10 of Example 36, 3-butyl-benzofuran-2-carboxylic acid (5-bromo-6-cyanomethoxy-naphthalen-2-ylmethyl)-methyl-amide was isolated as a brown oil, MS m/z: 505 [M+H]$^+$.

Elemental Analysis for $C_{27}H_{25}BrN_2O_3$ Calc'd: C, 64.16; H, 4.99; N, 5.54 Found: C, 63.19; H, 5.02; N, 5.73

Step 5: 3-Butyl-benzofuran-2-carboxylic acid [5-bromo-6-(1H-tetrazol-5-ylmethoxy)-naphthalen-2-ylmethyl]-methyl-amide. A mixture of 3-butyl-benzofuran-2-carboxylic acid (5-bromo-6-cyanomethoxy-naphthalen-2-ylmethyl)-methyl-amide (1.90 g, 3.77 mmol), prepared in the previous step, sodium azide (735 mg, 11.3 mmol) and ammonium chloride (607 mg, 11.3 mmol) in 50 mL of DMF was stirred under nitrogen at 100° C. for 5 h. By TLC starting material remained. An additional 732 mg (11.3 mmol) of sodium azide was added and the stirring continued at 100° C. for 2 h. The reaction was diluted with 50 mL of water, made basic by the addition of 1 N NaOH and then extracted three times with ethyl acetate. The aqueous layer was acidified with 1 N HCl and the solid that formed was collected by filtration and dried under reduced pressure to give the title compound (1.17 g, 57%) as a light brown solid, mp 180–183° C.

Elemental Analysis for $C_{27}H_{26}BrN_5O_3$+0.01 H$_2$O Calc'd: C, 59.11; H, 4.78; N, 12.77 Found: C, 58.93; H, 4.73; N, 12.94

EXAMPLE 40

2-Benzyl-3-(1-bromo-6-{[(3-butyl-benzofuran-2-carbonyl)-methyl-amino]-methyl}-naphthalen-2-yloxy)-propionic acid Step 1: 2-Benzyl-3-(1-bromo-6-{[(3-butyl-benzofuran-2-carbonyl)-methyl-amino]-methyl}-naphthalen-2-yloxy)-propionic acid methyl ester. A mixture of 3-butyl-benzofuran-2-carboxylic acid (5-bromo-6-hydroxy-naphthalen-2-ylmethyl)-methyl-amide (1.03 g, 2.20 mmol), prepared in step 3 of Example 39, 3-phenyl-2-trifluoromethanesulfonyloxy-propionic acid methyl ester (1.04 g, 3.32 mmol), prepared in step 2 of Example 7, and cesium carbonate (1.44 g, 4.41 mmol) in 60 mL of acetone was stirred under nitrogen at room temperature for 8 h. The acetone was removed under reduced pressure and the residue partitioned between ethyl acetate and water. The aqueous layer was separated and extracted three times with ethyl acetate. The combined organic extracts were dried (MgSO$_4$) and the solvent removed under reduced pressure to give 1.63 g of an oil. Purification of the oil on a 90 g KP-SIL 60 Å Biotage column using 1:1 hexane-methylene chloride as the eluent gave 2-benzyl-3-(1-bromo-6-{[(3-butyl-benzofuran-2-carbonyl)-methyl-amino]-methyl}-naphthalen-2-yloxy)-propionic acid methyl ester (869 mg, 63%) as a clear oil, MS m/z: 628 [M+H]$^+$.

Elemental Analysis for $C_{35}H_{34}BrNO_5$ Calc'd: C, 66.88; H, 5.45; N, 2.23 Found: C, 66.95; H, 5.51; N, 2.22

Step 2: 2-Benzyl-3-(1-bromo-6-{[(3-butyl-benzofuran-2-carbonyl)-methyl-amino]-methyl}-naphthalen-2-yloxy)-propionic acid. A mixture of 1 N NaOH (2.5 mL, 2.5 mmol) and 2-benzyl-3-(1-bromo-6-{[(3-butyl-benzofuran-2-carbonyl)-methyl-amino]-methyl}-naphthalen-2-yloxy)-propionic acid methyl ester (769 mg, 1.22 mmol), prepared in the previous step, in 30 mL of methanol plus 2 mL of water was stirred under nitrogen at room temperature for 6 h. By TLC starting material remained. An additional 2.5 mL (2.5 mmol) of 1 N NaOH was added and the stirring continued at room temperature overnight. 1 N HCl (5.1 mL, 5.1 mmol) was added and the reaction concentrated under reduced pressure to remove the methanol. The solid that formed was collected by filtration and dried under reduced pressure to give the title compound (318 mg, 42%) as a white solid, mp 64–68° C.

Elemental Analysis for $C_{34}H_{32}BrNO_5$+0.45 H$_2$O Calc'd: C, 65.59; H, 5.53; N, 2.25 Found: C, 64.75; H, 5.21; N, 2.15

EXAMPLE 41

3-Methyl-benzofuran-2-carboxylic acid [5-bromo-6-(1H-tetrazol-5-ylmethoxy)-naphthalen-2-ylmethyl]-methyl-amide Step 1: 3-Methyl-benzofuran-2-carbonyl chloride. In the same manner as described in step 1 of Example 39, 3-methyl-benzofuran-2-carbonyl chloride was isolated and immediately used in step 2 without additional purification.

Step 2: 3-Methyl-benzofuran-2-carboxylic acid (5-bromo-6-methoxy-naphthalen-2-ylmethyl)-methyl-amide. In the same manner as described in step 2 of Example 39, 3-methyl-benzofuran-2-carboxylic acid (5-bromo-6-methoxy-naphthalen-2-ylmethyl)-methyl-amide (8.17 g, 92%) was isolated as a white solid, mp138–140° C.

Elemental Analysis for $C_{23}H_{20}BrNO_3$ Calc'd: C, 63.03; H, 4.60; N, 3.20 Found: C, 62.68; H, 4.21; N, 3.13

Step 3: 3-Methyl-benzofuran-2-carboxylic acid (5-bromo-6-hydroxy-naphthalen-2-ylmethyl)-methyl-amide. In the same manner as described in step 9 of Example 36, 3-methyl-benzofuran-2-carboxylic acid (5-bromo-6-hydroxy-naphthalen-2-ylmethyl)-methyl-amide (5.81 g, 100%) was isolated as a brown foam, MS m/z: 424 [M+H]$^+$.

Elemental Analysis for $C_{22}H_{18}BrNO_3$ Calc'd: C, 62.28; H, 4.28; N, 3.30 Found: C, 60.03; H, 4.26; N, 3.04

Step 4: 3-Methyl-benzofuran-2-carboxylic acid (5-bromo-6-cyanomethoxy-naphthalen-2-ylmethyl)- methyl-amide. In the same manner as described in step 10 of Example 36, 3-methyl-benzofuran-2-carboxylic acid (5-bromo-6-cyanomethoxy-naphthalen-2-ylmethyl)-methyl-amide (2.67 g, 98%) was isolated as a brown solid, mp 35–38° C.

Elemental Analysis for $C_{24}H_{19}BrN_2O_3$ Calc'd: C, 62.22; H, 4.13; N, 6.05 Found: C, 61.78; H, 4.02; N, 5.85

Step 5: 3-Methyl-benzofuran-2-carboxylic acid [5-bromo-6-(1H-tetrazol-5-ylmethoxy)-naphthalen-2-ylmethyl]-methyl-amide. A mixture of 3-methyl-benzofuran-2-carboxylic acid (5-bromo-6-cyanomethoxy-naphthalen-2-ylmethyl)-methyl-amide (2.039 g, 4.40 mmol), sodium azide (846 mg, 13.0 mmol) and ammonium chloride (695 mg, 13.0 mmol) in 60 mL of DMF was stirred under nitrogen at 100° C. for 6 h. The reaction was diluted with water, made basic by the addition of 1 N NaOH and extracted three times with ethyl acetate. The aqueous layer was acidified with 1 N HCl, which caused an oil to precipitate. The aqueous layer was decanted from the oil. Water was added to the oil, which caused it to solidify. The solid was collected by filtration, rinsed with water and dried under reduced pressure to give the title compound as a white solid, mp 164–166° C.

Elemental Analysis for $C_{24}H_{20}BrN_5O_3$ Calc'd: C, 56.93; H, 3.98; N, 13.83 Found: C, 56.43; H, 3.86; N, 13.75

EXAMPLE 42

Sodium; 2-benzyl-3-(1-bromo-6-{[methyl-(3-methyl-benzofuran-2-carbonyl)-amino]-methyl}-naphthalen-2-yloxy)-propionate Step 1: 2-Benzyl-3-(1-bromo-6-{[methyl-(3-methyl-benzofuran-2-carbonyl)-amino]-methyl}-naphthalen-2-yloxy)-propionic acid methyl ester. In the same manner as described in step 1 of Example 40, and replacing 3-butyl-benzofuran-2-carboxylic acid (5-bromo-6-hydroxy-naphthalen-2-ylmethyl)-methyl-amide with 3-methyl-benzofuran-2-carboxylic acid (5-bromo-6-hydroxy-naphthalen-2-ylmethyl)-methyl-amide, prepared in step 3 of Example 41, 2-benzyl-3-(1-bromo-6-{[methyl-(3-methyl-benzofuran-2-carbonyl)-amino]-methyl}-naphthalen-2-yloxy)-propionic acid methyl ester (3.31 g, 97%) was isolated as a clear oil, MS m/z: 586 [M+H]$^+$.

Elemental Analysis for $C_{32}H_{28}BrNO_5$ Calc'd: C, 65.54; H, 4.81; N, 2.39 Found: C, 66.25; H, 4.65; N, 1.67

Step 2: Sodium; 2-benzyl-3-(1-bromo-6-{[methyl-(3-methyl-benzofuran-2-carbonyl)-amino]-methyl}-naphthalen-2-yloxy)-propionate. A mixture of 1 N NaOH (12 mL, 12 mmol) and 2-benzyl-3-(1-bromo-6-{[methyl-(3-methyl-benzofuran-2-carbonyl)-amino]-methyl}-naphthalen-2-yloxy)-propionic acid methyl ester (3.31 g, 5.80 mmol), prepared in the previous step, in 120 mL of methanol plus 15 mL of water was stirred under nitrogen at room temperature overnight. 1 N HCl (13 mL, 13 mmol) was added and the reaction concentrated under reduced pressure to remove the methanol. The solid that formed was collected by filtration and dried under reduced pressure to give the title compound (2.16 g, 67%) as a white solid, mp 112–114° C.

Elemental Analysis for $C_{31}H_{26}BrNO_5Na+0.15\ H_2O$ Calc'd: C, 62.35; H, 4.27; N, 2.35 Found: C, 63.31; H, 4.47; N, 2.30

EXAMPLE 43

3-Methyl-benzofuran-2-carboxylic acid [5-bromo-6-(1H-tetrazol-5-ylmethoxy)-naphthalen-2-ylmethyl]-amide Step 1: 5-Bromo-6-methoxy-naphthalene-2-carbonitrile. Bromine (7.0 mL, 0.137 mol) in 100 mL of glacial HOAc was added under nitrogen dropwise over 4 h to a solution of 6-methoxy-naphthalene-2-carbonitrile (25.02 g, 0.137 mol) in 700 mL of glacial HOAc at room temperature. After the addition the reaction was stirred at room temperature overnight. The solid that formed was collected by filtration, rinsed with glacial HOAc and dried under reduced pressure to give 5-bromo-6-methoxy-naphthalene-2-carbonitrile (31.35 g, 88%) as a white solid, mp 177–178° C.

Elemental Analysis for $C_{12}H_8BrNO$ Calc'd: C, 54.99; H, 3.08; N, 5.34 Found: C, 55.16; H, 2.92; N, 5.43

Step 2: 5-Bromo-6-methoxy-naphthalen-2-ylmethyl-ammonium; chloride. $BH_3$-THF (286 mL of a 1.0 molar solution in THF; 286 mmol) was added under nitrogen dropwise over 45 minutes to a solution of 5-bromo-6-methoxy-naphthalene-2-carbonitrile (25.02 g, 95.4 mmol), prepared in the previous step, in 650 mL of anhydrous THF at room temperature. After the addition the reaction was refluxed overnight. The reaction was quenched by the dropwise addition of 60 mL of 1 N HCl. The solid that precipitated was collected by filtration and dried under reduced pressure to give 5-bromo-6-methoxy-naphthalen-2-ylmethyl-ammonium; chloride (5.34 g, 21%) as a white solid, mp 274–276° C.

Elemental Analysis for $C_{12}H_{12}BrNO+HCl+0.71H_2O$ Calc'd: C, 45.70; H, 4.61; N, 4.44 Found: C, 45.65; H, 4.60; N, 4.31

Step 3: 3-Methyl-benzofuran-2-carboxylic acid (5-bromo-6-methoxy-naphthalen-2-ylmethyl)-amide. 3-Methyl-benzofuran-2-carbonyl chloride (1.23 g, 6.34 mmol), prepared in step 1 of Example 41, in 30 mL of methylene chloride was added under nitrogen dropwise to a suspension of 5-bromo-6-methoxy-naphthalen-2-ylmethyl-ammonium; chloride (2.00 g, 6.34 mmol), prepared in the previous step, in 700 mL of anhydrous pyridine at room temperature. After the addition the reaction was stirred at room temperature overnight. The reaction was concentrated under reduced pressure to remove most of the solvent. The residue was partitioned between 1 N HCl and methylene chloride. The aqueous layer was separated and extracted two times with methylene chloride. The combined extracts were dried ($MgSO_4$) and the solvent removed under reduced pressure to give 2.37 g of a residue. Purification of the residue by chromatography on silica gel gave 3-methyl-benzofuran-2-carboxylic acid (5-bromo-6-methoxy-naphthalen-2-ylmethyl)-amide (1.60 g, 60%) as a white solid, mp 154–156° C.

Elemental Analysis for $C_{22}H_{18}BrNO_3$ Calc'd: C, 62.28; H, 4.28; N, 3.30 Found: C, 62.14; H, 4.13; N, 3.22

Step 4: 3-Methyl-benzofuran-2-carboxylic acid (5-bromo-6-hydroxy-naphthalen-2-ylmethyl)-amide. In the same manner as described in step 3 of Example 37, 3-methyl-benzofuran-2-carboxylic acid (5-bromo-6-hydroxy-naphthalen-2-ylmethyl)-amide (1.34 g, 91%) was isolated as a white solid, mp 194–197° C.

Elemental Analysis for $C_{21}H_{16}BrNO_3$ Calc'd: C, 61.48; H, 3.93; N, 3.41 Found: C, 61.48; H, 3.90; N, 3.14

Step 5: 3-Methyl-benzofuran-2-carboxylic acid (5-bromo-6-cyanomethoxy-naphthalen-2-ylmethyl)-amide. In the same manner as described in step 10 of Example 36, 3-methyl-benzofuran-2-carboxylic acid (5-bromo-6-cyanomethoxy-naphthalen-2-ylmethyl)-amide (1.25 g, 96%) was isolated as a yellow solid, mp 194–197° C.

Elemental Analysis for $C_{23}H_{17}BrN_2O_3$ Calc'd: C, 61.48; H, 3.81; N, 6.23 Found: C, 61.69; H, 3.89; N, 6.01

Step 6: 3-Methyl-benzofuran-2-carboxylic acid [5-bromo-6-(1H-tetrazol-5-ylmethoxy)-naphthalen-2- ylmethyl]-amide. A mixture of 3-methyl-benzofuran-2-carboxylic acid (5-bromo-6-cyanomethoxy-naphthalen-2-ylmethyl)-amide (1.14 g, 2.54 mmol), prepared in the previous step, sodium azide (492 mg, 7.57 mmol) and ammonium chloride (406 mg, 7.59 mmol) in 50 mL of DMF was stirred under nitrogen at 100° C. for 5 h. By TLC starting material remained. An additional 494 mg (7.60 mmol) of sodium azide was added and the stirring continued at 100° C. for 2 h. The reaction was diluted with water, made basic by the addition of 1 N NaOH and extracted three times with ethyl acetate. The aqueous layer was acidified with 1 N HCl and the solid that precipitated was collected by filtration and dried under reduced pressure to give the title compound (987 mg, 79%) as a light brown solid, mp 212–215° C.

Elemental Analysis for $C_{23}H_{18}BrN_5O_3+0.18$ $H_2O$ Calc'd: C, 55.74; H, 3.73; N, 14.13 Found: C, 55.86; H, 3.72; N, 14.13

EXAMPLE 44

2-(1-Bromo-6-{[(3-methyl-benzofuran-2-carbonyl)-amino]-methyl}-naphthalen-2-yloxy)-3-phenyl-propionic acid Step 1: 2-(1-Bromo-6-{[(3-methyl-benzofuran-2-carbonyl)-amino]-methyl}-naphthalen-2-yloxy)-3-phenyl-propionic acid methyl ester. In the same manner as described in step 1 of Example 40, and replacing 3-butyl-benzofuran-2-carboxylic acid (5-bromo-6-hydroxy-naphthalen-2-ylmethyl)-methyl-amide with 3-methyl-benzofuran-2-carboxylic acid (5-bromo-6-hydroxy-naphthalen-2-ylmethyl)-amide, prepared in step 4 of Example 43, 2-(1-bromo-6-{[(3-methyl-benzofuran-2-carbonyl)-amino]-methyl}-naphthalen-2-yloxy)-3-phenyl-propionic acid methyl ester (1.76 g, 100%) was isolated as an off-white solid, mp 129–133° C.

Elemental Analysis for $C_{31}H_{26}BrNO_5$ Calc'd: C, 65.04; H, 4.58; N, 2.45 Found: C, 64.28: H, 4.70; N, 2.25

Step 2: 2-(1-Bromo-6-{[(3-methyl-benzofuran-2-carbonyl)-amino]-methyl}-naphthalen-2-yloxy)-3-phenyl-propionic acid. A mixture of 1 N NaOH (5 mL, 5 mmol) and 2-(1-bromo-6-{[(3-methyl-benzofuran-2-carbonyl)-amino]-methyl}-naphthalen-2-yloxy)-3-phenyl-propionic acid methyl ester (1.58 g, 2.76 mmol), prepared in the previous step, in 200 mL of methanol plus 5 mL of water was stirred under nitrogen at room temperature overnight and then at 60° C. for 6 h. 1 N HCl (6.2 mL, 6.2 mmol) was added and the reaction concentrated under reduced pressure to remove the methanol. The solid that precipitated was collected by filtration and dried under reduced pressure to give the title compound as an off-white solid, mp 110–113° C.

Elemental Analysis for $C_{30}H_{24}BrNO_5+0.42$ $H_2O$ Calc'd: C, 63.66; H, 4.42; N, 2.47 Found: C, 63.47; H, 4.30; N, 2.40

EXAMPLE 45

3-Phenethyl-benzofuran-2-carboxylic acid [5-bromo-6-(1H-tetrazol-5-ylmethoxy)-naphthalen-2-ylmethyl]-methyl-amide Step 1: 3-Phenethyl-benzofuran-2-carboxylic acid. 3-Methyl-benzofuran-2-carboxylic acid (9.99 g, 56.7 mmol) in 150 mL of anhydrous THF was added under nitrogen dropwise to a solution of lithium diisopropylamide (60 mL of a 2.0 M solution in heptane/THF/ethylbenzene; 120 mmol) in 350 mL of anhydrous THF at –10° C. After the addition was complete the reaction was stirred at –10° C. for approximately 10 minutes. Benzyl bromide (13.5 mL, 113 mmol) was then added dropwise to the reaction. After the addition the reaction was allowed to warm to room temperature and then stirred at room temperature for 2 h. The reaction was acidified by the addition of 1 N HCl and then concentrated under reduced pressure to remove the THF. The residue was partitioned between 1 N HCl and methylene chloride. The aqueous layer was separated and extracted two times with methylene chloride. The combined extracts were dried ($MgSO_4$) and the solvent removed under reduced pressure. The residue was recrystallized from ethyl acetate to give 3-phenethyl-benzofuran-2-carboxylic acid (1.62 g, 11%) as a white solid, mp 169–172° C.

Elemental Analysis for $C_{17}H_{14}O_3$ Calc'd: C, 76.68; H, 5.30; N, 0.00 Found: C, 76.18; H, 5.27; N, 0.02

Step 2: 3-Phenethyl-benzofuran-2-carboxyl chloride. In the same manner as described in step 1 of Example 39, 3-Phenethyl-benzofuran-2-carboxyl chloride (1.65 g, 100%) was isolated and immediately used in step 3 without additional purification.

Step 3: 3-Phenylethyl-benzofuran-2-carboxylic acid (5-bromo-6-methoxy-naphthalen-2-ylmethyl)-methyl-amide. 3-Phenethyl-benzofuran-2-carboxyl chloride (1.65 g, 5.80 mmol), prepared in the previous step, in 60 mL of methylene chloride was added under nitrogen to a mixture of (5-bromo-6-methoxy-naphthalen-2-ylmethyl)-methyl-amine (1.62 g, 5.80 mmol), prepared in step 7 of Example 36, and triethylamine (815 μL, 5.80 mmol) in 80 mL of methylene chloride at room temperature. After the addition the reaction was stirred at room temperature overnight. The reaction was extracted with 1 N HCl, 5% $NaHCO_3$, dried ($MgSO_4$) and the solvent removed under reduced pressure to give 2.89 g of a light brown foam. Purification of the foam on a 120 g KP-SIL 60 Å Bioitage column using 4:1 hexane:ethyl acetate as the eluent gave 3-phenylethyl-benzofuran-2-carboxylic acid (5-bromo-6-methoxy-naphthalen-2-ylmethyl)-methyl-amide (2.72 g, 89%) as a white solid, mp 54–57° C.

Elemental Analysis for $C_{30}H_{26}BrNO_3$ Calc'd: C, 68.19; H, 4.96; N, 2.65 Found: C, 67.96; H, 4.85; N, 2.51

Step 4: 3-Phenylethyl-benzofuran-2-carboxylic acid (5-bromo-6-hydroxy-naphthalen-2-ylmethyl)-methyl-amide. In the same manner as described in step 3 of Example 37, 3-phenylethyl-benzofuran-2-carboxylic acid (5-bromo-6-hydroxy-naphthalen-2-ylmethyl)-methyl-amide (2.48 g, 97%) was isolated as a brown solid, mp 108–110° C.

Elemental Analysis for $C_{29}H_{24}BrNO_3$ Calc'd: C, 67.71; H, 4.70; N, 2.72 Found: C, 65.97; H, 4.36; N, 2.55

Step 5: 3-Phenylethyl-benzofuran-2-carboxylic acid (5-bromo-6-cyanomethoxy-naphthalen-2-ylmethyl)-methyl-amide. In the same manner as described in step 10 of Example 36, 3-phenylethyl-benzofuran-2-carboxylic acid (5-bromo-6-cyanomethoxy-naphthalen-2-ylmethyl)-methyl-amide (2.54 g, 99%) was isolated as a dark green solid, mp 51–55° C.

Elemental Analysis for $C_{31}H_{25}BrN_2O_3$ Calc'd: C, 67.28; H, 4.55; N, 5.06 Found: C, 66.46; H, 4.48; N, 5.52

Step 6: 3-Phenethyl-benzofuran-2-carboxylic acid [5-bromo-6-(1H-tetrazol-5-ylmethoxy)-naphthalen-2-ylmethyl]-methyl-amide. A mixture of 3-phenylethyl-benzofuran-2-carboxylic acid (5-bromo-6-cyanomethoxy-naphthalen-2-ylmethyl)-methyl-amide (2.29 g, 4.15 mmol), prepared in the previous step, sodium azide (808 mg, 12.4 mmol) and ammonium chloride (668 mg, 12.5 mmol) in 50 mL of DMF was stirred under nitrogen at 100° C. for 5 h. By TLC starting material remained. An additional 801 mg (12.3 mmol) of sodium azide was added and the reaction stirred at 100° C. overnight. The reaction was diluted with 50 mL of water, made basic by the addition of 1 N NaOH and extracted three times with ethyl acetate. The aqueous layer was acidified with 1 N HCl. An oil precipitated. The aqueous layer was decanted and the oil partitioned between methylene chloride and water. The organic layer was separated, dried (MgSO$_4$) and the solvent removed under reduced pressure to give the title compound as a light brown solid, mp 56–59° C.

Elemental Analysis for $C_{31}H_{26}BrN_5O_3$+0.07 H$_2$O Calc'd: C, 62.29; H, 4.41; N, 11.72 Found: C, 61.47; H, 4.19; N, 11.75

EXAMPLE 46

2-(1-Bromo-6-{[methyl-(3-phenethyl-benzofuran-2-carbonyl)-amino]-methyl}-naphthalen-2-yloxy)-3-phenyl-propionic acid Step 1: 2-(1-Bromo-6-{[methyl-(3-phenethyl-benzofuran-2-carbonyl)-amino]-methyl}-naphthalen-2-yloxy)-3-phenyl-propionic acid methyl ester. In the same manner as described in step 1 of Example 40, and replacing 3-butyl-benzofuran-2-carboxylic acid (5-bromo-6-hydroxy-naphthalen-2-ylmethyl)-methyl-amide with 3-phenylethyl-benzofuran-2-carboxylic acid (5-bromo-6-hydroxy-naphthalen-2-ylmethyl)-methyl-amide, prepared in step 4 of Example 45, 2-(1-bromo-6-{[methyl-(3-phenethyl-benzofuran-2-carbonyl)-amino]-methyl}-naphthalen-2-yloxy)-3-phenyl-propionic acid methyl ester (1.84 g, 93%) was isolated as a white solid, mp 29–32° C.

Elemental Analysis for $C_{39}H_{34}BrNO_5$ Calc'd: C, 69.23; H, 5.06; N, 2.07 Found: C, 69.10; H, 5.06; N, 1.85

Step 2: 2-(1-Bromo-6-{[methyl-(3-phenethyl-benzofuran-2-carbonyl)-amino]-methyl}-naphthalen-2-yloxy)-3-phenyl-propionic acid. A mixture of 1 N NaOH (5 mL, 5 mmol) and 2-(1-bromo-6-{[methyl-(3-phenethyl-benzofuran-2-carbonyl)-amino]-methyl}-naphthalen-2-yloxy)-3-phenyl-propionic acid methyl ester (1.68 g, 2.49 mmol), prepared in the previous step, in 110 mL of methanol plus 5 mL of water was stirred under nitrogen at room temperature overnight. 1 N HCl (50 mL, 50 mmol) was added and the reaction was concentrated under reduced pressure to remove the methanol. The solid that formed was collected by filtration and dried under reduced pressure to give the title compound (1.20 g, 73%) as a white solid, mp 87–90° C.

Elemental Analysis for $C_{38}H_{32}BrNO_5$+0.48 H$_2$O Calc'd: C, 68.00; H, 4.95; N, 2.09 Found: C, 68.39; H, 4.67; N, 2.03

EXAMPLE 47

(1-Bromo-6-{[methyl-(3-phenethyl-benzofuran-2-carbonyl)-amino]-methyl}-naphthalen-2-yloxy)-acetic acid Step 1: (1-Bromo-6-{[methyl-(3-phenethyl-benzofuran-2-carbonyl)-amino]-methyl}-naphthalen-2-yloxy)-acetic acid methyl ester. A mixture of 3-phenylethyl-benzofuran-2-carboxylic acid (5-bromo-6-hydroxy-naphthalen-2-ylmethyl)-methyl-amide, prepared in step 4 of Example 45, methyl bromoacetate (260 μL, 2.75 mmol) and potassium carbonate (1.58 g, 11.96 mmol) in 25 mL of DMF was stirred under nitrogen at room temperature 16 h (overnight). The reaction was partitioned between ethyl acetate and water. The organic layer was separated, extracted multiple times with water, dried (MgSO$_4$) and the solvent removed under reduced pressure to give (1-bromo-6-{[methyl-(3-phenethyl-benzofuran-2-carbonyl)-amino]-methyl}-naphthalen-2-yloxy)-acetic acid methyl ester (1.29 g, 96%) as a light brown foam, MS m/z: 586 [M+H]$^+$.

Elemental Analysis for $C_{32}H_{28}BrNO_5$ Calc'd: C, 65.54; H, 4.81; N, 2.39 Found: C, 64.38; H, 4.68; N, 2.27

Step 2: (1-Bromo-6-{[methyl-(3-phenethyl-benzofuran-2-carbonyl)-amino]-methyl}-naphthalen-2-yloxy)-acetic acid. A mixture of 1 N NaOH (4 mL, 4 mmol) and (1-bromo-6-{[methyl-(3-phenethyl-benzofuran-2-carbonyl)-amino]-methyl}-naphthalen-2-yloxy)-acetic acid methyl ester (1.19 g, 2.02 mmol), prepared in the previous step, in 100 mL of methanol plus 4 mL of water was stirred under nitrogen at room temperature overnight. 1 N HCl (4 mL, 4 mmol) was added and the reaction concentrated under reduced pressure to remove the methanol. The solid that formed was collected by filtration and dried under reduced pressure to give the title compound (1.11 g, 96%) as an off-white solid, mp 119–122° C.

Elemental Analysis for $C_{31}H_{26}BrNO_5Na$+0.51 H$_2$O Calc'd: C, 61.68; H, 4.34; N, 2.32 Found: C, 61.85; H, 4.21; N, 2.33

EXAMPLE 48

2-Butyl-benzofuran-3-carboxylic acid benzyl-[5-bromo-6-(1H-tetrazol-5-ylmethoxy)-naphthalen-2-yl methyl]-amide Step 1: Benzyl-(6-methoxy-naphthalen-2-ylmethylene)-amine. A solution of benzylamine (0.57 mL, 5.37 mmol) in 5 mL of methylene chloride was added dropwise under nitrogen over 5 minutes to a mixture of 6-methoxy-naphthalene-2-carbaldehyde (1.0 g, 5.37 mmol) and anhydrous MgSO$_4$ (3 g) in 20 mL of methylene chloride. The reaction stirred under nitrogen for 24 h (overnight). The MgSO$_4$ was removed by filtration and the solvent removed under reduced pressure to give benzyl-(6-methoxy-naphthalen-2-ylmethylene)-amine (1.455 g, 98%) as an off-white solid, mp 115–117° C.

Elemental Analysis for $C_{19}H_{17}NO$ Calc'd: C, 82.88; H, 6.22; N, 5.09 Found: C, 83.26; H, 6.22; N, 5.04

Step 2: Benzyl-(6-methoxy-naphthalen-2-ylmethyl)-amine. Sodium borohydride (0.19 g, 5 mmol) was added in portions under nitrogen to a solution of benzyl-(6-methoxy-naphthalen-2-ylmethylene)-amine (1.38 g, 5 mmol), prepared in the previous step, in 150 mL of absolute ethanol at room temperature. After the addition the reaction was stirred at room temperature for 20 h (overnight). The reaction was quenched with 30 mL of 1N HCl (pH 2 by litmus paper). The solvent was removed under reduced pressure to give a solid. The solid was partitioned between methylene chloride and water. The aqueous layer was made basic with 1N NaOH. The aqueous layer was separated and extracted two times with methylene chloride. The organic extracts were combined, dried (MgSO$_4$) and the solvent removed under reduced pressure to give benzyl-(6-methoxy-naphthalen-2-ylmethyl)-amine (1.38 g, 100%) as an off-white solid, mp 45–53° C.

Elemental Analysis for $C_{19}H_{19}NO$ Calc'd: C, 82.28; H, 6.90; N, 5.05 Found: C, 82.64; H, 6.91; N, 4.97

Step 3: 6-(Benzylamino-methyl)-naphthalen-2-ol. A mixture of benzyl-(6-methoxy-naphthalen-2-ylmethyl)-amine (1.3 g, 4.7 mmol), prepared in the previous step, 65 mL of 48% HBr and 50 mL of glacial acetic acid was refluxed under nitrogen for 19 h (overnight). The solvent was removed under reduced pressure to give a red solid. The solid was suspended in 250 mL of water and heated until most of the solid dissolved. The mixture was filtered, the filtrate made basic with sodium bicarbonate and extracted three times with ethyl acetate. The organic extracts were combined, dried (MgSO$_4$) and the solvent removed under reduced pressure to give 6-(benzylamino-methyl)-naphthalen-2-ol (0.76 g, 62%) as a green solid, mp 120–122° C.

Elemental Analysis for C$_{18}$H$_{17}$NO Calc'd: C, 82.10; H, 6.51; N, 5.32 Found: C, 80.58; H, 6.21; N, 5.22

Step 4: 2-Butyl-benzofuran-3-carboxylic acid benzyl-(6-hydroxy-naphthalen-2-ylmethyl)-amide. 2-Butyl-benzofuran-3-carbonyl-chloride (3 mmol), prepared in step 2 of Example 3, in 25 mL of anhydrous THF was added under nitrogen dropwise over 1 h to a solution of 6-(benzylamino-methyl)-naphthalen-2-ol (0.71 g, 2.7 mmol), prepared in the previous step, and triethylamine (0.376 mL, 2.7 mmol) in 75 mL of anhydrous THF at room temperature. After the addition the reaction was stirred at room temperature for 20 h (overnight). The solid present was removed by filtration and the filtrate concentrated under reduced pressure to give a brown oil. The oil was dissolved in ethyl acetate and extracted with 1N HCl. The organic layer was dried (MgSO$_4$) and the solvent removed under reduced pressure. Chromatography of the crude oil on 200 g of silica gel (230–400 mesh) using 0%–5% ethyl acetate in methylene chloride as the eluent gave 2-butyl-benzofuran-3-carboxylic acid benzyl-(6-hydroxy-naphthalen-2-ylmethyl)-amide (0.8164 g, 65%) as a light yellow solid, mp 160–164° C.

Elemental Analysis for C$_{31}$H$_{29}$NO$_3$ Calc'd: C, 80.32; H, 6.31; N, 3.02 Found: C, 80.07; H, 6.34; N, 2.82

Step 5: 2-Butyl-benzofuran-3-carboxylic acid benzyl-(5-bromo-6-hydroxy-naphthalen-2-ylmethyl)-amide. Prepared in the same manner as described in step 3 of Example 32, 2-butyl-benzofuran-3-carboxylic acid benzyl-(5-bromo-6-hydroxy-naphthalen-2-ylmethyl)-amide (0.60 g, 100%) was isolated as a light yellow foam, MS m/z: 542 [M+H]$^+$.

Elemental Analysis for C$_{31}$H$_{28}$BrNO$_3$ Calc'd: C, 68.64; H, 5.20; N, 2.58 Found: C, 67.92; H, 5.25; N, 2.39

Step 6: 2-Butyl-benzofuran-3-carboxylic acid benzyl-(5-bromo-6-cyanomethoxy-naphthalen-2-ylmethyl)-amide. Prepared in the same manner as described in step 4 of Example 32. The crude material was chromatographed on 50 g silica gel (230–400 mesh) using 0–5% ethyl acetate in methylene chloride as the eluent. Isolation of the desired component gave 2-butyl-benzofuran-3-carboxylic acid benzyl-(5-bromo-6-cyanomethoxy-naphthalen-2-ylmethyl)-amide (0.33 g, 81%) as a tan solid, mp 105–110° C.

Elemental Analysis for C$_{33}$H$_{29}$BrN$_2$O$_3$ Calc'd: C, 68.15; H, 5.03; N, 4.82 Found: C, 67.95; H, 4.82; N, 4.79

Step 7: 2-Butyl-benzofuran-3-carboxylic acid benzyl-[5-bromo-6-(1H-tetrazol-5-ylmethoxy)-naphthalen-2-ylmethyl]-amide. Prepared in the same manner as described in step 5 of Example 32, the title compound was isolated as a tan foam (0.18 g, 65%), MS m/z: 624 [M+H]$^+$.

Elemental Analysis for C$_{33}$H$_{30}$BrN$_5$O$_3$+0.17 H$_2$O Calc'd: C, 63.16; H, 4.87; N, 11.16 Found: C, 61.88; H, 5.26; N, 11.10

EXAMPLE 49

2-Methyl-benzofuran-3-carboxylic acid benzyl-[5-bromo-6-(1H-tetrazol-5-ylmethoxy)-naphthalen-2-ylmethyl]-amide Step 1: 2-Methyl-benzofuran-3-carboxylic acid benzyl-(6-hydroxy-naphthalen-2ylmethyl)-amide. Prepared in the same manner as described in step 2 of Example 32, and replacing 2-ethyl-benzofuran-3-carbonyl chloride with 2-methyl-benzofuran-3-carbonyl chloride, prepared in step 2 of Example 20 and 6-methylaminomethyl-naphthalen-2-ol with 6-(benzylamino-methyl)-naphthalen-2-ol, prepared in step 3 of Example 48. Chromatography of the crude oil on 400 g silica gel (230–400 mesh) using 2–3% ethyl acetate in methylene chloride as the eluent gave 2-methyl-benzofuran-3-carboxylic acid benzyl-(6-hydroxy-naphthalen-2ylmethyl)-amide (0.71 g, 30%) as a yellow solid, mp 190–193° C.

Elemental Analysis for C$_{28}$H$_{23}$NO$_3$ Calc'd: C, 79.79; H, 5.50; N, 3.32 Found: C, 79.14; H, 5.65; N, 2.89

Step 2: 2-Methyl-benzofuran-3-carboxylic acid benzyl-(5-bromo-6-hydroxy-naphthalen-2ylmethyl)-amide. Prepared in the same manner as described in step 3 of Example 32. The crude oil was crystallized with hexane and then recrystallized from isopropanol. Light yellow crystals were collected by filtration and dried under reduced pressure to give 1.0 g (69%) of 2-methyl-benzofuran-3-carboxylic acid benzyl-(5-bromo-6-hydroxy-naphthalen-2ylmethyl)-amide, mp 184–185° C.

Elemental Analysis for C$_{28}$H$_{22}$BrNO$_3$ Calc'd: C, 67.21; H, 4.43; N, 2.80 Found: C, 67.08; H, 4.39; N, 2.71

Step 3: 2-Methyl-benzofuran-3-carboxylic acid benzyl-(5-bromo-6-cyanomethoxy-naphthalen-2ylmethyl)-amide. Prepared in the same manner as described in step 4 of Example 32. The crude oil was crystallized with hexane and ethyl acetate and dried under reduced pressure to give 2-methyl-benzofuran-3-carboxylic acid benzyl-(5-bromo-6-cyanomethoxy-naphthalen-2ylmethyl)-amide (0.423 g, 98%) as a tan solid, mp 145–146° C.

Elemental Analysis for C$_{30}$H$_{23}$BrN$_2$O$_3$ Calc'd: C, 66.80; H, 4.30; N, 5.19 Found: C, 66.57; H, 4.48; N, 5.23

Step 4: 2-Methyl-benzofuran-3-carboxylic acid benzyl-[5-bromo-6-(1H-tetrazol-5-ylmethoxy)-naphthalen-2-ylmethyl]-amide. In the same manner as described in step 7 of Example 31, the title compound (0.13 g, 48%) was isolated as a tan foam, MS m/z: 582 [M+H]$^+$.

Elemental Analysis for C$_{30}$H$_{24}$BrN$_5$O$_3$ Calc'd: C, 61.65; H, 4.18; N, 11.98 Found: C, 60.52; H, 4.58; N, 11.38

EXAMPLE 50

2-Ethyl-benzofuran-3-carboxylic acid benzyl-[5-bromo-6-(1H-tetrazol-5ylmethoxy)-naphthalen-2-ylmethyl]-amide Step 1: 2-Ethyl-benzofuran-3-carboxylic acid benzyl-(6-hydroxy-naphthalen-2ylmethyl)-amide. Prepared in the same manner as described in step 2 of Example 32, and replacing 6-methylaminomethyl-naphthalen-2-ol with 6-(benzylamino-methyl)-naphthalen-2-ol, prepared in step 3 of Example 48. The crude oil was purified by chromatography on 500 g of silica gel (230–400 mesh) using 5% ethyl acetate in methylene chloride as the eluent. Isolation of the desired product gave 2-ethyl-benzofuran-3-carboxylic acid benzyl-(6-hydroxy-naphthalen-2-ylmethyl)-amide (1.9 g, 83%) as a yellow oil, MS m/z: 436 [M+H]$^+$.

Elemental Analysis for C$_{29}$H$_{25}$NO$_3$+0.65 C$_4$H$_8$O$_2$ Calc'd: C, 77.02; H, 6.18; N, 2.84 Found: C, 76.88; H, 5.99; N, 2.82

Step 2: 2-Ethyl-benzofuran-3-carboxylic acid benzyl-(5-bromo-6-hydroxy-naphthalen-2-ylmethyl)-amide. Prepared in the same manner as described in step 3 of Example 32. The crude yellow solid was purified by recrystallization from a minimum amount of ethyl acetate. The crystals were collected by filtration and dried under reduced pressure to give 2-ethyl-benzofuran-3-carboxylic acid benzyl-(5-bromo-6-hydroxy-naphthalen-2-ylmethyl)-amide (1.1 g, 60%) as light yellow crystals, mp 125–130° C.

Elemental Analysis for $C_{29}H_{24}BrNO_3$ Calc'd: C, 67.71; H, 4.70; N, 2.72 Found: C, 67.56; H, 4.77; N, 2.61

Step 3: 2-Ethyl-benzofuran-3-carboxylic acid benzyl-(5-bromo-6-cyanomethoxy-naphthalen-2-ylmethyl)-amide. Prepared in the same manner as described in step 4 of Example 32. The crude product was dried under reduced pressure to give 2-ethyl-benzofuran-3-carboxylic acid benzyl-(5-bromo-6-cyanomethoxy-naphthalen-2-ylmethyl)-amide (0.394 g, 92%) as a tan solid, mp 92–100° C.

Elemental Analysis for $C_{31}H_{25}BrN_2O_3$ Calc'd: C, 67.28; H, 4.55; N, 5.06 Found: C, 67.22; H, 4.75; N, 5.07

Step 4: 2-Ethyl-benzofuran-3-carboxylic acid benzyl-[5-bromo-6-(1H-tetrazol-5ylmethoxy)-naphthalen-2-ylmethyl)-amide. Prepared in the same manner as described in step 7 of Example 31. The title compound was isolated as a tan foam (0.21 g, 78%), MS m/z: 596 [M+H]$^+$.

Elemental Analysis for $C_{31}H_{26}BrN_5O_3$+0.08 $H_2O$ Calc'd: C, 62.27; H, 4.41; N, 11.71 Found: C, 61.32; H, 4.71; N, 11.05

EXAMPLE 51

2-Butyl-benzofuran-3-carboxylic acid [5-bromo-6-(1H-tetrazol-5-ylmethoxy)-naphthalen-2-ylmethyl]-butyl-amide Step 1: Butyl-(6-methoxy-naphthalen-2-ylmethylene)-amine. Prepared in the same manner as described in step 1 of Example 48 and replacing benzylamine with butylamine gave butyl-(6-methoxy-naphthalen-2-ylmethylene)-amine (12.1 g, 93%) as a yellow solid, MS m/z: 242 [M+H]$^+$.

Elemental Analysis for $C_{16}H_{19}NO$ Calc'd: C, 79.60; H, 7.94; N, 5.80 Found: C, 78.97; H, 7.88; N, 5.66

Step 2: Butyl-(6-methoxy-naphthalen-2-ylmethyl)-amine. Prepared in the same manner as described in step 2 of Example 48, butyl-(6-methoxy-naphthalen-2-ylmethyl)-amine (10.65 g, 87.6%) was isolated as an off white solid, mp 55–80° C.

Elemental Analysis for $C_{16}H_{21}NO$ Calc'd: C, 78.97; H, 8.70; N, 5.76 Found: C, 78.53; H, 8.73; N, 5.53

Step 3: 6-Butylaminomethyl-naphthalen-2-ol. A mixture of butyl-(6-methoxy-naphthalen-2-ylmethyl)-amine (10.0 g, 41.09 mmol), prepared in the previous step, 300 mL of 48% HBr and 200 mL of glacial acetic acid was refluxed under nitrogen for 19 h (overnight). The solvent was removed under reduced pressure. The resulting residue was partitioned between ethyl acetate and 5% sodium bicarbonate. The organic layer was separated, dried (MgSO$_4$) and the solvent removed under reduced pressure to give 6-butylaminomethyl-naphthalen-2-ol (7.54 g, 80%) as a brown solid, mp 108–112° C.

Elemental Analysis for $C_{15}H_{19}NO$ Calc'd: C, 78.56; H, 8.35; N, 6.11 Found: C, 73.43; H, 7.76; N, 5.56

Step 4: 2-Butyl-benzofuran-3-carboxylic acid butyl-(6-hydroxy-naphthalen-2-ylmethyl)-amide. Prepared in the same manner as described in step 4 of Example 48, and replacing 6-(benzylamino-methyl)-naphthalen-2-ol with 6-butylaminomethyl-naphthalen-2-ol, prepared in the previous step, gave 2-butyl-benzofuran-3-carboxylic acid butyl-(6-hydroxy-naphthalen-2-ylmethyl)-amide as a brown oil, MS m/z: 430 [M+H]$^+$.

Elemental Analysis for $C_{28}H_{31}NO_3$ Calc'd: C, 78.29; H, 7.27; N, 3.26 Found: C, 77.45; H, 7.15; N, 2.63

Step 5: 2-Butyl-benzofuran-3-carboxylic acid (5-bromo-6-hydroxy-naphthalen-2-ylmethyl)-butyl-amide. A solution of bromine (0.193 mL, 3.748 mmol) in 50 mL of glacial acetic acid was added dropwise under nitrogen to a solution of 2-butyl-benzofuran-3-carboxylic acid butyl-(6-hydroxy-naphthalen-2-ylmethyl)-amide (1.61 g, 3.748 mmol), prepared in the previous step, in 150 mL of glacial acetic acid at room temperature. The reaction was stirred at room temperature for 18 h. The solvent was removed under reduced pressure. The resulting residue was made basic with 5% NaHCO$_3$ and extracted five times with ethyl acetate. The organic layer was dried (MgSO$_4$) and the solvent removed under reduced pressure to give 1.83 g of a brown foam. The foam was chromatographed on 400 g of silica gel (230–400 mesh) using 0–2% ethyl acetate in methylene chloride as the eluent. Isolation of the desired material gave 2-butyl-benzofuran-3-carboxylic acid (5-bromo-6-hydroxy-naphthalen-2-ylmethyl)-butyl-amide (0.9549 g, 50%) as a tan foam, MS m/z: 508 [M+H]$^+$.

Elemental Analysis for $C_{28}H_{30}BrNO_3$ Calc'd: C, 66.14; H, 5.95; N, 2.75 Found: C, 66.44; H, 5.98; N, 2.65

Step 6: 2-Butyl-benzofuran-3-carboxylic acid (5-bromo-6-cyanomethoxy-naphthalen-2-ylmethyl)-butyl-amide. In the same manner as described in step 4 of Example 32, 2-butyl-benzofuran-3-carboxylic acid (5-bromo-6-cyanomethoxy-naphthalen-2-ylmethyl)-butyl-amide (0.530 g, 99%) was isolated as a brown foam, MS m/z: 547 [M+H]$^+$.

Elemental Analysis for $C_{30}H_{31}BrN_2O_3$ Calc'd: C, 65.01; H, 5.71; N, 5.12 Found: C, 65.55; H, 5.80; N, 5.22

Step 7: 2-Butyl-benzofuran-3-carboxylic acid [5-bromo-6-(1H-tetrazol-5-ylmethoxy)-naphthalen-2-ylmethyl]-butyl-amide. A mixture of 2-butyl-benzofuran-3-carboxylic acid (5-bromo-6-cyanomethoxy-naphthalen-2-ylmethyl)-butyl-amide (0.285 g, 0.52 mmol), prepared in the previous step, sodium azide (0.101 g, 1.56 mmol) and ammonium chloride (0.083 g, 1.56 mmol) in 10 mL of anhydrous DMF was stirred at 100° C. under nitrogen for 5 h. By TLC starting material remained. Additional amounts of sodium azide (0.101 g, 1.56 mmol) and ammonium chloride (0.083 g, 1.56 mmol) were added and the reaction stirred at 100° C. under nitrogen for 3 h. The reaction was diluted with water, made basic with 1N NaOH and extracted five times with ethyl acetate. The organic layer was separated and acidified with 1N HCl. The solvent was removed under reduced pressure and the residue diluted with 10 mL of water. A solid foam formed, which was collected by filtration and dried under reduced pressure to give the title compound (0.2765 g, 90%) as a tan foam, MS m/z: 588 [M–H]$^-$.

Elemental Analysis for $C_{30}H_{32}BrN_5O_3$+0.32 $H_2O$ Calc'd: C, 60.43; H, 5.52; N, 11.75 Found: C, 60.44; H, 5.46; N, 11.41

EXAMPLE 52

2-Methyl-benzofuran-3-carboxylic acid [5-bromo-6-(1H-tetrazol-5-ylmethoxy)-naphthalen-2-ylmethyl]-butyl-amide Step 1: 2-Methyl-benzofuran-3-carboxylic acid butyl-(6-hydroxy-naphthalen-2-ylmethyl)-amide. Prepared in the same manner as described in step 4 of Example 48 and replacing 6-(benzylamino-methyl)-naphthalen-2-ol with 6-butylaminomethyl-naphthalen-2-ol, prepared in step 3 of Example 51, and replacing 2-butyl-benzofuran-3-carbonyl chloride with 2-methy-benzofuran-3-carbonyl chloride, prepared in step 2 of Example 20. Purification of the crude product on 300 g silica gel (230–400 mesh) using 25%–33% ethyl acetate in hexane as the eluent gave 2-methyl-benzofuran-3-carboxylic acid butyl-(6-hydroxy-naphthalen-2-ylmethyl)-amide (1.03 g, 47%) as a tan solid, mp 126–128° C.

Elemental Analysis for $C_{25}H_{25}NO_3$ Calc'd: C, 77.49; H, 6.50; N, 3.61 Found: C, 77.69; H, 6.43; N, 3.57

Step 2: 2-Methyl-benzofuran-3-carboxylic acid (5-bromo-6-hydroxy-naphthalen-2-ylmethyl)-butyl-amide. In the same manner as described in step 5 of Example 51, 2-methyl-benzofuran-3-carboxylic acid (5-bromo-6-hydroxy-naphthalen-2-ylmethyl)-butyl-amide (1.1176 g, 99%) was isolated as an off-white foam, MS m/z: 464 [M−H]⁻.

Elemental Analysis for $C_{25}H_{24}BrNO_3$ Calc'd: C, 64.38; H, 5.19; N, 3.00 Found: C, 63.99; H, 5.19; N, 2.86

Step 3: 2-Methyl-benzofuran-3-carboxylic acid (5-bromo-6-cyanomethoxy-naphthalen-2-ylmethyl)-butyl-amide. Prepared in the same manner as described in step 4 of Example 32. The crude material was chromatographed on 200 g of silica gel (230–400 mesh) using 0%–2% ethyl acetate in methylene chloride as the eluent. Isolation of the desired material gave 2-methyl-benzofuran-3-carboxylic acid (5-bromo-6-cyanomethoxy-naphthalen-2-ylmethyl)-butyl-amide (0.41 g, 76%) as a white foam, MS m/z: 505 [M+H]⁺.

Elemental Analysis for $C_{27}H_{25}BrN_2O_3$ Calc'd: C, 64.16; H, 4.99; N, 5.54 Found: C, 63.86; H, 4.86; N, 5.35

Step 4: 2-Methyl-benzofuran-3-carboxylic acid [5-bromo-6-(1H-tetrazol-5-ylmethoxy)-naphthalen-2-ylmethyl]-butyl-amide. In the same manner as described in step 7 of Example 51, the title compound (0.22 g, 67%) was isolated as an off-white solid, mp 204–206° C.

Elemental Analysis for $C_{27}H_{26}BrN_5O_3 + 0.04 H_2O$ Calc'd: C, 59.05; H, 4.79; N, 12.75 Found: C, 58.73; H, 4.86; N, 12.47

EXAMPLE 53

2-[1-Bromo-6-({[5-(3,5-dichloro-phenoxy)-furan-2-carbonyl]-amino}-methyl)-naphthalen-2-yloxy]-3-phenyl-propionic acid Step 1: (5-Bromo-6-hydroxy-naphthalen-2-ylmethyl)-carbamic acid tert-butyl ester. A solution of benzyltrimethylammoniumbromide (1.755 g, 4.5 mmol) in 50 mL of methylene chloride was added dropwise under nitrogen over 2 h to a mixture of (6-hydroxy-naphthalen-2-ylmethyl)-carbamic acid tert-butyl ester (1.24 g, 4.5 mmol), prepared in step 1 of Example 13, and calcium carbonate (1.35 g, 13.5 mmol) in 150 mL of methylene chloride plus 60 mL of methanol. The reaction was stirred for 20 h (overnight). The reaction was diluted with water and extracted three times with methylene chloride. The organic extracts were combined, dried (MgSO₄) and the solvent removed under reduced pressure to give 1.4 g of a yellow solid. The solid was recrystallized from 15 mL of isopropanol. The crystals were collected by filtration and dried under reduced pressure to give (5-bromo-6-hydroxy-naphthalen-2-ylmethyl)-carbamic acid tert-butyl ester (0.95 g, 60%) as an off white solid, mp 150–152° C.

Elemental Analysis for $C_{16}H_{18}BrNO_3$ Calc'd: C, 54,56; H, 5.15; N, 3.98 Found: C, 54.22; H, 4.84; N, 3.82

Step 2: 2-[1-Bromo-6-(tert-butoxycarbonylamino-methyl)-naphthalen-yloxy]-3-phenyl-propionic acid methyl ester. A solution of 3-phenyl-2-trifluoromethane-sulfonyloxy-propionic acid methyl ester (5.0 g, 16 mmol), prepared in step 2 of Example 7, in 25 mL of acetone was added under nitrogen to a mixture of (5-bromo-6-hydroxy-naphthalen-2-ylmethyl)-carbamic acid tert-butyl ester (3.7 g, 10.5 mmol), prepared in the previous step, and cesium carbonate (6.84 g, 21 mmol) in 100 mL of acetone at room temperature. The reaction was stirred for 17 h (overnight). The solvent was removed under reduced pressure and the residue was diluted with water and extracted three times with ethyl acetate. The organic extracts were combined, dried (MgSO₄) and the solvent removed under reduced pressure to give 6 g of a yellow solid. The solid was chromatographed on 600 g of silica gel (230–400 mesh) using 5% ethyl acetate in methylene chloride as the eluent. Isolation of the desired material gave 2-[1-bromo-6-(tert-butoxycarbonylamino-methyl)-naphthalen-yloxy]-3-phenyl-propionic acid methyl ester (4.02 g, 74%) as a white solid.

Elemental Analysis for $C_{26}H_{28}BrNO_5$ Calc'd: C, 60.71; H, 5.49; N, 2.72 Found: C, 61.10; H, 5.55; N, 2.50

Step 3: 5-Bromo-6-(1-methoxycarbonyl-2-phenyl-ethoxy)-naphthalen-2-ylmethyl-ammonium; chloride. A solution of 50 mL of ethyl acetate saturated with HCl gas was added under nitrogen to 2-[1-bromo-6-(tert-butoxycarbonylamino-methyl)-naphthalen-yloxy]-3-phenyl-propionic acid methyl ester (2.0 g, 3.888 mmol), prepared in the previous step. A precipitate formed within 0.5 h. The reaction stirred for 19 h (overnight). The solid was collected by filtration, rinsed two times with ethyl acetate and dried under reduced pressure to give 5-bromo-6-(1-methoxycarbonyl-2-phenyl-ethoxy)-naphthalen-2-ylmethyl-ammonium; chloride (1.3, 72%) as an off-white solid, MS m/z: 414 [M+H]+.

Elemental Analysis for $C_{21}H_{20}BrNO_3$+HCl Calc'd: C, 55.96; H, 4.70; N, 3.11 Found: C, 56.18; H, 4.66; N, 3.08

Step 4: 2-[1-Bromo-6-({[5-(3,5-dichloro-phenoxy)-furan-2-carbonyl]-amino}-methyl)-naphthalen-2-yloxy]-3-phenyl-propionic acid methyl ester. 5-(3,5-Dichloro-phenoxy)-furan-2-carbonyl chloride (0.194 g, 0.6655 mmol) was added under nitrogen to a suspension of 5-bromo-6-(1-methoxycarbonyl-2phenyl-ethoxy)-naphthalen-2-ylmethyl-ammonium; chloride (0.30 g, 0.6655 mmol), prepared in the previous step, in 20 mL of methylene chloride at room temperature. Triethylamine (0.186 mL, 1.33 mmol) was then added to the mixture. The reaction was stirred at room temperature for 18 h (overnight). The reaction was diluted with methylene chloride, extracted one time with 1N HCl and two times with 5% NaHCO₃. The organic layer was separated, dried (MgSO₄) and the solvent removed under reduced pressure to give 2-[1-bromo-6-({[5-(3,5-dichloro-phenoxy)-furan-2-carbonyl]-amino}-methyl)-naphthalen-2-yloxy]-3-phenyl-propionic acid methyl ester (0.4079 g, 92%) as a tan oil, MS m/z: 668 [M+H]+.

Elemental Analysis for $C_{32}H_{24}BrCl_2NO_6$ Calc'd: C, 57.42; H, 3.61; N, 2.09 Found: C, 57.26; H, 3.45; N, 2.07

Step 5: 2-[1-Bromo-6-({[5-(3,5-dichloro-phenoxy)-furan-2-carbonyl]-amino}-methyl)-naphthalen-2-yloxy]-3-phenyl-propionic acid. A mixture of 2-[1-bromo-6-({[5-(3, 5-dichloro-phenoxy)-furan-2-carbonyl]-amino}-methyl)-naphthalen-2-yloxy]-3-phenyl-propionic acid methyl ester (0.34 g, 0.508 mmol), prepared in the previous step, 1N NaOH (1.50 mL, 1.5 mmol), 5 mL of water and 50 mL of methanol was stirred under nitrogen at room temperature for 18 h (overnight). The methanol was removed under reduced pressure. The solid that formed was collected by filtration and identified as the sodium salt salt of 2-[1-bromo-6-({[5-

(3,5-dichloro-phenoxy)-furan-2-carbonyl]-amino}-methyl)-naphthalen-2-yloxy]-3-phenyl-propionic acid (0.1537 g, 46%). The clear filtrate was acidified with 1N HCl. The solid that precipitated was collected by filtration and dried under reduced pressure to give the title compound (0.0905 g, 27%) as a white solid, mp 86–100° C.

Elemental Analysis for $C_{31}H_{22}NO_6Cl_2Br+0.32\ H_2O$ Calc'd: C, 56.32; H, 3.45; N, 2.12 Found: C, 56.09; H, 3.35; N, 2.09

EXAMPLE 54

2-(1-Bromo-6-{[(1-phenyl-5-propyl-1H-pyrazole-4-carbonyl)-amino]-methyl}-naphthalen-2-yloxy)-3-phenyl-propionic acid. In the same manner as described in Example 53, the title compound was isolated as a white solid, MS m/z: 612 [M+H]+.

Elemental Analysis for $C_{33}H_{30}BrN_3O_4+0.49\ H_2O$ Calc'd: C, 63.79; H, 5.03; N, 6.76 Found: C, 63.82; H, 4.93; N, 6.84

EXAMPLE 55

2-{1-Bromo-6-[4-cyclohexyl-benzoylamino)-methyl]-naphthalen-2-yloxy}-3-phenyl-propionic acid Step 1: 2-{1-Bromo-6-[(4-cyclohexyl-benzoylamino)-methyl]-naphthalen-2-yloxy}-3-phenyl-propionic acid methyl ester. 4-Cyclohexyl-benzoyl chloride (0.67 mmol) was added under nitrogen to a suspension of 5-bromo-6-(1-methoxycarbonyl-2-phenyl-ethoxy)-naphthalen-2-ylmethyl-ammonium; chloride (0.30 g, 0.67 mmol), prepared in step 3 of Example 53, in 20 mL of methylene chloride at room temperature. Triethylamine (0.186 mL, 1.33 mmol) was then added to the mixture. After the addition the reaction was stirred at room temperature for 18 h (overnight). The reaction was diluted with methylene chloride, extracted one time with 1N HCl and two times with 5% NaHCO₃. The organic layer was separated, dried (MgSO₄) and the solvent removed under reduced pressure to give 2-{1-bromo-6-[(4-cyclohexyl-benzoylamino)-methyl]-naphthalen-2-yloxyl}-3-phenyl-propionic acid methyl ester (0.3362 g, 84%) as an off-white solid, mp 160–161° C.

Elemental Analysis for $C_{34}H_{34}BrNO_4$ Calc'd: C, 68.00; H, 5.71; N, 2.33 Found: C, 67.67; H, 5.55; N, 2.29

Step 2: 2-{1-Bromo-6-[4-cyclohexyl-benzoylamino)-methyl]-naphthalen-2-yloxy}-3-phenyl-propionic acid. A mixture of 2-{1-bromo-6-[(4-cyclohexyl-benzoylamino)-methyl]-naphthalen-2-yloxy}-3-phenyl-propionic acid methyl ester (0.2174 g, 0.362 mmol), prepared in the previous step, 1N NaOH (1.0 mL, 1.0 mmol), 5 mL of H₂O and 100 mL of methanol was refluxed under nitrogen for 5 h. The reaction was cooled to room temperature and acidified with 1N HCl. The methanol was removed under reduced pressure. The solid that precipitated was collected by filtration, washed two times with water and dried under reduced pressure to give the title compound (0.1506 g, 71%) as a white solid, mp 179–182° C.

Elemental Analysis for $C_{31}H_{22}NO_6Cl_2Br+0.32\ H_2O$ Calc'd: C, 56.32; H, 3.45; N, 2.12 Found: C, 56.09; H, 3.35; N, 2.09

EXAMPLE 56

2-{1-Bromo-6-[(3,5-di-tert-butyl-benzoylamino)-methyl]-naphthalen-2-yloxy}-3-phenyl-propionic acid. In the same manner as described in Example 55, the title compound was isolated as a white solid, mp 160–163° C.

Elemental Analysis for $C_{35}H_{38}BrNO_4+0.3\ H_2O$ Calc'd: C, 67.59; H, 6.26; N, 2.25 Found: C, 67.57; H, 6.18; N, 2.32

EXAMPLE 57

2-{1-Bromo-6-[(3-phenoxy-benzoylamino)-methyl]-naphthalen-2-yloxy}-3-phenyl-propionic acid. In the same manner as described in Example 55, the title compound was isolated as a white solid, MS m/z: 596 [M+H]+.

Elemental Analysis for $C_{33}H_{26}BrNO_5+0.33\ H_2O$. Calc'd: C, 65.79; H, 4.46; N, 2.33 Found: C, 63.84; H, 4.36; N, 2.22

EXAMPLE 58

2-(1-Bromo-6-{[(2-ethyl-benzofuran-3-carbonyl)-amino]-methyl}-naphthalen-2-yloxy)-3-phenyl-propionic acid Step 1: 2-(1-Bromo-6-{[(2-ethyl-benzofuran-3-carbonyl)-amino]-methyl}-naphthalen-2-yloxy)-3-phenyl-propionic acid methyl ester. 2-Ethyl-benzofuran-3-carbonyl chloride (0.444 mmol), prepared in step 2 of Example 21, was added under nitrogen to a suspension of 5-bromo-6-(1-methoxycarbonyl-2-phenyl-ethoxy)-naphthalen-2-ylmethyl-ammonium; chloride (0.200 g, 0.444 mmol), prepared in step 3 of Example 53, in 20 mL of methylene chloride. Triethylamine (0.124 mL, 0.888 mmol) was then added to the mixture. The reaction was stirred at room temperature for 18 h (overnight). The reaction was diluted with methylene chloride, extracted one time with 1N HCl and two times with 5% sodium bicarbonate. The organic layer was separated, dried (MgSO₄) and the solvent removed under reduced pressure to give 2-(1-bromo-6-{[(2-ethyl-benzofuran-3-carbonyl)-amino]-methyl}-naphthalen-2-yloxy)-3-phenyl-propionic acid methyl ester (0.27 g, 100%) as a tan solid, mp 139–143° C.

Elemental Analysis for $C_{32}H_{28}BrNO_5$ Calc'd: C, 65.54; H, 4.81; N, 2.39 Found: C, 64.94; H, 4.78; N, 2.38

Step 2: 2-(1-Bromo-6-{[(2-ethyl-benzofuran-3-carbonyl)-amino]-methyl}-naphthalen-2-yloxy)-3-phenyl-propionic acid. A mixture of 2-(1-bromo-6-{[(2-ethyl-benzofuran-3-carbonyl)-amino]-methyl}-naphthalen-2-yloxy)-3-phenyl-propionic acid methyl ester (0.200 g, 0.341 mmol), prepared in the previous step, 1N NaOH (1.02 mL, 1.02 mmol), 10 mL of water and 100 mL of methanol was stirred under nitrogen at room temperature for 20 h (overnight). The reaction was acidified with 1N HCl until acidic by litmus paper. The methanol was removed under reduced pressure. The solid that precipitated and was collected by filtration and dried under reduced pressure to give the title compound (0.0576 g, 29%) as a white solid, mp 162–165° C.

Elemental Analysis for $C_{31}H_{26}BrNO_5+0.15\ mol\ H_2O$ Calc'd: C, 64.74; H, 4.61; N, 2.44 Found: C, 64.73; H, 4.40; N, 2.37

EXAMPLE 59

2-[1-Bromo-6-({[1-4-chloro-phenyl)-cyclopentanecarbonyl]-amino}-methyl)-naphthalen-2-yloxy]-3-phenyl-propionic acid In the same manner as described in Example 58, the title compound was isolated as a white solid, mp 207–208° C.

Elemental Analysis for $C_{32}H_{29}BrClNO_4+0.06\ H_2O$ Calc'd: C, 63.21; H, 4.83; N, 2.30 Found: C, 63.11; H, 4.71; N, 2.28

EXAMPLE 60

2-Bromo-6-({[5-(3-trifluoromethyl-phenyl)-furan-2-carbonyl]-amino}-methyl)-naphthalen-2-yloxy]-3-phenyl-propionic acid. In the same manner as described in Example 58, the title compound was isolated as a white solid, MS m/z: 636 [M–H]⁻.

Elemental Analysis for $C_{32}H_{23}BrF_3NO_5+0.22\ H_2O$ Calc'd: C, 59.83; H, 3.86; N, 2.18 Found: C, 59.50; H, 3.55; N, 2.14

General Experimental for Examples 61 to 72

Amine A: (5-Bromo-6-methoxy-naphthalen-2-ylmethyl)-methyl-amine. Prepared in step 7 of Example 36.

Amine B: Benzyl-(5-bromo-6-methoxy-naphthalen-2-ylmethyl)-amine. Prepared in the same manner as described Example 36 and substituting benzylamine for methylamine.

General Procedure for the Acylation of Amine A and Amine B. The acid chlorides were either commercially available or prepared as described in step 2 of Example 3. To a stirred solution of either Amine A or Amine B (2 mmol) and triethylamine (2.5 mmol) in $CH_2Cl_2$ (10 mL) was added a solution of the acid chloride (2.1 mmol) in $CH_2Cl_2$ (5 mL). The reactions were allowed to sit at room temperature for 6 h. Aqueous $NaHCO_3$ was added and the mixture was extracted with $CH_2Cl_2$ (3×20 mL). The combined organic phases were dried ($Na_2SO_4$), filtered and concentrated. The products were used in the next step without further purification.

EXAMPLE 61

2-(1-Bromo-6-{[(4cyclohexyl-benzoyl)-methyl-amino]-methyl}-naphthalen-2-yloxy)-3-phenyl-propionic acid Step 1: N-(5Bromo-6-hydroxy-naphthalen-2-ylmethyl)-4-cyclohexyl-N-methyl-benzamide. Boron trichloride (5.5 mL of a 1 M solution in methylene chloride; 5.5 mmol) was added under argon to a solution of N-(5-bromo-6-methoxy-naphthalen-2-ylmethyl)-4-cyclohexyl-N-methyl-benzamide (860 mg, 1.8 mmol), prepared by the general acylation procedure described above, and tetrabutylammonium iodide (2.04 g, 5.5 mmol) in 10 mL of methylene chloride at dry ice-acetone temperature. After the addition the reaction was allowed to warm to room temperature. The reaction was considered finished after HPLC/TLC analysis indicated the formation of a single product and the disappearance of the starting amide. The reaction was cooled to ice bath temperature followed by the addition of water. The organic layer was separated and the aqueous layer extracted three times with methylene chloride. The combined extracts were dried ($Na_2SO_4$) and the solvent removed under reduced pressure. The residue was purified by column chromatography (20–30% ethyl acetate in hexanes) to give N-(5-bromo-6-hydroxy-naphthalen-2-ylmethyl)-4-cyclohexyl-N-methyl-benzamide (799 mg, 97%), LCMS (Calc'd: 451.13; Found: 451.65).

Step 2: 2-(1-Bromo-6-{[(4-cyclohexyl-benzoyl)-methyl-amino]-methyl}-naphthalen-2-yloxy)-3-phenyl-propionic acid methyl ester. A mixture of N-(5-bromo-6-hydroxy-naphthalen-2-ylmethyl)-4-cyclohexyl-N-methyl-benzamide (799 mg, 1.51 mmol), prepared in the previous step, 3-phenyl-2-trifluoromethanesulfonyloxypropionic acid methyl ester (1.66 mmol), prepared in step 2 of Example 7, and cesium carbonate (985 mg, 3.0 mmol) in acetone was stirred at room temperature for 3 h. The reaction was partitioned between water and ethyl acetate. The aqueous layer was separated and extracted three times with ethyl acetate. The combined extracts were dried ($Na_2SO_4$) and the solvent removed under reduced pressure. Purification of the residue by column chromatography using 10%–20% ethyl acetate-hexanes as the eluent gave 2-(1-bromo-6-{[(4-cyclohexyl-benzoyl)-methyl-amino]-methyl}-naphthalen-2-yloxy)-3-phenyl-propionic acid methyl ester (445 mg, 48%), LCMS ES+(Calc'd: 613.2; Found: 614.3).

Step 3: 2-(1-Bromo-6-{[(4-cyclohexyl-benzoyl)-methyl-amino]-methyl}-naphthalen-2-yloxy)-3-phenyl-propionic acid. A mixture of 2-(1-bromo-6-{[(4-cyclohexyl-benzoyl)-methyl-amino]-methyl}-naphthalen-2-yloxy)-3-phenyl-propionic acid methyl ester (445 mg, 0.68 mmol), prepared in the previous step, and 0.5 mL of 10% aqueous NaOH in THF was stirred at room temperature for 2.5 h. Aqueous 10% HCl was added until acidic and the reaction extracted three times with ethyl acetate. The combined extracts were dried ($Na_2SO_4$) and the solvent removed under reduced pressure to give the title compound (419 mg, 95%), MS m/z: 600 $[M+H]^+$.

Elemental Analysis for $C_{34}H_{34}BrNO_4$ Calc'd: C, 68.00; H, 5.71; N, 2.33 Found: C, 67.24; H, 5.93; N, 2.26

Examples 62 to 72 were prepared in the same manner as described for Example 61.

EXAMPLE 62

2-(1-Bromo-6-{[(2-butyl-benzofuran-3-carbonyl)-methyl-amino]-methyl}naphthalen-2-yloxy)-3-phenyl-propionic acid. MS m/z: 614 $[M+H]^+$.

Elemental Analysis for $C_{34}H_{32}BrNO_5$ Calc'd: C, 66.45; H, 5.25; N, 2.28 Found: C, 59.64; H, 5.10; N, 1.73

EXAMPLE 63

2-(1-Bromo-6-{[methyl-(4'-propyl-biphenyl-4-carbonyl)-amino]-methyl}-naphthalen-2-yloxy)-3-phenyl-propionic acid. MS m/z: 636 $[M+H]^+$.

Elemental Analysis for $C_{37}H_{34}BrNO_4$ Calc'd: C, 69.81; H, 5.38; N, 2.20 Found: C, 68.77; H, 5.53; N, 2.09

EXAMPLE 64

2-[1-Bromo-6-({[5-(3,5-dichloro-phenoxy)-furan-2-carbonyl]-methyl-amino}-methyl)-naphthalen-2-yloxy]-3-phenyl-propionic acid. MS m/z: 668 $[M+H]^+$.

Elemental Analysis for $C_{32}H_{24}BrCl_2NO_6$ Calc'd: C, 57.42; H, 3.61; N, 2.09 Found: C, 57.06; H, 3.62; N, 1.92

EXAMPLE 65

2-(1-Bromo-6-{[(3,5-di-tert-butyl-benzoyl)-methyl-amino]-methyl}-naphthalen-2-yloxy)-3-phenyl-propionic acid. MS m/z: 630 $[M+H]^+$.

Elemental Analysis for $C_{36}H_{40}BrNO_4$ Calc'd: C, 68.57; H, 6.39; N, 2.22 Found: C, 65.77; H, 6.33; N, 1.93

EXAMPLE 66

2-(1-Bromo-6-{[methyl-(1-phenyl-5-propyl-1H-pyrazole-4-carbonyl)-amino]-methyl}-naphthalen-2-yloxy)-3-phenyl-propionic acid. MS m/z: 626 $[M+H]^+$.

Elemental Analysis for $C_{34}H_{32}BrN_3O_4$ Calc'd: C, 65.18; H, 5.15; N, 6.71 Found: C, 63.19; H, 5.91; N, 4.89

EXAMPLE 67

2-[6-({Benzyl-[5-(3,5-dichloro-phenoxy)-furan-2-carbonyl]-amino}-methyl)-1-bromo-naphthalen-2-yloxy]-3-phenyl-propionic acid. MS m/z: 744 $[M+H]^+$.

Elemental Analysis for $C_{38}H_{28}BrCl_2NO_6$ Calc'd: C, 61.23; H, 3.79; N, 1.88 Found: C, 60.57; H, 4.40; N, 1.74

EXAMPLE 68

2-(6-{[Benzyl-(2-butyl-benzofuran-3-carbonyl)-amino]-methyl}-1-bromo-naphthalen-2-yloxy)-3-phenyl-propionic acid. MS m/z: 690 $[M+H]^+$.

Elemental Analysis for $C_{40}H_{36}BrNO_5$ Calc'd: C, 69.57; H, 5.25; N, 2.03 Found: C, 65.55; H, 4.95; N, 1.58

EXAMPLE 69

2-(6-{[Benzyl-(3,5-di-tert-butyl-benzoyl)-amino]-methyl}-1-bromo-naphthalen-2-yloxy)-3-phenyl-propionic acid. MS m/z: 706 [M+H]$^+$.

Elemental Analysis for $C_{42}H_{44}BrNO_4$ Calc'd: C, 71.38; H, 6.28; N, 1.98 Found: C, 67.64; H, 6.01; N, 1.60

EXAMPLE 70

2-(6-{[Benzyl-(4'-propyl-biphenyl-4-carbonyl)-amino]-methyl}-1-bromo-naphthalen-2-yloxy)-3-phenyl propionic acid. MS m/z: 712 [M+H]$^+$.

Elemental Analysis for $C_{43}H_{38}BrNO_4$ Calc'd: C, 72.47; H, 5.37; N, 1.97 Found: C, 71.53; H, 5.32; N, 1.71

EXAMPLE 71

2-(6-{[Benzyl-(4-cyclohexyl-benzoyl)-amino]-methyl}-1-bromo-naphthalen-2-yloxy-3-phenyl-propionic acid. MS m/z: 676 [M+H]$^+$.

Elemental Analysis for $C_{40}H_{38}BrNO_4$ Calc'd: C, 71.00; H, 5.66; N, 2.07 Found: C, 66.13; H, 6.25; N, 1.45

EXAMPLE 72

2-(6-{[Benzyl-(1-phenyl-5-propyl-1H-pyrozole-4-carbonyl)-amino]-methyl}-1-bromo-naphthalen-2-yloxy)-3-phenyl-propionic acid. MS m/z: 702 [M+H]$^+$.

Elemental Analysis for $C_{40}H_{36}BrN_3O_4$ Calc'd: C, 68.38; H, 5.16; N, 5.98 Found: C, 62.07; H, 5.52; N, 3.80

General Experimental for Examples 73 to 87

Step 1: The aryl acid (1 mmol) was charged into a 40 mL vial. Methylene chloride (2 mL) and oxalyl chloride (131 μL, 1.5 mmol) were added to the vial, followed by the addition of DMF (20 μL). The vial was capped and allowed to stand at room temperature overnight. The solvent was removed under reduced pressure to give the acid chloride, which was used without additional purification.

Step 2: 6-Methoxycarbonyl-methoxy-naphthalen-2-ylmethyl-ammonium; chloride. Prepared in step 3 of Example 13.

Step 3: 6-Methoxycarbonyl-methoxy-naphthalen-2-yl-ammonium; chloride. Prepared in a similar manner as described in step 2.

Library Procedure

Stock Solution 1: Acid chlorides (either commercially available or prepared as described in step 1) were dissolved in anhydrous THF (0.25 M).

Stock Solution 2: Either 6-methoxycarbonyl-methoxy-naphthalen-2-ylmethyl-ammonium; chloride or 6-methoxycarbonyl-methoxy-naphthalen-2-yl-ammonium; chloride were dissolved in anhydrous THF (0.25 M).

Stock Solution 3: Anhydrous THF solution of triethylamine (0.5 M).

To 2-dram reaction vials was added Stock Solution 2 (300 μL) and Stock Solution 3 (600 μL) followed by Stock Solution 1 (310 μL). The vials were capped and allowed to mix at room temperature for 48 h. The reactions were diluted with methylene chloride (1 mL) and water (1 mL) was added. The organic phase was removed and the aqueous phase extracted with methylene chloride (3×1 mL). The methylene chloride phases were concentrated in a clean 2-dram reaction vial. The residue was dissolved in MeOH:THF (1:1) and 2N aqueous sodium hydroxide was added (200 μL). The vials were capped and the reactions were allowed to sit at room temperature for 24 h, whereupon 1N aqueous HCl (500 μL) was added. The reaction mixture was extracted with methylene chloride (3×1 mL). The combined organic phases were concentrated to dryness in a tarred 2-dram vial to give the desired compounds of Examples 73 to 87. These compounds were dissolved to a constant concentration in DMSO (30 mM) and an aliquot (25 μL) was removed for HLPC and MS analysis.

EXAMPLE 73

(6-{[5-(2-Chloro-phenyl)-2-trifluoromethyl-furan-3-carbonyl]-amino}naphthalen-2-yloxy)-acetic acid HRMS Calc'd for $C_{24}H_{15}ClF_3NO_5$ [M−H]; 488.0518. Found: 488.05163.

EXAMPLE 74

(6-{[5-(3-Trifluoromethyl-phenyl)-furan-2-carbonyl]-amino}-naphthalen-2-yloxy)-acetic acid HRMS Calc'd for $C_{24}H_{16}F_3NO_5$ [M−H]; 454.09078. Found: 454.09084.

EXAMPLE 75

(6-{[1-(4-Chloro-phenyl)-cyclopentanecarbonyl]-amino}-naphthalen-2-yloxy)-acetic acid HRMS Calc'd for $C_{24}H_{22}ClNO_4$ [M−H]; 422.11646. Found: 422.1163

EXAMPLE 76

[6-(2-Benzyloxy-benzoylamino)-naphthalen-2-yloxy]-acetic acid)

HRMS Calc'd for $C_{26}H_{21}NO_5$ [M−H]; ND

EXAMPLE 77

[6-(3,5-Di-tert-butyl-benzoylamino)-naphthalen-2yl oxy]-acetic acid

HRMS Calc'd for $C_{27}H_{31}NO_4$ [M−H]; 432.21803. Found: 432.21804.

EXAMPLE 78

{6-[(5-Biphenyl-4-yl-2-trifluoromethyl-furan-3-carbonyl)-amino]-naphthalen-2-yloxy}-acetic acid HRMS Calc'd for $C_{30}H_{20}F_3NO_5$ [M−H]; 530.12208. Found: 530.12186.

EXAMPLE 79

(6-{[1-(4-Chloro-phenyl)-cyclohexanecarbonyl]-amino}-naphathalen-2-yloxy)-acetic acid HRMS Calc'd for $C_{25}H_{24}ClNO_4$ [M−H]; 436.13211. Found: 436.13191

EXAMPLE 80

(6-{[1-(4-Chloro-phenyl)-cyclobutanecarbonyl]-amino}-naphthalen-2-yloxy)-acetic acid HRMS Calc'd for $C_{23}H_{20}ClNO_4$ [M−H]; 408.10081. Found: 408.10064.

EXAMPLE 81

[6-({[5-(2-Chloro-phenyl)-2-trifluoromethyl-furan-3-carbonyl]-amino}-methyl)-naphthalen-2-yloxy]-acetic acid HRMS Calc'd for $C_{25}H_{17}ClF_3NO_5$ [M−H]; 502.06745. Found: 502.06735.

EXAMPLE 82

[6-({[2-Trifluoromethyl-5-(4-trifluoromethyl-phenyl)-furan-3-carbonyl]-amino}methyl)-naphthalen-2-yloxy]-acetic acid HRMS Calc'd for $C_{26}H_{17}F_6NO_5$ [M−H]; 536.09381. Found: 536.09381.

EXAMPLE 83

{6-[(2-Phenethyl-benzoylamino)-methyl]-naphthalen-2-yloxy}-acetic acid

HRMS Calc'd for $C_{28}H_{25}NO_4$ [M−H]; 438.17108. Found: 438.17083.

EXAMPLE 84

[6-({[1-(4-Chloro-phenyl)-cyclopentanecarbonyl]-amino}-methyl)-naphthalen-2-yloxy]-acetic acid HRMS Calc'd for $C_{25}H_{24}ClNO_4$ [M−H]; 436.13211. Found: 436.13193.

EXAMPLE 85

[6-({[5-(3-Trifluoromethyl-phenyl)-furan-2-carbonyl]-amino}-methyl)-naphthalen-2-yloxy]-acetic acid HRMS Calc'd for $C_{25}H_{18}F_3NO_5$ [M−H]; 468.10643. Found: 468.10648.

EXAMPLE 86

{6-[(3,5-Di-tert-butyl-benzoylamino)methyl]-naphthalen-2-yloxy}-acetic acid

HRMS Calc'd for $C_{28}H_{33}NO_4$ [M−H]; 446.23368. Found: 446.23367.

EXAMPLE 87

(6-{[(1-Phenyl-cyclopentanecarbonyl)-amino]-methyl}-naphthalen-2-yloxy)-acetic acid HRMS Calc'd for $C_{25}H_{25}NO_4$ [M−H]; 402.17108. Found: 402.17093.

What is claimed is:

1. A compound of the formula:

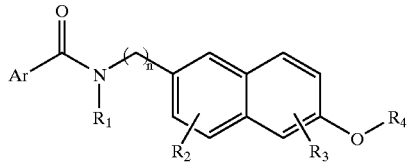

Wherein:

Ar is phenyl, naphthyl, furanyl, benzofuranyl, indolyl, pyrazolyl, oxazolyl, fluorenyl, phenylcycloalkane where the cycloalkane can be cyclopropyl, cyclobutyl, cyclopentyl or cyclohexyl and Ar can be optionally substituted by from 1 to 3 groups selected from $C_1$–$C_6$ alkyl, $C_1$–$C_6$ alkoxy, hydroxy, phenyl-$(CH_2)_{0-6}$—, phenyl-$(CH_2)_{0-6}$O—, $C_3$–$C_6$ cycloalkyl, —$(CH_2)$—$C_3$–$C_6$ cycloalkyl, halogen, $C_1$–$C_3$ perflouroalkyl and $C_1$–$C_3$ perfluoroalkoxy where phenyl can be substituted with from 1 to 3 groups selected from $C_1$–$C_6$ alkyl, $C_1$–$C_6$ alkoxy, phenyl, halogen, trifluoromethyl or trifluoromethoxy;

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy.

$R_4$ is —$CHR_5CO_2H$ or —$CH_2$-tetrazole where $R_5$ is hydrogen or benzyl; and n=0 or 1;

or a pharmaceutically acceptable salt or ester form thereof.

2. A compound of claim 1 of the formulae 1 or 2:

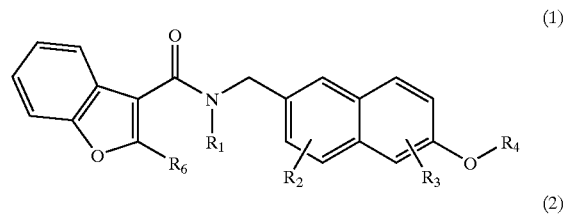

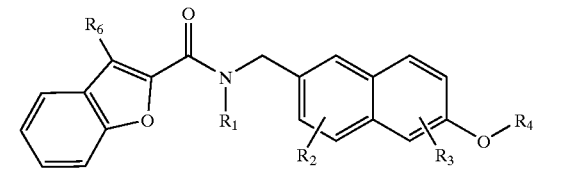

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy;

$R_4$ is —$CHR_5CO_2H$ or —$CH_2$-tetrazole;

$R_5$ is hydrogen or benzyl;

$R_6$ is selected from $C_1$–$C_6$ alkyl, $C_1$–$C_6$ alkoxy, hydroxy, phenyl-$(CH_2)_{0-6}$—, phenyl-$(CH_2)_{0-6}$O—, $C_3$–$C_6$, cycloalkyl, halogen, $C_1$–$C_3$ perflouroalkyl and $C_1$–$C_3$ perfluoroalkoxy;

where the phenyl ring in these $R_6$ groups can be substituted with $C_1$–$C_6$ alkyl, $C_1$–$C_6$ alkoxy, phenyl-$(CH_2)_{0-3}$—, halogen, trifluoromethyl or trifluoromethoxy;

or a pharmaceutically acceptable salt or ester form thereof.

3. A compound of claim 1 of the formula:

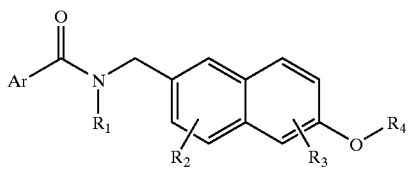

wherein:

Ar is a moiety selected from the group of:

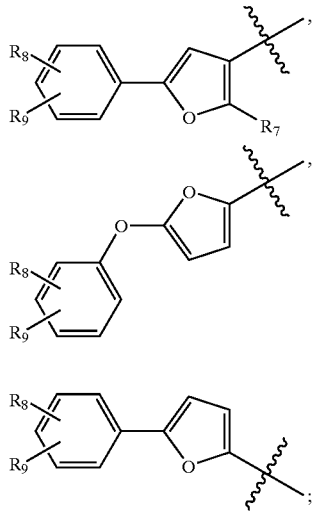

or $R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy;

$R_4$ is —$CHR_5CO_2H$ or —$CH_2$-tetrazole;

$R_5$ is hydrogen or benzyl;

$R_7$ is selected from $C_1$–$C_6$ alkyl, $C_1$–$C_6$ alkoxy, hydroxy, phenyl-$(CH_2)_{0-6}$—, phenyl-$(CH_2)_{0-6}$O—, $C_3$–$C_6$ cycloalkyl, halogen, $C_1$–$C_3$ perflouroalkyl and $C_1$–$C_3$ perfluoroalkoxy;

where the phenyl ring in these $R_7$ groups can be substituted with $C_1$–$C_6$ alkyl, $C_1$–$C_6$ alkoxy, phenyl, halogen, trifluoromethyl or trifluoromethoxy;

$R_8$ and $R_9$ are each independently selected from H, $C_1$–$C_6$ alkyl, $C_1$–$C_6$ alkoxy, phenyl-$(CH_2)_{0-3}$—, halogen, trifluoromethyl or trifluoromethoxy;

or a pharmaceutically acceptable salt or ester form thereof.

4. A compound of claim 1 of the formula:

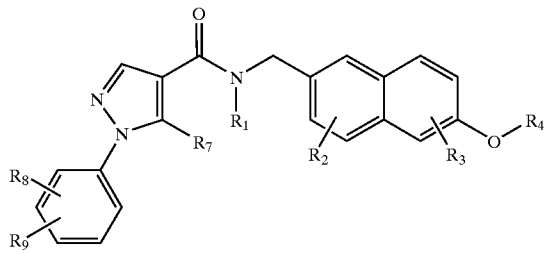

wherein:

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substituted with $C_1$–$C_6$ alkyl, $C_1$–$C_6$ alkoxy, halogen, trifluoromethyl or trifluoromethoxy;

$R_4$ is —$CHR_5CO_2H$ or —$CH_2$-tetrazole;

$R_5$ is hydrogen or benzyl;

$R_7$ is selected from $C_1$–$C_6$ alkyl, $C_1$–$C_6$ alkoxy, hydroxy, phenyl-$(CH_2)_{0-6}$—, phenyl-$(CH_2)_{0-6}$O—, $C_3$–$C_6$, cycloalkyl, halogen, $C_1$–$C_3$ perflouroalkyl and $C_1$–$C_3$ perfluoroalkoxy;

where the phenyl ring in these $R_7$ groups can be substituted with $C_1$–$C_6$ alkyl, $C_1$–$C_6$ alkoxy, phenyl-$(CH_2)_{0-3}$—, halogen, trifluoromethyl or trifluoromethoxy;

$R_8$ and $R_9$ are each independently selected from H, $C_1$–$C_6$ alkyl, $C_1$–$C_6$ alkoxy, phenyl, halogen, trifluoromethyl or trifluoromethoxy;

or a pharmaceutically acceptable salt or ester form thereof.

5. A compound of claim 1 of the formula:

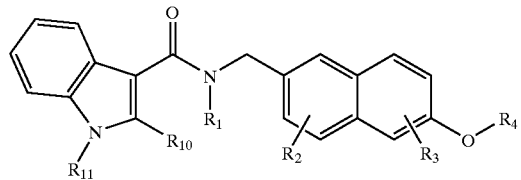

wherein:

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

$R_2$ and $R_3$ are independently hydrogen, $C_1$–$C_6$ alkyl, phenyl-$(CH_2)_{0-3}$—, halogen and $C_1$–$C_3$ perfluoroalkyl where phenyl can be substituted with $C_1$–$C_6$ alkyl, $C_1$–$C_6$ alkoxy, halogen, trifluoromethyl or trifluoromethoxy;

$R_4$ is —$CHR_5CO_2H$ or —$CH_2$-tetrazole;

$R_5$ is hydrogen or benzyl;

$R_{10}$ is selected from $C_1$–$C_6$ alkyl, $C_1$–$C_6$ alkoxy, hydroxy, $C_3$–$C_6$, cycloalkyl, halogen, $C_1$–$C_3$ perflouroalkyl and $C_1$–$C_3$ perfluoroalkoxy;

$R_{11}$ is selected from $C_1$–$C_6$ alkyl, phenyl-$(CH_2)_{0-6}$—, $C_3$–$C_6$ cycloalkyl, or —$(CH_2)$—$C_3$–$C_6$ cycloalkyl;

where the phenyl ring in these $R_7$ groups can be substituted with $C_1$–$C_6$ alkyl, $C_1$–$C_6$ alkoxy, phenyl, halogen, trifluoromethyl or trifluoromethoxy;

Or a pharmaceutically acceptable salt or ester form thereof.

6. A compound of claim 1 of the formula:

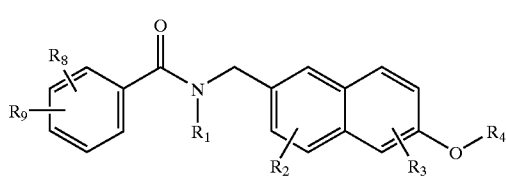

wherein:

$R_1$ is hydrogen, $C_1$–$C_6$ alkyl or phenyl-$(CH_2)_{1-6}$— where phenyl can be substituted with $C_1$–$C_6$ alkyl, $C_1$–$C_6$ alkoxy, halogen, trifluoromethyl or trifluoromethoxy;

R₂ and R₃ are independently hydrogen, $C_1$–$C_6$ alkyl, phenyl-$(CH_2)_{0-3}$—, halogen and $C_1$–$C_3$ perfluoroalkyl where phenyl can be substitute with $C_1$–$C_6$ alkyl, $C_1$–$C_6$ alkoxy, halogen, trifluoromethyl or trifluoromethoxy;

R₄ is —CHR₅CO₂H or —CH₂-tetrazole;

R₅ is hydrogen or benzyl;

R₈ and R₉ are each independently selected from H, $C_1$–$C_6$ alkyl, $C_1$–$C_6$ alkoxy, phenyl, halogen, trifluoromethyl or trifluoromethoxy;

or a pharmaceutically acceptable salt or ester form thereof.

7. A compound of claim 1 which is selected from the group of:

(6-{[Benzofuran-2-carbonyl)-amino]-methyl}-naphthalen-2-yloxy)-acetic acid;

Benzofuran-2-carboxylic acid [6-(2H-tetrazol-5-ylmethoxy-naphthalen-2-ylmethyl]-amide;

2-Butyl-benzofuran-3-carboxylic acid [6-(2H-tetrazol-5-ylmethoxy)-naphthalen-2-yl]-amide;

{6-[(2-Butyl-benzofuran-3-carbonyl)-amino]-naphthalen-2-yloxy}-acetic acid; or

2-Butyl-benzofuran-3-carboxylic acid [5-bromo-6-(2H-tetrazol-5-ylmethoxy)-naphthalen-2-yl]-amide; or a pharmaceutically acceptable salt or ester form thereof.

8. A compound of claim 1 which is selected from the group of:

{1-Bromo-6-[(2-butyl-benzofuran-3-carbonyl)-amino]-naphthalen-2-yloxy}-acetic acid;

2-{1-Bromo-6-[(2-butyl-benzofuran-3-carbonyl)-amino]-naphthalen-2-yloxy}-3-phenyl-propionic acid;

2-Butyl-benzofuran-3-carboxylic acid [6-(1H-tetrazol-5-ylmethoxy)-naphthalen-2-ylmethyl]-amide;

(6-{[(2-butyl-benzofuran-3-carbonyl)-amino]-methyl}-naphthalen-2-yloxy)-acetate;

[6-({[5-(4-Chloro-phenyl)-2-methyl-furan-3-carbonyl]-amino}-methyl)-naphthalen-2-yloxy]-acetic acid; or

[6-({[5-(4-Chloro-phenyl)-2-trifluoromethyl-furan-3-carbonyl]-amino}-methyl)-naphthalen-2-yloxy]-acetic acid; or a pharmaceutically acceptable salt or ester form thereof.

9. A compound of claim 1 which is selected from the group of:

(6-{[(1-phenyl-5-propyl-1H-pyrazole-4-carbonyl)-amino]-methyl}-naphthalen-2-yloxy)-acetic acid;

[6-({[1-(4-Chloro-phenyl)-5-propyl-1H-pyrazole-4-carbonyl]-amino}-methyl)-naphthalen-2-yloxy]-acetic acid;

[6-({[1-(4-Chloro-phenyl)-5-trifluoromethyl-1H-pyrazole-4-carbonyl]-amino}-methyl)-naphthalen-2-yloxy]-acetic acid;

(1-Bromo-6-{[(1-phenyl-5-propyl-1H-pyrazole-4-carbonyl)-amino]-methyl}-naphthalen-2-yloxy)-acetic acid; or

[1-Bromo-6-({[1-(4-chloro-phenyl)-5-trifluoromethyl-1H-pyrazole-4-carbonyl]-amino}-methyl)-naphthalen-2-yloxy]-acetic acid.

10. A compound of claim 1 which is selected from the group of:

2-Butyl-benzofuran-3-carboxylic acid [5-bromo-6-(1H-tetrazol-5-ylmethoxy)-naphthalen-2-ylmethyl]-amide;

2-(1-Bromo-6-{[(2-butyl-benzofuran-3-carbonyl)-amino]-methyl}-naphthalen-2-yloxy)-3-phenyl-propionic acid;

(1-bromo-6-{[(2-butyl-benzofuran-3-carbonyl)-amino]-methyl}-naphthalen-2-yloxy)-acetate;

2-Methyl-benzofuran-3-carboxylic acid [5-bromo-6-(1H-tetrazol-5-ylmethoxy)-naphthalen-2-ylmethyl]-amide; or 2-Ethyl-benzofuran-3-carboxylic acid [5-bromo-6-(1H-tetrazol-5-ylmethoxy)-naphthalen-2-ylmethyl]-amide; or a pharmaceutically acceptable salt or ester form thereof.

11. A compound of claim 1 which is selected from the group of:

1-Phenyl-5-propyl-1H-pyrazole-4-carboxylic acid [5-bromo-6-(1H-tetrazol-5-ylmethoxy)-naphthalen-2-ylmethyl]-amide;

2-Butyl-benzofuran-3-carboxylic acid [6-(1H-tetrazol-5-ylmethoxy)-5-p-tolyl-naphthalen-2-ylmethyl]-amide;

2-Butyl-benzofuran-3-carboxylic acid [5-phenyl-6-(1H-tetrazol-5-ylmethoxy)-naphthalen-2-ylmethyl]-amide;

2-Butyl-benzofuran-3-carboxylic [5-(4-methoxy phenyl)-6-(1H-tetrazol-5-ylmethoxy)-naphthalen-2-ylmethyl]-amide; or 2-Butyl-benzofuran-3-carboxylic acid [5-(4-chloro-phenyl)-6-(1H-tetrazol-5-ylmethoxy)-naphthalen-2-ylmethyl]-amide; or a pharmaceutically acceptable salt or ester form thereof.

12. A compound of claim 1 which is selected from the group of:

2-Butyl-benzofuran-3-carboxylic acid [5-(4-tert-butyl-phenyl)-6-(1H-tetrazol-5-ylmethoxy)-naphthalen-2-ylmethyl]-amide;

(6-{[(2-Butyl-benzofuran-3-carbonyl)-amino]-methyl}-1-phenyl-naphthanen-2-yloxy)-acetic acid;

2-[6-{[(2-Butyl-benzofuran-3-carbonyl)-amino]-methyl}-1-(4-chloro-phenyl)-naphthalen-2-yloxy]-3-phenyl-propionic acid;

2-[6-{[(2-Butyl-benzofuran-3-carbonyl)-amino]-methyl}-1-(4-methoxy-phenyl)-naphthalen-2-yloxy]-3-phenyl-propionate; or 2-Butyl-benzofuran-3-carboxylic acid [5-bromo-6-(1H-tetrazol-5-ylmethoxy)-naphthalen-2-ylmethyl]-methyl-amide; or a pharmaceutically acceptable salt or ester form thereof.

13. A compound of claim 1 which is selected from the group of:

2-Ethyl-benzofuran-3-carboxylic acid [5-bromo-6-(1H-tetrazol-5-ylmethoxy)-naphthalen-2-ylmethyl]-methyl-amide;

1-Phenyl-5-propyl-1H-pyrazole-4-carboxylic acid [5-bromo-6-(1H-tetrazol-5-ylmethoxy)-naphthalen-2-ylmethyl]-methyl-amide;

1-Benzyl-1H-indole-3-carboxylic acid [5-bromo-6-(1H-tetrazol-5-ylmethoxy)-naphthalen-2-ylmethyl]-methyl-amide;

2-Butyl-benzofuran-3-carboxylic acid methyl-[6-(1H-tetrazol-5-ylmethoxy)-naphthalen-2ylmethyl]-methyl-amide; or 2-Butyl-1-methyl-1H-indole-3-carboxylic acid [5-bromo-6-(1H-tetrazol-5-ylmethoxy)-naphthalen-2-ylmethyl]-methyl-amide; or a pharmaceutically acceptable salt or ester form thereof.

14. A compound of claim 1 which is selected from the group of:

1-Methyl-1H-indole-3-carboxylic acid [5-bromo-6-(1H-tetrazol-5-ylmethoxy)-naphthalen-2-ylmethyl]-methyl-amide;

5-(3,5-Dichloro-phenoxy)-furan-2-carboxylic acid [5-bromo-6-(1H-tetrazol-5-ylmethoxy)-naphthalen-2-ylmethyl]-methyl-amide;

3-Butyl-benzofuran-2-carboxylic acid [5-bromo-6-(1H-tetrazol-5-ylmethoxy)-naphthalen-2-ylmethyl]-methyl-amide;

2-Benzyl-3-(1-bromo-6-{[(3-butyl-benzofuran-2-carbonyl)-methyl-amino]-methyl}-naphthalen-2-yloxy)-propionic acid; or 3-Methyl-benzofuran-2-carboxylic acid [5-bromo-6-(1H-tetrazol-5-ylmethoxy)-naphthalen-2-ylmethyl]-methyl-amide; or a pharmaceutically acceptable salt or ester form thereof.

15. A compound of claim 1 which is selected from the group of:

2-benzyl-3-(1-bromo-6-{[methyl-(3-methyl-benzofuran-2-carbonyl)-amino]-methyl}-naphthalen-2-yloxy)-propionate;

3-Methyl-benzofuran-2-carboxylic acid [5-bromo-6-(1H-tetrazol-5-ylmethoxy)-naphthalen-2-ylmethyl]-amide;

2-(1-Bromo-6-{[(3-methyl-benzofuran-2-carbonyl)-amino]-methyl}-naphthalen-2-yloxy)-3-phenyl-propionic acid;

3-Phenethyl-benzofuran-2-carboxylic acid [5-bromo-6-(1H-tetrazol-5-ylmethoxy)-naphthalen-2-ylmethyl]-methyl-amide; or 2-(1-Bromo-6-{[methyl-(3-phenethyl-benzofuran-2-carbonyl)-amino]-methyl}-naphthalen-2-yloxy)-3-phenyl-propionic acid; or a pharmaceutically acceptable salt or ester form thereof.

16. A compound of claim 1 which is selected from the group of:

(1-Bromo-6-{[methyl-(3-phenethyl-benzofuran-2-carbonyl)-amino]-methyl}-naphthalen-2-yloxy)-acetic acid;

2-Butyl-benzofuran-3-carboxylic acid benzyl-[5-bromo-6-(1H-tetrazol-5-ylmethoxy)-naphthalen-2-ylmethyl]-amide;

2-Methyl-benzofuran-3-carboxylic acid benzyl-[5-bromo-6-(1H-tetrazol-5-ylmethoxy)-naphthalen-2-ylmethyl]-amide;

2-Ethyl-benzofuran-3-carboxylic acid benzyl-[5-bromo-6-(1H-tetrazol-5ylmethoxy)-naphthalen-2-ylmethyl)-amide; or 2-Butyl-benzofuran-3-carboxylic acid [5-bromo-6-(1H-tetrazol-5-ylmethoxy)-naphthalen-2-ylmethyl]-butyl-amide; or a pharmaceutically acceptable salt or ester form thereof.

17. A compound of claim 1 which is selected from the group of:

2-Methyl-benzofuran-3-carboxylic acid [5-bromo-6-(1H-tetrazol-5-ylmethoxy)-naphthalen-2-ylmethyl]-butyl-amide;

2-[1-Bromo-6-({[5-(3,5-dichloro-phenoxy)-furan-2-carbonyl]-amino}-methyl)-naphthalen-2-yloxy]-3-phenyl-propionic acid;

2-(1-Bromo-6-{[(1-phenyl-5-propyl-1H-pyrazole-4-carbonyl)-amino]-methyl}-naphthalen-2-yloxy)-3-phenyl-propionic acid;

2-{1-Bromo-6-[4-cyclohexyl-benzoylamino)-methyl]-naphthalen-2-yloxy}-3-phenyl-propionic acid; or 2-{1-Bromo-6-[(3,5-di-tert-butyl-benzoylamino)-methyl]-naphthalen-2-yloxy}-3-phenyl-propionic acid; or a pharmaceutically acceptable salt or ester form thereof.

18. A compound of claim 1 which is selected from the group of:

2-{1-Bromo-6-[(3-phenoxy-benzoylamino)-methyl]-naphthalen-2-yloxy}-3-phenyl-propionic acid;

2-(1-Bromo-6-{[(2-ethyl-benzofuran-3-carbonyl)-amino]-methyl}-naphthalen-2-yloxy)-3-phenyl-propionic acid;

2-[1-Bromo-6-({[1-4-chloro-phenyl)-cyclopentanecarbonyl]-amino}-methyl)-naphthalen-2-yloxy]-3-phenyl-propionic acid; or 2-Bromo-6-({[5-(3-trifluoromethyl-phenyl)-furan-2-carbonyl]-amino}-methyl)-naphthalen-2-yloxy]-3-phenyl-propionic acid; or a pharmaceutically acceptable salt or ester form thereof.

19. A compound of claim 1 which is selected from the group of:

2-(1-Bromo-6-{[(4-cyclohexyl-benzoyl)-methyl-amino]-methyl}-naphthalen-2-yloxy)-3-phenyl-propionic acid;

2-(1-Bromo-6-{[(2-butyl-benzofuran-3-carbonyl)-methyl-amino]-methyl}naphthalen-2-yloxy)-3-phenyl-propionic acid;

2-(1-Bromo-6-{[methyl-(4'-propyl-biphenyl-4-carbonyl)-amino]-methyl}-naphthalen-2-yloxy)-3-phenyl-propionic acid;

2-[1-Bromo-6-({[5-(3,5-dichloro-phenoxy)-furan-2-carbonyl]-methyl-amino}-methyl)-naphthalen-2-yloxy]-3-phenyl-propionic acid; or 2-(1-Bromo-6-{[(3,5-di-tert-butyl-benzoyl)-methyl-amino]-methyl}-naphthalen-2-yloxy)-3-phenyl-propionic acid; or a pharmaceutically acceptable salt or ester form thereof.

20. A compound of claim 1 which is selected from the group of:

2-(1-Bromo-6-{[methyl-(1-phenyl-5-propyl-1H-pyrazole-4-carbonyl)-amino]-methyl}-naphthalen-2-yloxy)-3-phenyl-propionic acid;

2-[6-({Benzyl-[5-(3,5-dichloro-phenoxy)-furan-2-carbonyl]-amino}-methyl)-1-bromo-naphthalen-2-yloxy]-3-phenyl-propionic acid;

2-(6-{[Benzyl-(2-butyl-benzofuran-3-carbonyl)-amino]-methyl}-1-bromo-naphthalen-2-yloxy)-3-phenyl-propionic acid;

2-(6-{[Benzyl-(3,5-di-tert-butyl-benzoyl)-amino]-methyl}-1-bromo-naphthalen-2-yloxy)-3-phenyl-propionic acid; or 2-(6-{[Benzyl-(4'-propyl-biphenyl-4-carbonyl)-amino]-methyl}-1-bromo-naphthalen-2-yloxy)-3-phenyl propionic acid; or a pharmaceutically acceptable salt or ester form thereof.

21. A compound of claim 1 which is selected from the group of:

2-(6-{[Benzyl-(4-cyclohexyl-benzoyl)-amino]-methyl}-1-bromo-naphthalen-2-yloxy-3-phenyl-propionic acid;

2-(6-{[Benzyl-(1-phenyl-5-propyl-1H-pyrozole-4-carbonyl)-amino]-methyl}-1-bromo-naphthalen-2-yloxy)-3-phenyl-propionic acid;

(6-{[5-(2-Chloro-phenyl)-2-trifluoromethyl-furan-3-carbonyl]-amino}naphthalen-2-yloxy)-acetic acid;

(6-{[5-(3-Trifluoromethyl-phenyl)-furan-2-carbonyl]-amino}-naphthalen-2-yloxy)-acetic acid; or (6-{[1-(4-Chloro-phenyl)-cyclopentanecarbonyl]-amino}-naphthalen-2-yloxy)-acetic acid; or a pharmaceutically acceptable salt or ester form thereof.

22. A compound of claim 1 which is selected from the group of:

[6-(2-Benzyloxy-benzoylamino)-naphthalen-2-yloxy]-acetic acid;

[6-(3,5-Di-tert-butyl-benzoylamino)-naphthalen-2yloxy]-acetic acid;

{6-[(5-Biphenyl-4-yl-2-trifluoromethyl-furan-3-carbonyl)-amino]-naphthalen-2-yloxy}-acetic acid;

(6-{[1-(4-Chloro-phenyl)-cyclohexanecarbonyl]-amino}-naphathalen-2-yloxy)-acetic acid; or (6-{[1-(4-Chloro-phenyl)-cyclobutanecarbonyl]-amino}-naphthalen-2-yloxy)-acetic acid; or a pharmaceutically acceptable salt or ester form thereof.

23. A compound of claim 1 which is selected from the group of:

[6-({[5-(2-Chloro-phenyl)-2-trifluoromethyl-furan-3-carbonyl]-amino}-methyl)-naphthalen-2-yloxy]-acetic acid;

[6-({[2-Trifluoromethyl-5-(4-trifluoromethyl-phenyl)-furan-3-carbonyl]-amino}methyl)-naphthalen-2-yloxy]-acetic acid;

{6-[(2-Phenethyl-benzoylamino)-methyl]-naphthalen-2-yloxy}-acetic acid;

[6-({[1-(4-Chloro-phenyl)-cyclopentanecarbonyl]-amino}-methyl)-naphthalen-2-yloxy]-acetic acid;

[6-({[5-(3-Trifluoromethyl-phenyl)-furan-2-carbonyl]-amino}-methyl)-naphthalen-2-yloxy]-acetic acid;

{6-[(3,5-Di-tert-butyl-benzoylamino)-methyl]-naphthalen-2-yloxy}-acetic acid; or (6-{[(1-Phenyl-cyclopentanecarbonyl)-amino]-methyl}-naphthalen-2-yloxy)-acetic acid; or a pharmaceutically acceptable salt or ester form thereof.

24. A pharmaceutical composition comprising a pharmaceutically effective amount of a compound of claim 1, or a pharmaceutically acceptable salt or ester form thereof, a pharmaceutically acceptable carrier or excipient.

25. A method of treatment of noninsulin dependent diabetes mellitus in a mammal, the method comprising administering to a mammal in need thereof a pharmaceutically effective amount of a compound of claim 1, or a pharmaceutically acceptable salt or ester form thereof.

26. A method of treatment or prevention of a prothrombotic or thrombotic state or event in a mammal, the method comprising administering to a mammal in need thereof a pharmaceutically effective amount of a compound of claim 1, or a pharmaceutically acceptable salt or ester form thereof.

27. A method of claim 26 wherein the prothrombotic or thrombotic state or event is associated with coronary artery or cerebrovascular disease.

28. A method of claim 26 wherein the prothrombotic or thrombotic state or event is formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

29. A method for the treatment of stroke associated with or resulting from atrial fibrillation in a mammal, comprising administering to a mammal in need thereof a pharmaceutically effective amount of a compound of claim 1.

30. A method for the treatment of deep vein thrombosis in a mammal, comprising administering to a mammal in need thereof a pharmaceutically effective amount of a compound of claim 1.

31. A method for the treatment of myocardial ischemia in a mammal, comprising administering to a mammal in need thereof a pharmaceutically effective amount of a compound of claim 1.

32. A method for the treatment of cardiovascular disease caused by noninsulin dependent diabetes mellitus in a mammal, comprising administering to a mammal in need thereof a pharmaceutically effective amount of a compound of claim 1.

33. A method for the treatment of the formation of atherosclerotic plaques in a mammal, comprising administering to a mammal in need thereof a pharmaceutically effective amount of a compound of claim 1.

34. A method for the treatment of chronic obstructive pulmonary disease in a mammal, comprising administering to a mammal in need thereof a pharmaceutically effective amount of a compound of claim 1.

35. A method for the treatment of renal fibrosis in a mammal, comprising administering to a mammal in need thereof a pharmaceutically effective amount of a compound of claim 1.

36. A method for the treatment of polycystic ovary syndrome in a mammal, comprising administering to a mammal in need thereof a pharmaceutically effective amount of a compound of claim 1.

37. A method for the treatment of Alzheimer's disease in a mammal, comprising administering to a mammal in need thereof a pharmaceutically effective amount of a compound of claim 1.

38. A method for the treatment of cancer in a mammal, comprising administering to a mammal in need thereof a pharmaceutically effective amount of a compound of claim 1.

* * * * *